United States Patent
Powell et al.

(10) Patent No.: US 7,125,718 B2
(45) Date of Patent: Oct. 24, 2006

(54) METHOD FOR INTRODUCING AND EXPRESSING GENES IN ANIMAL CELLS, AND BACTERIAL BLEBS FOR USE IN SAME

(75) Inventors: Robert J. Powell, Baltimore, MD (US); David Hone, Ellicott City, MD (US)

(73) Assignee: University of Maryland Biotechnology Institute, Baltimore, MD (US)

( * ) Notice: Subject to any disclaimer, the term of this patent is extended or adjusted under 35 U.S.C. 154(b) by 178 days.

(21) Appl. No.: 10/432,149

(22) PCT Filed: May 24, 2001

(86) PCT No.: PCT/US01/16904

§ 371 (c)(1), (2), (4) Date: Aug. 25, 2003

(87) PCT Pub. No.: WO01/89535

PCT Pub. Date: Nov. 29, 2001

(65) Prior Publication Data

US 2004/0266003 A1  Dec. 30, 2004

Related U.S. Application Data

(60) Provisional application No. 60/206,994, filed on May 24, 2000.

(51) Int. Cl.
C12N 15/88 (2006.01)
C12N 15/85 (2006.01)
C12P 21/06 (2006.01)
A61K 9/127 (2006.01)

(52) U.S. Cl. .................. 435/458; 435/69.1; 435/320.1; 424/450

(58) Field of Classification Search ................ 435/458; 514/44; 424/1.21, 1.73
See application file for complete search history.

(56) References Cited

U.S. PATENT DOCUMENTS 5,985,880 A  11/1999  Chang et al.

FOREIGN PATENT DOCUMENTS

WO  WO 93/22443  11/1993
WO  WO 93/23534  11/1993

OTHER PUBLICATIONS

Mooij P, Heeney JL, Rational development of prophylactic HIV vaccines based on structural and regulatory proteins, 2002, Vaccine 20:304-321.*

Sadelain M, Insertional oncogenesis in gene therapy: how much of a risk? 2004, Gene Therapy 11:569-573.*
Griesenbach U, Geddes DM, Alton EWFW, Gene therapy for cystic fibrosis: an example for lung gene therapy, 2004, Gene Therapy 11:S43-S50.*
Nanni P, Forni G, Lollini P-L, Cytokine gene therapy: hopes and pitfalls, 1999, Ann. Oncol. 10:261-266.*
Branch AD, A good antisense molecule is hard to find, 1998, trends Biochem. Sci. 23:45-50.*
Green DW, Roh H, Pippin J, Drebin JA, Antisense oligonucleotides: an evolving technology for the modulation of gene expression in human disease, 2000, J. Am. Coll. Surg. 191:93-105.*
Jen K-Y, Gewirtz AM, Suppression of gene expression by targeted disruption of messenger RNA: available options and current strategies, 2000, Stem Cells 18:307-319.*
Crooke ST, Basic principles of antisense therapeutics, 1998, from Antisense Research and Application, Chapter 1, Springer-Verlag, New York, pp. 1-50.*
Sioud M, Nucleic acid enzymes as a novel generation of anti-gene agents, 2001, Curr. Mol. Med. 1:575-588.*
Abbas AK, Lichtman AH, Pober JS, Cellular and Molecular Immunology 2nd ed. 1994, W.B. Sanunders Company, Philadeplphia, pp. 245 and 321.*
Kadurugamuwa JL, Beveridge TJ, Delivery of the non-membrane-permeative antibiotic gentamycin into mammalian cells by using Shigella flexneri membrane vesicles, 1998, Antimicrob Agents Chemother 42: 1476-1483.*
Al-Hendy, Ayman, et al.; Lipopolysaccharide O Side Chain of Yersinia enterocolitica O:3 Is an Essential Virulence Factor in an Orally Infected Murine Model; Infection and Immunity; Mar. 1992; vol. 60, No. 3, pp. 870-875; American Society for Microbiology; USA.
Altman, Sidney; Commentary—RNA enzyme gene therapy; Proc. Natl. Acad. Sci; Dec. 1993; vol. 90, pp. 10898-10900; Department of Biology, Yale University, New Haven, CT.
Archambault, Jacques, et al.; Genetics of Eukaryotic RNA Polymerases I, II, and III; Microbiological Reviews; Sep. 1993, vol. 57, No. 3, pp. 703-724; American Society for Microbiology.
Formal, S. B., et al.; Construction of a Potential Bivalent Vaccine Strain: Introduction of Shigella sonnei Form I Antigen Genes into the galE Salmonella typhi Ty21a Typhoid Vaccine Strain; Infection and Immunity; Dec. 1981; vol. 3, pp. 746-750; Division of Communicable Disease and Immunology, Walter Reed Army Institute of Research.

(Continued)

Primary Examiner—Dave Trong Nguyen
Assistant Examiner—Patrick S. Riggins
(74) Attorney, Agent, or Firm—Steven J. Hultquist; Intellectual Property/Technology Law

(57) ABSTRACT

A method for introducing and expressing genes in animal cells, in which the animal cells are transfected with bacterial blebs containing a eukaryotic expression cassette encoding the gene. Bacterial blebs comprising a eukaryotic expression cassette, wherein the bacterial blebs are derived from gram negative bacteria.

16 Claims, 5 Drawing Sheets

OTHER PUBLICATIONS

Beato, Miguel; Transcriptional control by nuclear receptors; The FASEB Journal; Apr. 1991; vol. 5, pp. 2044-2051; Institut für Molekularbiologie und Tumorforschung, I.M.T.

Braun, Stephen E., et al.; Metabolic correction and cross-correction of mucopolysaccharidosis type II (Hunter syndrome) by retroviral-mediated gene transfer and expression of human iduronate-2-sulfatase; Proc. Natl. Acad. Sci. USA; Dec. 1993; vol. 90, pp. 11830-11834; Medical Sciences.

Brundage, Rodney A., et al.; Expression and phosphorylation of the *Listeria monocytogenes* ActA protein in mammalian cells; Proc. Natl. Acad. Sci. USA; Dec. 1993, vol. 90, pp. 11890-11894.

Buchmeier, Nancy A., et al.; Recombination-deficient mutants of *Salmonella typhimurium* are avirulent and sensitive to the oxidative burst of macrophages; Molecular Microbiology, 1993, vol. 7, No. 6, pp. 933-936.

Bushman, Frederick D.; Tethering human immunodeficiency virus 1 integrase to a DNA site directs integration to nearby sequences; Proc. Natl. Acad. Sci. USA; Sep. 1994, vol. 91, pp. 9233-9237; Salk Institute for Biological Studies, La Jolla, California.

Chilton, Mary-Dell; Agrobacterium gene transfer: Progress on a "poor man's vector" for maize, Commentary; Proc. Natl. Acad. Sci USA; Apr. 1993, vol. 90, pp. 3119-3120; Ciba-Geigy Corporation, Research Triangle Park, North Carolina.

Curtiss, III, Roy, et al.; *Salmonella typhimurium* Deletion Mutants Lacking Adenylate Cyclase and Cyclic AMP Receptor Protein Are Avirulent and Immunogenic; Infection and Immunity, Dec. 1987, vol. 55, No. 12, pp. 3035-3043; American Society for Microbiology.

Dargis, M.; Modification in Penicillan-Binding Proteins during In Vivo Development of Genetic Competence of *Haemophilus influenzae* Is Associated with a Rapid Change in the Physiological State of Cells; Infection and Immunity; Oct. 1992, vol. 60, No. 10, pp. 4024-4031; American Society for Microbiology.

d'Hauteville, Hélène, et al., Phosphorylation of IcsA by cAMP-dependent protein kinase and its effect on intercellular spread of *Shigella flexneri*; Molecular Microbiology; 1992, vol. 6, No. 7, pp. 833-841; Unité de Pathogénie Microbienne Moléculaire et Unité 199.

Doggett, Teresa A., et al., Immune Responses to *Streptococcus sobrinus* Surface Protein Antigen A Expressed by Recombinant *Salmonella typhimurium*; Infection and Immunity; May 1993, vol. 61, No. 5, pp. 1859-1866; American Society for Microbiology.

Dreiseikelmann, Brigitte; Translocation of DNA across Bacterial Membranes; Microbiological Reviews; Sep. 1994, vol. 58, No. 3, pp. 293-316; Mikrobiologie/Gentechnologie, Universität Bielefeld, Bielefeld Germany.

Elsinghorst, Eric A.; Molecular Cloning of Epithelial Cell Invasion Determinants from Enterotoxigenic *Escherichia coli*; Invection and Immunity; Jun. 1992, vol. 60, No. 6, pp. 2409-2417; Department of Bacterial Immunology, Washington, DC.

Flynn, J. L., et al.; Generation of a cytotoxic T-lymphocyte response using a *Salmonella* antigen-delivery system; Molecular Microbiology; 1990, vol. 4, No. 12, pp. 2111-2118; Department of Molecular Biology, Research Institute of Scripps Clinic, La Jolla, California.

Fynan, Ellen F., et al.; DNA vaccines: Protective immunizations by parenteral, mucosal, and gene-gun inoculations; Proc. Natl. Acad. Sci. USA; Dec. 1993, vol. 90, pp. 11478-11482; Department of Pathology, University of Massachusetts Medical School, Worcester, Massachusetts.

Galán, Jorge E., et al.; Expression of *Salmonella typhimurium* Genes Required for Invasion Is Regulated by Changes in DNA Supercoiling; Infection and Immunity; Jun. 1990, pp. 1879-1885; Department of Biology; Washington University, St. Louis, Missouri.

Gao, Xiao-Ming, et al.; Recombinant *Salmonella typhimurium* Strains That Invade Nonphagocytic Cells Are Resistant to Recognition by Antigen-Specific Cytotoxic T Lymphocytes; Infection and Immunity; Sep. 1992, vol. 60, No. 9, pp. 3780-3789; Institute of Molecular Medicine and Nuffield Department of Pathology, John Radcliffe Hospital, Oxford and The Wellcome Research Laboratories, Beckenham, Kent, UK.

Goodman, Stacey, et al.; Recombinant Adeno-Associated Virus Mediated Gene Transfer Into Hematopoietic Progenitor Cells; Blood; Sep. 1994, vol. 84, No. 5, pp. 1492-1500; The American Society of Hematology.

Harborne, Nerina R., et al.; Transcriptional control, translation and function of the products of the five open reading frames of the *Escherichia coli nir* operon; Molecular Microbiology; 1992, vol. 6, No. 19, pp. 2805-2813; School of Biochemistry, University of Birmingham, Birmingham, UK.

Holloway, B.W., et al.; Genetics for all bacteria; Annual Review of Microbiology, Article 23, Annual 1993, vol. 47, pp. 659-685; North Carolina Libraries for Virtual Education (NCLIVE).

Ishihama, Akira; Role of the RNA polymerase a subunit in transcription activation; Molecular Microbiology; 1992, vol. 6, No. 22, pp. 3283-3288; Department of Molecular Genetics, National Institute of Genetics, Mishima, Shizuoka, Japan.

Kerppola, Tom K., et al.; RNA polymerase: regulation of transcript elongation and termination; The FASEB Journal; Oct. 1991, vol. 5, pp. 2833-2842; Division of Biochemistry and Molecular Biology, University of California, Berkeley, California.

Kolodka, Tadeusz M., et al.; Gene therapy for diabetes mellitus in rats by hepatic expression of insulin; Proc. Natl. Acad. Sci. USA; Medical Sciences; Apr. 1995, vol. 92, pp. 3293-3297; Howard Hughes Medical Institute and Departments of Cell Biology, Pathology, and Medicine, Baylor College of Medicine, Houston, Texas.

Kwaga, Jacob K.P., et al.; A *carAB* Mutant of Avian Pathogenic *Escherichia coli* Serogroup O2 Is Attenuated and Effective as a Live Oral Vaccine against Colibacillosis in Turkeys; Infection and Immunity; Sep. 1994, vol. 62, No. 9, pp. 3766-3772; American Society for Microbiology.

Lange, Roland, et al.; The nlpD gene is located in an operon with rpoS on the *Escherichia coli* chromosome and encodes a novel lipoprotein with a potential function in cell wall formation; Molecular Microbiology; 1994, vol. 13, No. 4, pp. 733-743; Department of Biology, University of Konstanz, Konstanz, Germany.

Libby, Stephen J., et al.; A cytolysin encoded by *Salmonella* is required for survival within macrophages; Proc. Natl. Acad. Sci USA; Microbiology; Jan. 1994, vol. 91, pp. 489-493; Department of Molecular Biology, The Research Institute of Scripps Clinic, La Jolla, California.

Long, David M., et al.; Self-cleaving catalytic RNA; The FASEB Journal; Jan. 1993, vol. 7, pp. 25-30; Department of Chemistry and Biochemistry, University of Colorado, Boulder, Colorado.

Mahieu, M., et al.; Construction of a Ribozyme Directed Against Human Interleukin-6 mRNA: Evaluation of Its Catalytic Activity in Vitro and In Vivo; Blood; Dec. 1994, vol. 84, No. 11, pp. 3758-3765; The American Society of Hematology.

Mann, Barbara J., et al.; Sequence of a cysteine-rich galactose-specific lectin of *Entamoeba histolytica*; Proc. Natl. Acad. Sci Usa; Medical Sciences; Apr. 1991, vol. 88, pp. 3248-3252; Departments of Medicine and Microbiology, University of Virginia; Charlottesville, Virginia.

Mastrangeli, Andrea; et al.; Diversity of Airway Epithelial Cell Targets for In Vivo Recombinant Adenovirus-mediated Gene Transfer; The Journal of Clinical Investigation; Jan. 1993, vol. 91(1), pp. 225-234; The American Society for Clinical Investigation, Inc.

Miller, W.G., et al.; DNA from diverse sources manifests cryptic low-level transcription in *Escherichia coli*; Molecular Microbiology; 1990, vol. 4, No. 6, pp. 881-893; Department of Microbiology, University at California at Los Angelos, Los Angelos, California.

Nabel, Gary J., et al.; Direct gene transfer with DNA-liposome complexes in melanoma: Expression, biologic activity, and lack of toxicity in humans; Proc. Natl. Acad. Sci. USA; Medical Sciences; Dec. 1993; vol. 90, pp. 11307-11311; Howard Hughes Medical Institute, Depts. Of Internal Medicine, Biological Chemistry, Pediatrics, Surgery & Pathology, University of Michigan Medical Center, Ann Arbor, Michigan.

Nnalue, Ndubisi A., et al.; Tests of the Virulence and Live-Vaccine Efficacy of Auxotrophic and *galE* Derivatives of *Salmonella choleraesuis*; Infection and Immunity; Apr. 1987, vol. 55, No. 4, pp. 955-962; American Society for Microbiology.

Noriega, Fernando R., et al., Construction and Characterization of Attenuated ΔaroA ΔvirG *Shigella flexneri* 2a Strain CVD 1203, a Prototype Live Oral Vaccine; Infection and Immunity; Nov. 1994, vol. 62, No. 11, pp. 5168-5172; American Society for Microbiology.

Platt, Terry; Rho and RNA: models for recognition and response; Molecular Microbiology; 1994, vol. 11, No. 6, pp. 983-990; Department of Biochemistry, University of Rochester Medical Center; Rochester, New York.

Russell, David G., et al.; Effective Immunization Against Cutaneous Leishmaniasis with Defined Membrane Antigens Reconstituted into Liposomes; The Journal of Immunology; Feb. 15, 1988, vol. 140, No. 4, pp. 1274-1279; The American Association of Immunologists.

Schafer, Rosana, et al.; Induction of a Cellular Immune Responses to a Foreign Antigen by a Recombinant *Listeria monocytogenes* Vaccine; The Journal of Immunology; Jul. 1, 1992, vol. 149, No. 1, pp. 53-59; The American Association of Immunologists.

Schena, Mark, et al.; A steroid-inducible gene expression system for plant cells; Proc. Natl. Acad. Sci. USA; Dec. 1991, vol. 88, pp. 10421-10425; Genetics.

Schödel, Florian, et al.; Hepatitis B Virus Nucleocapsid/pre-S2 Fusion Proteins Expressed in Attenuated *Salmonella* For Oral Vaccination; The Journal of Immunology; Dec. 15, 1990, vol. 145, No. 12; The American Association of Immunologists.

Schödel, Florian, et al.; Hybrid Hepatitis B Virus Core-Pre-S Proteins Synthesized in Avirulent *Salmonella typhimurium* and *Salmonella typhi* for Oral Vaccination; Infection and Immunity; May 1994, vol. 62, No. 5, pp. 1669-1676; American Society for Microbiology.

Shoemaker, Charles, et al.; cDNA cloning and functional expresion of the *Schistosoma mansoni* protective antigen triose-phospate isomerase; Proc. Natl. Acad. Sci. USA; Mar. 1992, vol. 89, pp. 1842-1846; Immunology.

Simonet, Michel, et al.; Immunization with Live *aroA* Recombinant *Salmonella typhimurium* Producing Invasin Inhibits Intestinal Translocation of *Yersinia pseudotuberculosis*; Infection and Immunity; Mar. 1994, vol. 62, No. 3, pp. 863-867; American Society for Microbiology.

Stabel, Thomas J., et al.; Swine Immunity to an Attenuated *Salmonella typhimurium* Mutant Containing a Recombinant Plasmid Which Codes for Production of a 31-Kilodalton Protein of *Brucella abortus*; Infection and Immunity; Sep. 1991, vol. 59, No. 9, pp. 2941-2947; American Society for Microbiology.

Steinhoff, Ulrich, et al.; Prevention of autoimmune lysis by T cells with specificity for a heat shock protein by antisense oligonucleotide treatment; Proc. Natl. Acad. Sci. USA; May 1994, vol. 91, pp. 5085-5088; Immunology.

Tacket, Carol O., et al.; Comparison of the Safety and Immunogenicity of ΔaroC ΔaroD and Δcya Δcrp *Salmonella typhi* Strains in Adult Volunteers; Infection and Immunity; Feb. 1992, vol. 60, No. 2, pp. 536-541; American Society for Microbiology.

Theisen, Michael, et al.; Molecular Cloning, Nucleotide Sequence, and Characterization of *lppB*, Encoding an Antigenic 40-Kilodalton Lipoprotein of *Haemophilus sommus*; Infection and Immunity, May 19993, vol. 61, No. 5, pp. 1793-1798; American Society for Microbiology.

Topham, David J., et al.; A synthetic peptide from the third hypervariable region of major histocompatibility complex class II β chain as a vaccine for treatment of experimental autoimmune encephalomyelitis; Proc. Natl. Acad. Sci. USA; Aug. 1994, vol. 91, pp. 8005-8009; Immunology.

Turner, S.J., et al., *Salmonella typhimurium* ΔaroA aroD Mutants Expressing a Foreign Recombinant Protein Induce Specific Major Histocompatibility Complex Class 1-Restricted Cytotoxic T Lymphocytes in Mice; Infection and Immunity; Dec. 1993; vol. 61, No. 12, pp. 5374-5380; American Society for Microbiology.

Walker, Mark J., et al.; Specific Lung Mucosal and Systemic Immune Responses after Oral Immunization of Mice with *Salmonella typhimurium aroA*, *Salmonella typhi* TY21a, and Invasive *Escherichia coli* Expressing Recombinant Pertussis Toxin S1 Subuni; Infection and Immunity; Oct. 1992; vol. 60, No. 10, pp. 4260-4268; American Society for Microbiology.

Walsh, Christopher E., et al.; A Functionally Active Retrovirus Vector for Gene Therapy in Fanconi Anemia Group C; Blood; Jul. 1994, vol. 84, No. 2, pp. 453-459; Hematology Branch, NHLBI, National Institutes of Health, Bethesda, Maryland.

Whitmire, William M., et al.; Specific and Nonspecific Responses of Murine B Celles to Membranes Blebs of *Borrelia burgdorferi*; Infection and Immunity; Apr. 1993, vol. 61, No. 4, pp. 1460-1467; American Soceity for Microbiology.

Wick, Mary Jo., et al.; Parameters That Influence the Efficiency of Processing Antigenic Epitopes Expressed in *Salmonella typhimurium*; Infection and Immunity; Oct. 1994, vol. 62, No. 10, pp. 4542-4548; American Society for Microbiology.

Yang, D. M., et al., Oral *Salmonella typhimurium* (AroA) Vaccine Expressing a Major Leishmanial Surface Protein (gp63) Preferentially Induces T Helper 1 Cells and Protective Immunity Against Leishmaniasis; The Journal of Immunology; Oct. 1990, vol. 145, No. 7, pp. 2281-2285; The American Association of Immunologists.

Spetzler, J., et al., "A novel strategy for the synthesis of the cysteine-rich protective antigen of the malaria merozoite surface protein (MSP-1)." International Journal of Peptide & Protein Research, vol. 43 (1994), pp. 351-358.

Lee, C., et al., "Studies of a sperm/placenta cross-reacting antigen, STX-10." Journal of Reproductive Immunology (1993), vol. 25, pp. 249-264.

Guadagni, F., et al., "*In vitro* and *in vivo* regulation of human tumor antigen expression by human recombinant interferons: a review." The International Journal of Biological Markers, vol. 9, No. 1 (1994), pp. 53-60.

Sansonetti, P., et al., "Plasmid-mediated invasiveness of <<*Shigella*-like >> *Escherishia coli*." Annals of Microbiology, vol. 132 A (1982), pp. 351-355.

Miller, A., et al., "Cytokine-mediated gene therapy for cancer." Annals of Surgical Oncology, vol. 1, No. 5 (1994), pp. 436-450.

Larson, D., et al., "Control points in eucaryotic ribosome biogenesis." Biochemistry and Cellular Biology, vol. 69 (1991), pp. 5-19.

Golumbek, P., et al., "The antitumor immune response as a problem of self-nonself discrimination: Implications for immunotherapy." Immunology Research, vol. 12 (1993), pp. 183-192.

Jensen, T., et al., "Correction of steroid sulfatase deficiency by gene transfer into basal cells of tissue-cultured epidermis from patients with recessive x-linked ichthyosis." Experimental Cell Research, vol. 209 (1993), pp. 392-397.

Stankovics, J., et al., "Cloning of functional alpha propionyl CoA carboxylase and correction of enzyme deficientcy in *pccA* fibroblasts." American Journal of Human Genetics, vol. 52 (1993), pp. 144-151.

Zabner, J., et al., "Adenovirus-mediated gene transfer transiently corrects the chloride transport defect in nasal epithelia of patients with cystic fibrosis." Cell, vol. 75 (1993), pp. 207-216.

Alegre, M., et al., "Immunomodulation of transplant rejection using monoclonal antibodies and soluble receptors." Digestive Diseases and Sciences, vol. 40, No. 1 (Jan. 1995), pp. 58-64.

Coulie, P., et al., "Genes coding for tumor antigens recognized by human cytolytic T lymphocytes." Journal of Immunotherapy, vol. 14 (1993), pp. 104-109.

Kolvya, S., et al., "The Vi antigen of *Salmonella typhi*: molecular analysis of the *viaB* locus." Journal of General Microbiology, vol. 138 (1992), pp. 297-304.

Gattuso, P., et al., "Adenosquamous carcinoma of the prostate." Human Pathology, vol. 26, No. 1 (Jan. 1995), pp. 123-126.

Foa, R., "Interleukin-2 and gene therapy in the management of acute lymphoblastic leukemia." Baillière's Clinical Haematology, vol. 7, No. 2 (Jun. 1994), pp. 421-431.

Levine, M. & Tacket, C., "Recombinant live cholera vaccines." Chp. 26, Vibrio cholerae and Cholera: Molecular to Global Perspectives, Ed. Wachsmuth, I. (1994), pp. 395-411.

Hoiseth, S. & Stocker, B., "Aromatice-dependent *Salmonella typhimurium* are non-virulent and effective as live vaccines." Nature, vol. 291 (May 1981), pp. 238-239.

Belmont, J., et al., "Expression of human adenosine deaminase in murine haematopoietic progenitor cells following retroviral transfer." Nature, vol. 322 (Jul. 1986), pp. 385-391.

Ratnor, L., et al., "Complete nucleotide sequence of the AIDS virus, HTLV-III." Nature, vol. 313 (Jan. 1985), pp. 277-283.

Plautz, G., et al., "Selective elimination of recombinant genes in vivo with a suicide retroviral vector." The New Biologist, vol. 3, No. 7 (Jul. 1991), pp. 709-715.

Wormington, M., "Poly(A) and translation: development control." Current Opinion in Cell Biology, vol. 5 (1993), pp. 950-954.

Guzman, L., et al., "FtsL, an essential cytoplasmic membrane protein involved in cell division in *Escherichia coli*." Journal of Bacteriology, vol. 174, No. 23 (Dec. 1992), pp. 7716-7728.

De Aizpurua, H. & Russell-Jones, G., "Oral vaccination: Identifaction of classes of proteins that provoke an immune response upon oral feeding." Journal of Experimental Medicine, vol. 167 (Feb. 1988), pp. 440-451.

Feng, Z., et al., "Pfs2400 can mediate antibody-dependent malaria transmission inhibition and may be the *Plasmodium falciparum* 11.1 gene product." Journal of Experimental Medicine, vol. 177 (Feb. 1993), pp. 273-281.

Dorward, D., et al., "Export and intercellular transfer of DNA via membrane blebs of *Neisseria gonorrhoeae*." Journal of Bacteriology, vol. 171, No. 5 (May 1989), pp. 2499-2505.

Groisman, E., et al., "*Salmonella typhimurium phoP* virulence gene is a transcriptional regulator." Proceeding of the National Academy of Sciences, vol. 86 (Sep. 1989), pp. 7077-7081.

Gustafson, C., et al., "Mutagenesis of the paracrystalline surface protein array of *Aeromonas salmonicida* by endogenous insertion elements." Journal of Molecular Biology, vol. 237 (1994), pp. 452-463.

Hall, S., "IL-12 at the crossroads." Science, vol. 268, No. 5216 (Jun. 1995), pp. 1432-1434.

Duke, G., et al., "Sequence and structural elements that contribute to efficient encephalomyocarditis viru RNA translation." Journal of Virology, vol. 66, No. 3 (Mar. 1992), pp. 1602-1609.

Felgner, P., et al., "Lipofection: A highly efficient, lipid-mediated DNA-transfection procedure." Proceedings of the National Academy of Sciences, vol. 84, No. 21 (Nov. 1987), pp. 7413-7417.

Gorfinkiel, L., et al., "Sequence and regulation of the *uapA* gene encoding a uric acid-xanthine permease in the fungus *Aspergillus nidulans*." The Journal of Biological Chemistry, vol. 268, No. 31 (Nov. 1993), pp. 23376-23381.

Camilli, A., et al., "*Listeria monocytogenes* mutants lacking phosphatidylinositol-specific phospholipase C are avirulent." Journal of Experimental Medicine, vol. 173 (Mar. 1991), pp. 751-754.

Chamberlain, L., et al., "*Neisseria gonorrhoeae* strain MS11 harbouring a mutation in gene *aroA* is attenuated and immunogenic." Microbial Pathogenesis, vol. 15 (1993), pp. 51-63.

Charbit, A., et al., "Expression and immunogenicity of the V3 loop from the envelope of human immunodeficiency virus type 1 in an attenuated *aroA* strain of *Salmonella typhimurium* upon genetic coupling to two *Escherichia coli* carrier proteins." Vaccine, vol. 11, No. 12 (1993), pp. 1221-1228.

Chatterjee, S., et al., "Dual-target inhibition of HIV-1 in vitro by means of an adeno-associated virus antisense vector." Science, vol. 258, No. 5087 (Nov. 1992), pp. 1485-1488.

Buchmeier, M. & Zinkernagel, R., "Immunodominant T cell epitope from signal sequence." Science, vol. 257, No. 5073 (Aug. 1992), p. 1142.

Cárdenas, L. & Clements, J., Stability, immunogenicity and expression of foreign antigens in bacterial vaccine vectors. Vaccine, vol. 11, No. 2 (1993), pp. 126-135.

Cignetti, A., et al., "Transduction of the IL2 gene into human acute leukemia cells: induction of tumor rejection without modifying cell proliferation and IL2 receptor expression." Journal of the National Cancer Institute, vol. 86 (1994), p. 785.

Hess, J., et al., "*Listeria monocytogenes* p60 supports host cell invasion by and in vivo survival of attenuated *Salmonella typhimurium*." Infection and Immunity, vol. 63, No. 5 (May 1995), pp. 2047-2053.

Karow, M., et al., "Isolation and characterization of the *Escherichia coli htrB* gene, whose product is essential for bacterial viability above 33° C. in rich media." Journal of Bacteriology, vol. 173, No. 2 (Jan. 1991), pp. 741-750.

Williamson, C., et al., "Expression of the lysostaphin gene of *Staphylococcus simulans* in a eukaryotic system." Applied and Environmental Microbiology, vol. 60, No. 3 (Mar. 1994), pp. 771-776.

Long, D. & Uhlenbeck, O., "Self-cleaving catalytic RNA." The FASEB Journal, vol. 7, No. 1 (1993), pp. 25-30.

Stevenson, G. & Manning, P., "Galactose epimerasaless (*GalE*) mutant G30 of *Salmonella typhimurium* is a good potential live oral vaccine carrier for fimbrial antigens." FEMS Microbiology Letters, vol. 28, No. 3 (Jul. 1985), pp. 317-321.

Harris, A., et al., "Gene therapy through signal transduction pathways and angiogenic growth factors as therapeutic targets in breast cancer." Cancer, vol. 74, No. 3 (Aug. 1994), pp. 1021-1026.

Wang, C., et al., "Direct gene delivery of human tissue kallikrein reduces blood pressure in spontaneously hypertensive rats." The Journal of Clinical Investigation, vol. 95, No. 4 (Apr. 1995), pp. 1710-1716.

Wu, G. & Wu, C., "Receptor-mediated gene delivery and expression in Vivo." The Journal of Biological Chemistry, vol. 263, No. 29 (Oct. 1988), pp. 14621-14624.

Xiang, Z., et al., "Vaccination with a plasmid vector carrying the rabies virus glycoprotein gene induces protective immunity against rabies virus." Virology, vol. 199 (1994), pp. 132-140.

Zambryski, P., "Basic processes underlying *Agrobacterium*-mediated DNA transfer to plant cells." Annual Review of Genetics, vol. 22 (1988), pp. 1-30.

Wu, J., et al., "Expression of immunogenic epitopes of hepatitis B surface antigen with hybrid flagellin proteins by a vaccine strain of *Salmonella*." Proceedings of the National Academy of Sciences, vol. 86, No. 12 (Jun. 1989), pp. 4726-4730.

Stauffer, L. & Stauffer, G., "Characterization of the *gcv* control region from *Escherichia coli*." Journal of Bacteriology, vol. 176, No. 20 (Oct. 1994), pp. 6159-6164.

Sadoff, J., et al., "Oral *Salmonella typhimurium* vaccine expressing circumsporozoite protein protects against malaria." Science, vol. 240, No. 4850 (Apr. 1988), pp. 336-338.

Sachs, A & Wahle, E., "Poly(A) tail metabolism and function in eucaryotes." The Journal of Biological Chemistry, vol. 268, No. 31 (Nov. 1993), pp. 22955-22958.

Remenick, J., et al., "Human Immunodeficiency virus tat transactivation: induction of a tissue-specific enhancer in a nonpermissive cell line." Journal of Virology, vol. 65, No. 10 (Oct. 1991), pp. 5641-5646.

Recorbet, G., et al., "Conditional suicide system of *Escherichia coli* released into soil that uses the *Bacillus subtilis sacB* gene." Applied and Environmental Microbiology, vol. 59, No. 5 (May 1993), pp. 1361-1366.

Pappo, I., et al., "Administration of systemic or local interluekin-2 enhances the anti-tumor effects of interleukin-12 gene therapy," Journal of Surgical Research, vol. 58 (1995), pp. 218-226.

Park, U., et al., "*Salmonella typhimurium* mutants lacking NAD pyrophosphatase." Journal of Bacteriology, vol. 170, No. 8 (Aug. 1988), pp. 3725-3730.

Morein, S., et al., "Separation of inner and outer membrane vesicles from *Escherichia coli* in self-generating percoll gradients." Analytical Biochemistry, vol. 216 (1994), pp. 47-51.

Yamada, O., et al., "Activity and cleavage site specificity of an anti-HIV-1 hairpin ribozyme in human T cells." Virology, vol. 205 (1994), pp. 121-126.

Radolf, J., et al., "Analysis of *Borrelia burgdorferi* membrane architecture by freeze-fracture electon microscopy." Journal of Bacteriology, vol. 176, No. 1 (Jan. 1994), pp. 21-31.

Neidhardt, F., et al., "The genetics and regulation of heat-shock proteins." Annual Review of Genetics, vol. 18 (1984), pp. 295-329.

Molin, S., et al., "Suicidal genetic elements and their use in biological containment of bacteria." Annual Review of Microbiology, vol. 47 (1993), pp. 139-166.

Karow, M. & Georgopoulos, C., "Isolation and characteristic of the *Escherichia coli msbB* gene, a multicopy suppressor of null mutations in the high-temperature requirement gene *htrB*." Journal of Bacteriology, vol. 174, No. 3 (Feb. 1992), pp. 702-710.

Mackow, E., et al., "DNA amplication-restricted transcription-translation: rapid analysis of rhesus retrovirus neutralization sites." Proceeding of the National Academy of Sciences, vol. 87, No. 2 (Jan. 1990), pp. 518-522.

Miller, S., et al., "A two-component regulatory system (phoP phoQ) controls Salmonella typhimurium virulence." Proceedings of the National Academy of Sciences, vol. 86, No. 13 (Jul. 1989), pp. 5054-5058.

Miller, S. & Mekalanos, J., "Constitutive expression of the PhoP regulon attenuates Salmonella virulence and survival within macrophages." Journal of Bacteriology, vol. 172, No. 5 (May 1990), pp. 2485-2490.

Keverne, E., "Genomic imprinting in the brain." Current Opinion in Neurobiology, vol. 7 (1997), pp. 463-468.

Kadurugamuwa, J., et al., "Surface action of gentamicin on Pseudomonas aeruginosa." Journal of Bacteriology, vol. 175, No. 18 (Sep. 1993), pp. 5798-5805.

Framis, V., et al., "Effect of anti-human sperm monoclonal antibodies on mouse in vitro fertilization." Immunological Investigations, vol. 23, No. 1 (1994), pp. 15-24.

Huxley, C., et al., "Ordering up big MACs." Bio/Technology, vol. 12 (Jun. 1994), pp. 586-589.

Hodgson, C., "The vector void in gene therapy." Bio/Technology, vol. 13 (Mar. 1995), pp. 222-225.

Ortega_Barria, E. & Pereira, M., "A novel T. cruzi heparin-binding protein promotes fibroblast adhesion and penetration of engineered bacteria and trypanosomes into mammalian cells." Cell (Oct. 1991), vol. 67, pp. 411-421.

Hillyer, G., et al., "Fasciola hepatica: host responders and nonresponders to parasite glutathione S-transferase." Experimental Parasitology, vol. 74 (1992), pp. 176-186.

Levine, M., et al., "Safety, infectivity, immunogenicity, and in vivo stability of two attenuated auxotrophic mutant strains of Salmonella typhi ,541Ty and 543Ty, as live oral vaccines in humans." Journal of Clinical Investigations, vol. 79 (Mar. 1987), pp. 888-902.

Boué, F., et al., "Human sperm-zona pellucida interaction is inhibited by an antiserum against a hamster sperm protein." Biology of Reproduction, vol. 51 (1994), pp. 577-587.

Read, D., et al., "Transmission-blocking antibodies against multiple, non-variant target epitopes of the Plasmodium falciparum gamete surface antigen Pfs230 are all complement-fixing." Parasite Immunology, vol. 16 (1994), pp. 511-519.

Alving, C., "Lipopolysaccharide, lipid A, and liposomes containing lipid A as immunologic adjuvants." Immunobiology, vol. 187 (1993), pp. 430-446.

Truss, M., et al., "Transcriptional control by steroid hormones." Journal of Steroid Biochemistry and Molecular Biology, vol. 4, No. 3 (1992), pp. 241-248.

Andersen, J., et al., "Herpesvirus-mediated gene delivery into the rat brain: specificity and efficiency of the neuron-specific enolase promoter." Cellular and Molecular Neurobiology, vol. 13, No. 5 (1993), pp. 503-515.

Carroll, J. & Taichman, L., "Characterization of the human involucrin promoter using a transient β-galactosidase assay." Journal of Cell Science, vol. 103 (1992), pp. 925-930.

Rosenkranz, A., et al., "Receptor-mediated endocytosis and nuclear transport of a transfecting DNA construct." Experimental Cell Research, vol. 199 (1992), pp. 323-329.

McGrane, M., et al., "Developmental regulation and tissue-specific expression of a chimaeric phosphoenolpyruvate carboxykinase/bovine growth hormone gene in transgenic animals." Journal of Reproduction and Fertility, vol. 41 (1990), pp. 17-23.

Palker, T., et al., "Poluvalent human immunodeficiency virus synthetic immunogen comprised of envelope gp120 T helper cell sites and B cell neutralized epitopes." The Journal of Immunology, vol. 142, No. 10 (May 1989), pp. 3612-3619.

Li, B., et al., "Identification of paramyosin as a potential protective antigen against Brugia malayi infection in jirds." Molecular and Biochemical Parasitology, vol. 49 (1991), pp. 315-324.

Levine, M., et al., "Safety, immunogenicity, and efficacy of recombinant live oral cholera vaccines, CVD 103 and CVD 103-HgR." The Lancet (Aug. 27, 1998), pp. 467-475.

Guiso, N., et al., "Protective activity of Bordetella adenylate cyclase-hemolysin against bacterial colonization." Microbial Pathogenesis, vol. 11 (1991), pp. 423-431.

Monsur, K., et al., "Immunogenicity of a candidate live oral typhoid/cholera hybrid vaccine in humans." The Journal of Infectious Diseases, vol. 159, No. 1 (Jan. 1989), pp. 145-146.

O'Gaora, P., et al., "Yersinia enterocolitica aroA mutants as carriers of the B subunit of the Escherichia coli heat-labile enterotoxin to the immune system." Microbial Pathogenesis, vol. 9 (1990), pp. 105-116.

Bienkowska-Szewczyk, K., et al., "The R gene product of bacteriophage λ is the murein transglycosylase." Molecular and General Genetics, vol. 184 (1981), pp. 111-114.

Hone, D., et al., "Construction of defined galE mutants of Salmonella for use as vaccines." The Journal of Infectious Diseases, vol. 156, No. 1 (Jul. 1987), pp. 167-174.

Mengaud, J., et al., "Identification of phosphatidylinositol-specific phospholipase C activity in Listeria monocytogenes: a novel type of virulence factor?" Molecular Microbiology, vol. 5, No. 2 (1991), pp. 367-372.

McFarland, W. & Stocker, B., "Effect of different purine auxotrophic mutations on mouse-virulence of a Vi-positive strain of Salmonella dublin and of two strains of Salmonella typhimurium." Microbial Pathogenesis, vol. 3 (1987), pp. 129-141.

Baier, G., et al., "Construction and characterization of lck- and fyn-specific tRNA: ribosome chimeras." Molecular Immunology, vol. 31, No. 12 (1994), pp. 923-932.

Shaha, C., "Antibody-induced changes on rabbit sperm surface inhibit gamete interaction." Molecular Reproduction and Development, vol. 38 (1994), pp. 393-403.

Naz, R. & Ahmad, K., "Molecular identities of human sperm proteins that bind human zona pellucida: nature of sperm-zona interaction, tyrosine kinase activity, and involvement of FA-1." Molecular Reproduction and Development, vol. 39 (1994), pp. 397-408.

Frenkel, M., et al., "The isolation, characterization and cloning of a globin-like, host-protective antigen from the excretory-secretory products of Trichostrongylus colubriformis." Molecular and Biochemical Parasitology, vol. 50 (1992), pp. 27-36.

Kocken, C., et al., "Cloning and expression of gene coding for the transmission blocking target antigen Pfs48/45 of Plasmodium falciparum." Molecular and Biochemical Parasitology, vol. 61 (1993), pp. 59-68.

Mastroeni, P., et al., "Role of T cells, TNFα and IFNγ in recall of immunity to oral challenge with virulent salmonellae in mice vaccinated with live attenuated aro- salmonella vaccines." Microbial Pathogenesis, vol. 13 (1992), pp. 477-491.

Naito, M., et al., "prodcution of germline chickens, with high transmission rate of donor-derived gametes, produced by transfer of primordial germ cells." Molecular Reproduction and Development, vol. 39 (1994), pp. 153-161.

Burdon, T. & Wall, R., "Fate of microinjected genes in preimplantation mouse embryos." Molecular Reproduction and Development, vol. 33 (1992), 436-442.

Curiel, D., "High-efficiency gene transfer employing adenovirus-polylysine-DNA complexes." Nature immunity, vol. 12 (1994), pp. 141-164.

Melani, C., et al., "Cytokine gene transduction in tumor cells: interleukin (IL)-2 or IL-4 gene transfer in human melonoma cells." Nature Immunity, vol. 13 (1994), pp. 76-84.

Watanabe, M., et al., Lipsome-mediated DNA transfer into chicken primordial germ cell in vivo. Molecular Reproduction and Development, vol. 38 (1994), pp. 268-274.

Moss, B., "Replicating and host-restricted non-replicating vaccinia virus vectors for vaccine development." Developments in Biological Standardization, vol. 82 (1994), pp. 55-63.

Hug, P. & Sleight, R., "Liposomes for the transformation of eukaryotic cells." Biochimica et Biophysica Acta, vol. 1097 (1991), pp. 1-17.

Walden, R. & Schell, J., "Techniques in plant molecular biology—progress and problems." European Journal of Biochemistry, vol. 192 (Berlin 1990), pp. 563-576.

Hazinski, T., et al., "Localization and induced expression of fusion genes in the rat lung." American Journal of Respiratory Cell and Molecular Biology, vol. 4 (1991), pp. 206-209.

Pinnaduwage, P., et al., "Use of a quaternary ammonium detergent in liposome mediated DNA transfection of mouse L-cells." Biochemica et Biophysica Acta, vol. 985 (1989), pp. 33-37.

Neidhardt, F. & Van Bogelen, R., "Positive regulatory gene for temperature-controlled proteins in Escherichia coli." Biochemical and Biophysical Research Communications, vol. 100 No. 2 (May 1981), pp. 894-900.

Mestecky, J., "The common mucosal immune system and current strategies for induction of immune responses in external secretions." Journal of Clinical Immunology, vol. 7, No. 4 (1987), pp. 265-273.

Waldor, M. & Mekalanos, J., "Emergence of a new cholera pandemic: molecular analysis of virulence determinants in Vibrio cholerae O139 and development of a live vaccine prototype." The Journal of Infectious Diseases, vol. 170 (1994), 278-283.

Taylor, D., et al., "Development of a live, oral, attenuated vaccine against el tor cholera." The Journal of Infectious Diseases, vol. 170 (1994), pp. 1518-1523.

Donnenburg, M., et al., "Internalization of Escherichia coli into human kidney epithelial cells: comparison of fecal and pyelonephritis-associated strains." The Journal of Infectious Diseases, vol. 169 (1994), pp. 831-838.

Helftenbein, G., et al., "Expression of the uteroglobin promoter in epithelial cell lines from endometrium." Annals of the New York Academy of Sciences, vol. 622, No. 1 (1991), pp. 69-79.

Isberg, R. & Nhieu, G., "Binding and internalization of microorganisms by integrin receptors." Trends in Microbiology, vol. 2, No. 1 (Jan. 1994), pp. 10-13.

Robinson-Benion, C., et al., "Gene transplantation:combined antisense inhibition and gene replacement strategies." Leukemia, vol. 8, Suppl. 1 (1994), pp. S152-S155.

Black et al., "Prevention of Shigellosis by a Salmonella typhi-Shigella sonnei Bivalent Vaccine." The Journal of Infectious Diseases, vol. 155, No. 6, (Jun. 1987), pp. 1260-1265.

Reader et al., "Lysis Defective Mutants of Bacteriophage Lambda on the Role of the S Function in Lysis." Virology, vol. 43, (1971), pp. 623-637.

Rennell et al., "Phage P22 Lysis Genes: Nucleotide Sequences and Functional Relationships with T4 and λ Genes." Virology, vol. 143, (1985), pp. 280-289.

Cooper et al., "Invasiveness and Persistance of Salmonella enteritidis, Salmonella typhimurium, and a Genetically Defined S. enteritidis aroA Strain in Young Chickens." vol. 62, (1994), pp. 4739-4745.

Fairweather et al., "Oral Vaccination of Mice against Tetanus by Use of a Live Attenuated Salmonella Carrier." Infection and Immunity, vol. 58, No. 5, (May 1990), pp. 1323-1326.

Klipstein et al., "Protection in Rabbits Immunized with a Vaccine of Escherichia coli Heat-Stable Toxin Cross-Linked to the Heat-Labile Toxin B Subunit." Infection and Immunity, vol. 40, (1983), pp. 888-893.

Formal et al., "Construction of a Poetntial Bivalent Vaccine Strain: Introduction of Shigella sonnei Form I Antigen Genes into the galE Salmonella typhi Ty21a Typhoid Vaccine Strain." Infection and Immunity, vol. 34 (1981), pp. 746-750.

Yamamoto et al., "Enteroadhesion Fimbriae and Enterotoxin of Eschericha coli: Genetic Transfer to a Streptomycin-Resistant Mutant of the galE Oral Route Live-Vaccine Salmonella typhi Ty21a." Infection and Immunity, vol. 50, No. 3, (Dec. 1985), pp. 925-928.

Vaughan et al., "An Aromatic-Dependent Mutant of the Fish Pathogen Aeromonas salmonicida Is Attenuated in Fish and Is Effective as a Live Vaccine against the Salmonid Disease Furunculosis." Infection and Immunity, vol. 61, No. 5, (1993), pp. 2172-2181.

Galan et al., "Expression of Salmonella typhimurium Genes Required for Invasion is Regulated by Changes in DNA Supercoiling." vol. 58, No. 6, (Jun. 1990), pp. 1879-1885.

Goldberg et al., "Regulation of Surface Presentation of IcsA, a Shigella Protein Essential to Intracellular Movement and Spread, Is Growth Phase Dependent." Infection and Immunity, vol. 62, No. 12, (Dec. 1994), pp. 5664-5668.

Vile et al., "In vtiro and in Vivo Targeting of Gene Expression to Melanoma Cells." Cancer Research, vol. 53, (Mar. 1993), pp. 962-967.

Vile et al., "Systemic Gene Therapy of Murine Melanoma Using Tissue Specific Expression of the HSVtk Gene Involves an Immune Component." Cancer Research, vol. 54, (Dec. 1994), pp. 6228-6233.

Gomez et al., "The Bacillus subtilis Lipoprotein Lp1A causes cell lysis when expressed in Escherichia coli." Microbiology, vol. 140, (1990), pp. 1839-1845.

Morris et al., "Adenoviral-mediated Gene Transfer to Bladder in Vivo." The Journal of Virology, vol. 152, (1994), pp. 506-509.

Davis et al., "DNA-ases immunization induces continuous secretion of hapatitis B surface antigen and high levels of circulating antibody." Human Molecular Genetics, vol. 2, No. 11, (1993), pp. 1847-1851.

Woolf et al., "Gene transfer into the mammalian kidney: First steps towards renal gene therapy." Kidney International, vol. 43, Suppl. 39,(1993), pp. S-116-S-119.

Sabelnikov, A. G., "Nucleic Acid Transfer Through Cell Membranes: towards the Underlying Mechanisms." Pro. Biophys. Mole. Biol., vol. 62, (1994), pp. 119-152.

Cordier, et al., "Complete Recovery of Mice from a Pre-established Tumor by Direct Intratumoral Delivery of an Adenovirus Vector Harboring the Murine IL-2 Gene." Gene Therapy, vol. 2, (1995), pp. 16-21.

Galinski et al., "A Reticulocyte-Binding Protein Complex of Plasmodium vivax Merozoites." Cell, vol. 69, (1992), pp. 1213-1226.

Ott, Manfred. "Genetic Approaches to Study Legionella pneumophila Pathogenicity." FEMS Microbiology Reviews, vol. 14 (1994), pp. 161-176.

Vatteroni et al., "Analysis of Electroporation-Induced Genetic Damages in V79/AP4 Chinese Hamster Cells." Mutation Research, vol. 291 (1993), pp. 163-169.

Lessl et al., "Common Mechanisms in Bacterial Conjugation and Ti-Mediated T-DNA Transfer to Plant Cells." Cell, vol. 77 (1994), pp. 321-324.

Qin et al., "Gene Transfer for Transportation." Annals of Surgery, vol. 220, No. 4, pp. 508-519.

Conry et al., "A Carcinoembryonic Antigen Polynucleotide Vaccine has in Vivo Antitumor Activity." Gene Therapy, vol. 2 (1995), pp. 59-65.

Ahrenholtz et al., "A Conditional Suicide System in Escherichia coli Based on the Intracellular Degradation of DNA." Applied and Environmental Microbiology, vol. 60, No. 10 (1994), pp. 3746-3751.

Begg et al., "Cell Shape and Division in Escherichia coli: Experiments with Shpae and Division Mutants." Journal of Bacteriology, vol. 163, No. 2, (1985), pp. 615-622.

Bowers et al., "Advances in Molecular Biology: Implications for the future of clinical nutrition practice." Journal of the American Dietetic Association, vol. 95, No. 1, (1995), pp. 53-59.

Aggarwal et al., "Oral Salmonella: Malaria Circumsporozoite Recombinants Induce Specific CD8+ Cytotoxic T Cells." The Journal of Experimental Medicine, vol. 172 (1990), pp. 1083-1090.

Levine et al., "Vaccines to Prevent Bacterial Enteric Infections in Children." Pediatric Annals, vol. 22, (1993), pp. 719-724.

Gonzalez et al., "Salmonella typhi Vaccine Strain CVD 908 Expressing the Circumsporozoite Protein of Plasmodium falciparum: Strain Construction and Safety and Immunogenicity in Humans." The Journal of Infectious Diseases, vol. 169 (1994), pp. 927-931.

Stevenson et al., "Galactose epimeraseless (GAlE) mutant G30 of Salmonella typhimurium is a good potential live oral vaccine carrier for fimbral antigens." FEMS Microbiology Letters, vol. 28, (1985), pp. 317-321.

Hone et al., "A chromosomal integration system for stabilization of heterologous genes in *Samonella* based vaccine strains." Microbial Pathogenesis, vol. 5 (1988), pp. 407-418.

Cardenas et al., "Stability Immunogenicity, and Expression of Foreign Antigens in Bacterial Vaccine Vectors." Vaccine, vol. 11, No. 2 (1993), pp. 126-134.

Charbit et al., "Expression and Immunogenicity of the V3 Loop from the Envelope of Human Immunodeficiency Virus Type 1 in an Attenuated aroA strain of *Salmonella typhimurium* upon genetic coupling to two *Escherichia coli* carrier proteins." Vaccine, vol. 11, No. 12, (1993), pp. 1221-1227.

Curtiss III et al., "Recombinant *Salmonella* Vectors in Vaccine Development." Dev. Biol. Stand., vol. 82, (1994), pp. 23-33.

Hilleman, M. R., "Recombinant Vector Vaccines in Vaccinology." Dev. Biol. Stand., vol. 82, pp. 3-20.

Brett et al., "Influence of the Antigen Delivery System on Immunoglobulin Isotype Selection and Cytokine Production in Response to Influenza A Nucleoprotein." Immunology, vol. 80 (1993), pp. 306-312.

Chatfield et al., "Use of the nirB Promoter to Direct the Stable Expression of Heterologous Antigens in *Salmonella* Oral Vaccine Strains: Development of a Single-Dose Oral Tetanus Vaccine." Bio/Technology, vol. 10 (1992), pp. 888-891.

Van Damme et al., "Oral Immunization Against Cholera Toxinwith a Live *Yersinia enterocolitica* Carrier in Mice." Gastroenterology, vol. 103 (1992), 520-531.

Voorma et al., "Initiation of a Protein Synthesis in Eukaryotes." Molecular Biology Reports, vol. 19(1994), pp. 139-145.

Tuite et al., "Termination of Protein Synthesis." Molecular Biolgoy Reports, vol. 19, (1994), pp. 171-181.

Tung et al., "Targeted Inhibition of Immunodeficiency Virus Replication in Lymphocytes through Retroviral Mediated Gene Transfer." Arch. Virol., vol. 133 (1993), pp. 407-421.

Ledley, Fred. "Are Contemporary Methods for Somatic Gene Therapy Suitable for Clinical Applications?" Clin. Invest. Med., vol. 16, No. 1, (1993), pp. 78-85.

Caplen et al., "Liposome-mediated CFTR Gene Transfer to the Nasal Epithelium of Patients with Cystic Fibrosis." Nature Magazine, vol. 1, No. 1, (Jan. 1995), pp. 39-46.

Fujiwara et al., "Gene Therapeutics and Gene Therapy for Cancer." Current Opinions in Oncology, vol. 6, (1994), pp. 96-105.

Sullivan, Sean, "Development of Ribozymes for Gene Therapy." The Journal of Invest. Dermatology, vol. 103, No. 5, Supplement, (Nov. 1994), pp. 85-S-89-S.

Pardoll, Drew, "New Strategies for Active Immunotherapy with Genetically Engineered Tumor Cells." Current Opinion in Immunology, vol. 4, (1992), pp. 619-623.

Pardoll, Drew, "Immunotherapy with Cytokine Gene-Transduced Tumor Cells: the Next Wave in Gene Therapy for Cancer." Current Opinion in Immunology, vol. 4, (1992), pp. 1124-1129.

Steele et al., "Effect on Cancer Cells of Plasmids that Express Antisense RNA of Human Papillomavirus Type 18." Cancer Research, vol. 52, (1992), pp. 4706-4711.

Golumbek et al., "Controlled Release Biodegradable Cytokine Depots: A New Approach in Cancer Vaccine Design." Cancer Research, vol. 53, (1993), pp. 5841-5844.

Untawale et al., "Transforming Growth Factor-α Production and Autoinduction in a Colorectal Carcinoma Cell Line (DiFi) with an Amplified Epidermal Growth Factor Receptor Gene." Cancer Research, vol. 53, (1993), pp. 1630-1636.

Conry et al., "Immune Response to a Carcinoembryonic Antigen Polynucleotide Vaccine." Cancer Research, vol. 54, (1994), pp. 1164-1168.

Webster et al., "Protection of Ferrets Against Influenza Challenge with a DNA Vaccine to the Haemagglutinin." Vaccine, vol. 12, (1994), pp. 1495-1498.

Perales et al., "An evaluation of receptor-mediated Gene Transfer using Synthetic DNA-Ligand Complexes." Eur. J. Biochem., vol. 226, (1994), pp. 255-266.

Mittal et al., "Monitoring Foreign Gene Expression by a Human Adenovirus-based Vector Using the Firefly Luciferase Gene as a Reporter." Virus Research, vol. 28, (1993), pp. 67-90.

Setoguchi et al., "Intraperitonal In Vivo Gene Therapy to Deliver α1-Antitrypsin to the Systemic Circulation." Am. J. Respir. Cell Mol. Biol., vol. 10, (1994), pp. 369-377.

Bashir et al., "Evaluation of Defined Antigen Vaccines Against *Schistosoma bovis* and *S. Japonicum* in Bovines." Tropical and Geographical Medicine, vol. 46, No. 4, 1994, pp. 255-258.

Davis et al., "Direct Gene Transfer In Skeletal Muscle: Plasmid DNA-based Immunization against the Hepatitis B Virus Surface Antigen." Vaccine, vol. 12, No. 16, (1994), pp. 1503-1507.

Hoffman et al., "Protection Against Malaria by Immunization with a *Plasmodium yoelii* Circumsporozoite Protein Nucleic Acid Vaccine." vol. 12, No. 16, (1994), pp. 1529-1533.

Danko et al., "Direct Gene Transfer into Muscle." Vaccine, vol. 12, No. 16, (1994), pp. 1499-1502.

Harris, et al, "Gene Therapy through Signal Transduction Pathways and Angiogenic Growth Factors as Therapeutic Targets in Breast Cancer." Cancer, vol. 74, No. 3, Supplement, (Aug. 1994), pp. 1021-1024.

Vile et al., "Targeting of Cytokine Gene Expression to Malignant Melanoma Cells Using Tissue Specific Promoter Sequences." Annals of Oncology, vol. 5, Supplement 4, (1994), pp. S59-S65.

Magrath, I.T., "Prospects for the Therapeutic Use of Antisense Oligonucleotides in Malignant Lymphomas." Annals of Oncology, vol. 5, Supplement 1, (1994), pp. S67-S70.

Coovert et al., "Gene Therapy for Muscle Diseases." Current Opinion in Neurology, vol. 7, (1994), pp. 463-470.

Nabel, Elizabeth G., "Gene Therapy for Cardiovascular Disease." Circulation, vol. 91, No. 2, (Jan. 1995), pp. 541-545.

Zabner et al., "Safety and Efficacy of Repetitive Adenovirus-mediated Transfer of CFTR cDNA to Airway Epithelia of Primates and Cotton Rats." Nature Genetics, vol. 6, (Jan. 1994), pp. 75-83.

Grossman et al., "Successful ex vivo Gene Therapy Directed to Liver in a Patient with *Familial hypercholesterolaemia*." Nature Genetics, vol. 6, (Apr. 1994), pp. 335-341.

Engelhardt et al., "Direct Gene Transfer of Human CFTR into Human Bronchial Epithelia of Xenographs with E1-deleted Adenoviruses." Nature Genetics, vol. 4, (1993), pp. 27-33.

Bajocchi et al., "Direct in vivo Gene Transfer to Ependymal cells in the Central Nervous System Using Recombninant Adenovirus Vectors." Nature Genetics, vol. 3, (Mar. 1993), pp. 229-234.

Hengge et al., "Cytokine Gene Expression in Epidermis with Biological Effects Following Injection of Naked DNA." Nature Genetics, vol. 10, (Jun. 1995), pp. 161-166.

Spooner et al., "Polynucleotide Vaccination for Cancer Treatment (Review)." Internation Journal of Oncology, vol. 6, (1995), pp. 1203-1208.

Shillitoe et al., "Gene Therapy-Its Potential in the Management of Oral Cancer." Oral Oncol. Eur. J. of Cancer, vol. 30B, No. 3, pp. 143-154.

Chuah et al., "Inhibition of Human Immunodeficiency Virus Type-1 by Retroviral Vectors Expressing Antisense-TAR." Human Gene Therapy, vol. 5, (1994), pp. 1467-1475.

San et al., "Safety and Short-term Toxicity of a Novel Cationic Lipid Formulation for Human Gene Therapy." Human Gene Therapy, vol. 4, (1993), pp. 781-788.

Stewart et al., "Gene Transfer In Vivo with DNA-Liposome Complexes: Safety and Acute Toxicity in Mice." Human Gene Therapy, vol. 3, (1992), pp. 267-275.

Dropulic et al., "Gene Therapy for Human Immunodeficiency Virus Infection: Genetic Antiviral Strategies and Targets for Intervention." Human Gene Therapy, vol. 5, (1994), pp. 927-939.

Manthorpe et al., "Gene Therapy by Intramuscular Injection of Plasmid DNA: Studies on Firefly Lucierase Gene Expression in Mice." Human Gene Therapy, vol. 4, (1993), pp. 419-431.

Nabel et al., "A Molecular Genetic Intervention for AIDS—Effects of a Transdominant Negative Form of Rev." Human Gene Therapy, vol. 5, (1994), pp. 79-92.

Katsumi et al., "Humoral and Cellular Immunity to an Encoded Protein Induced by Direct DNA Injection." Human Gene Therapy, vol. 5, (1994), pp. 1335-1339.

Sorscher et al., "Gene Therapy for Cystic Fibrosis Using Cationic Liposoime Mediated Gene Transfer: A Phase I Trial of Safety and Efficacy in the Naval Airway." Human Gene Therapy, vol. 5, (1994), pp. 1259-1277.

Cech, Thomas R., "The efficiency and Versatility of Catalytic RNA: Implications for an RNA World." Gene, vol. 135 (1993), pp. 33-36.

Hone et al., "Evaluation in Volunteers of a Candidate Live Oral Attenuated *Salmonella typhi* Vector Vaccine." J. Clin. Invest., vol. 90, (1992), pp. 412-420.

Cech, Thomas R., "Catalytic RNA: Structure and Mechanism." Biochemical Society Transactions, vol. 21, (1993), pp. 229-234.

Quandt et al., "Versatile Suicide Vectors which Allow Direct Selection for Gene Replacement in Gram-negative Bacteria." Gene, vol. 127, (1993), pp. 15-21.

Dahler et al., "Expression Vectors Encoding Human Growth Hormone (hGH) controlled by Human Muscle-Specific Promoters: Prospects for Regulated Production of hGH delivered by myoblast transfer or intravenous Injection." Gene, vol. 145,(1994), pp. 305-310.

Meyer et al., "Inhibition of HIV-1 Replication by a High-copy-cumber Vector Expressing Antisense RNA for Reverse Transcriptase." Gene, vol. 129 (1993), pp. 263-268.

Wang, C.C., "A Novel Suicide Inhibitor Strategy for Antiparasitic Drug Development." J. of Cellular Biochem., vol. 45, (1991), pp. 49-53.

Geballe et al., "Initiation Codon with 5'-Leaders of mRNAs as Regulators of Translation." Trends in Biochem. Sci., vol. 19, (1994), pp. 159-164.

Rossi et al., "The Potential Use of Catalytic RNAs in Therapy of HIV Infection and Other Diseases." Pharmac. Ther., vol. 50, (1991), pp. 245-254.

Sachs, Alan B., "Messenger RNA Degradation in Eukaryotes." Cell, vol. 74 (1993), pp. 413-421.

Wahle, Elmar, "The End of the Massage: 3'-End Processing Leading to Polyadenylated Messenger RNA." BioEssays, vol. 14, No. 2, (1992), pp. 113-117.

Warne et al., "Direct Interaction of Ras and the Amino-Terminal Region of Raf-1 in Vitro." Nature, vol. 364, (Jul. 1993), pp. 352-355.

Koeppen et al., "Genetically Engineered Vaccines." Annals New York Academy of Sciences, vol. 690, (1993), pp. 244-255.

Milligan et al., "Antisense Therapeutics." Annals New York Academy of Sciences, vol. 716, (1994), pp. 228-241.

Farhood et al., "Cationic Liposomes for Direct Gene Transfer in Therapy of Cancer and Other Diseases." Annals New York Academy of Sciences, vol. 716, (1994), pp. 23-34.

Sonenberg, Nahum, "mRNA Translation: Influence of the 5' and 3' untranslated Regions." Current Opinion in Genetics and Development, vol. 4 (1994), pp. 310-315.

Hori et al., "The Role of Activators in Assembly of RNA Polymerase II Transcription Complexes." Current Opinion in Genetics and Development, vol. 4, (1994), pp. 236-244.

Morgan et al., "Retroviral Vectors Containing Putative Internal Ribosome Entry Sites: Development of a Polycistronic Gene Transfer System and Applications to Human Gene Therapy." Nucleic Acids Research, vol. 20, No. 6, (1992), pp. 1293-1299.

Richardson, John P., "Transcription Termination." Critical Reviews in Biochem. and Mol. Biol., vol. 28, No. 1, (1993), pp. 1-30.

Yoshimura et al., "Expression of Human Cystic Transmembrane Conductance Regulator Gene in the Mouse Lung after in Vivo Intratracheal Plasmid-Mediated Gene Transfer." Nucleic Acids Research, vol. 20, No. 12, (1992), pp. 3233-3240.

Eick et al., "From Initiation to Elongation: Comparison of Transcription by Prokaryotic and Eukaryotic RNA Polymerases." TIG, vol. 10, No. 8, (1994), pp. 292-296.

Proudfoot, Nick, "Poly(A) Signals." Cell, vol. 64, (1991), pp. 671-674.

Louis et al., "Signals Determining Translational Start-Site Recognition in Eukaryotes and their Role in Prediction of Genetic Reading Frames." Mol. Biol. Reports, vol. 13, (1988), pp. 103-115.

Libby, et al., "The Role of RNA Polymerase in Transcriptional Fidelity." Mol. Microbiol., vol. 5, No. 5, (1991), pp. 999-1004.

Chandra et al., "Fine Structure of *Calymmatobacterium granulomatis* with Particular Reference to the Surface Structure." Indian J. Med. Res., vol. 93, (Jul. 1991), pp. 225-231.

Dorward et al., "DNA Is Package within Membrane-Derived Vesicles of Gram-Negative but Not Gram-Positive Bacterial." Applied and Environmental Microbiology, vol. 56, No. 6, (1990), pp. 1960-1962.

Flynn, JoAnne L., "Recombinant BCG as an Antigen Delivery System." Cellular and Molecular Biology, vol. 40, Suppl. I, (1994), pp. 31-36.

Robinson et al., "Protection against a lethal Influenza Virus Challenge by Immunization with a Haemagglutinin-Expressing Plasmid." Vaccine, vol. 11, No. 9, (1993), pp. 957-960.

Verma et al., "Construction of Aromatic Dependent *Shigella flexneri* 2a Live Vaccine Candidate Strains: Deletion Mutations in the aroA and the aroD Genes." Vaccine, vol. 9, (1991), pp. 6-8.

Hone et al., "Construction of Genetically Defined Double aro Mutants of *Salmonella typhi*." Vaccine, vol. 9, (1991), pp. 810-815.

Kardnell et al., "Auxotrophic Live Oral *Shigella flexneri* Vaccine Protects Monkeys Against Challenge with *S. flexneri* of Different Serotypes." Vaccine, vol. 10, Issue 3, (1992) pp. 167-174.

Chatfield et al., "Construction of a Genetically Defined *Salmonella typhi* Ty2 aroA, aroC Mutant for the Engineering of a Candidate Oral Typhoid-Tatanus Vaccine." Vaccine, vol. 10, Issue 1, (1992), pp. 53-59.

Tacket et al., "Clinical Acceptability and Immunogenicity of CVD 908 *Salmonella typhi* Vaccin Strain." Vaccine, vol. 10, Issue 7, (1992), pp. 443-446.

ATCC No.: 13950.

Lagranderie et al., "Oral Immunization with Recombinant BCG Induces Cellular and Humoral Immune Responses Against the Foreign Antigen." Vaccine, vol. 11, Issue 13, (1993), pp. 1283-1290.

* cited by examiner

Serum IgG responses to Salmonella after vaccination with non-pyrogenic *Salmonella* Blebs Serum IgG responses to gp120

Figure 3A

CCATGGATGATAAGTTATATCGGGCAGATTCTAGACCTCCTGATGAAATAAA
GCAGTCAGGTGGTCTTATGCCAAGAGGACAGAGTGAGTACTTTGACCGAGGT
ACTCAAATGAATATCAACCTTTATGATCATGCAAGAGGAACTCAGACGGGAT
TTGTTAGGCACGATGATGGATATGTTTCCACCTCAATTAGTTTGAGAAGTGCC
CACTTAGTGGGTCAAACTATATTGTCTGGTCATTCTACTTATTATATATGTT
ATAGCCACTGCACCCAACATGTTTAACGTTAATGATGTATTAGGGGCATACA
GTCCTCATCCAGATGAACAAGAAGTTTCTGCTTTAGGTGGGATTCCATACTCC
CAAATATATGGATGGTATCGAGTTCATTTTGGGGTGCTTGATGAACAATTACA
TCGTAATAGGGGCTACAGAGATAGATATTACAGTAACTTAGATATTGCTCCA
GCAGCAGATGGTTATGGATTGGCAGGTTTCCCTCCGGAGCATAGAGCTTGGA
GGGAAGAGCCGTGGATTCATCATGCACCGCCGGGTTGTGGGAATGCTCCAAG
ATCATCGTAAGCGGCCGCTCGAGTCTAGAGGGCCCGTTTAAACCCGCTGATC
AGCCTCGACTGTGCCTTCTAGTTGCCAGCCATCTGTTGTTTGCCCCTCCCCGT
GCCTTCCTTGACCCTGGAAGGTGCCACTCCCACTGTCCTTTCCTAATAAAATG
AGGAAATTGCATCGCATTGTCTGAGTAGGTGTCATTCTATTCTGGGGGGTGGG
GTGGGGCAGGACAGCAAGGGGGAGGATTGGGAAGACAATAGCAGGCATGCT
GGGGATGCGGTGGGCTCTATGGCTTCTGAGGCGGAAAGAACCAGCTGGGGCT
CTAGGGGGTATCCCCACGCGCCCTGTAGCGGCGCATTAAGCGCGGCGGGTGT
GGTGGTTACGCGCAGCGTGACCGCTACACTTGCCAGCGCCCTAGCGCCCGCT
CCTTTCGCTTTCTTCCCTTCCTTTCTCGCCACGTTCGCCGGCTTTCCCCGTCAA
GCTCTAAATCGGGGCATCCCTTTAGGGTTCCGATTTAGTGCTTTACGGCACCT
CGACCCCAAAAAACTTGATTAGGGTGATGGTTCACGTAGTGGGCCATCGCCC
TGATAGACGGTTTTTCGCCCTTTGACGTTGGAGTCCACGTTCTTTAATAGTGG
ACTCTTGTTCCAAACTGGAACAACACTCAACCCTATCTCGGTCTATTCTTTTG
ATTTATAAGGGATTTTGGGGATTTCGGCCTATTGGTTAAAAAATGAGCTGATT
TAACAAAAATTTAACGCGAATTAATTCTGTGGAATGTGTGTCAGTTAGGGTGT
GGAAAGTCCCCAGGCTCCCCAGGCAGGCAGAAGTATGCAAAGCATGCATCTC
AATTAGTCAGCAACCAGGTGTGGAAAGTCCCCAGGCTCCCCAGCAGGCAGAA
GTATGCAAAGCATGCATCTCAATTAGTCAGCAACCATAGTCCCGCCCCTAAC
TCCGCCCATCCCGCCCCTAACTCCGCCCAGTTCCGCCCATTCTCCGCCCCATG
GCTGACTAATTTTTTTTATTTATGCAGAGGCCGAGGCCGCCTCTGCCTCTGAG
CTATTCCAGAAGTAGTGAGGAGGCTTTTTGGAGGCCTAGGCTTTTGCAAAA
AGCTCCCGGGAGCTTGTATATCCATTTTCGGATCTGATCAGCACGTGTTGACA
ATTAATCATCGGCATAGTATATCGGCATAGTATAATACGACAAGGTGAGGAA
CTAAACCATGGCCAAGTTGACCAGTGCCGTTCCGGTGCTCACCGCGCGCGAC
GTCGCCGGAGCGGTCGAGTTCTGGACCGACCGGCTCGGGTTCTCCCGGGACT
TCGTGGAGGACGACTTCGCCGGTGTGGTCCGGGACGACGTGACCCTGTTCAT
CAGCGCGGTCCAGGACCAGGTGGTGCCGGACAACACCC

Figure 3B

```
TGGCCTGGGTGTGGGTGCGCGGCCTGGACGAGCTGTACGCCGAGTGGTCGGA
GGTCGTGTCCACGAACTTCCGGGACGCCTCCGGGCCGGCCATGACCGAGATC
GGCGAGCAGCCGTGGGGCGGGAGTTCGCCCTGCGCGACCCGGCCGGCAAC
TGCGTGCACTTCGTGGCCGAGGAGCAGGACTGACACGTGCTACGAGATTTCG
ATTCCACCGCCGCCTTCTATGAAAGGTTGGGCTTCGGAATCGTTTTCCGGGAC
GCCGGCTGGATGATCCTCCAGCGCGGGGATCTCATGCTGGAGTTCTTCGCCC
ACCCCAACTTGTTTATTGCAGCTTATAATGGTTACAAATAAAGCAATAGCATC
ACAAATTTCACAAATAAAGCATTTTTTCACTGCATTCTAGTTGTGGTTTGTCC
AAACTCATCAATGTATCTTATCATGTCTGTATACCGTCGACCTCTAGCTAGAG
CTTGGCGTAATCATGGTCATAGCTGTTTCCTGTGTGAAATTGTTATCCGCTCA
CAATTCCACACAACATACGAGCCGGAAGCATAAAGTGTAAAGCCTGGGGTGC
CTAATGAGTGAGCTAACTCACATTAATTGCGTTGCGCTCACTGCCCGCTTTCC
AGTCGGGAAACCTGTCGTGCCAGCTGCATTAATGAATCGGCCAACGCGCGGG
GAGAGGCGGTTTGCGTATTGGGCGCTCTTCCGCTTCCTCGCTCACTGACTCGC
TGCGCTCGGTCGTTCGGCTGCGGCGAGCGGTATCAGCTCACTCAAAGGCGGT
AATACGGTTATCCACAGAATCAGGGGATAACGCAGGAAAGAACATGTGAGC
AAAAGGCCAGCAAAAGGCCAGGAACCGTAAAAAGGCCGCGTTGCTGGCGTT
TTTCCATAGGCTCCGCCCCCTGACGAGCATCACAAAAATCGACGCTCAAGT
CAGAGGTGGCGAAACCCGACAGGACTATAAAGATACCAGGCGTTTCCCCCTG
GAAGCTCCCTCGTGCGCTCTCCTGTTCCGACCCTGCCGCTTACCGGATACCTG
TCCGCCTTTCTCCCTTCGGGAAGCGTGGCGCTTTCTCAATGCTCACGCTGTAG
GTATCTCAGTTCGGTGTAGGTCGTTCGCTCCAAGCTGGGCTGTGTGCACGAAC
CCCCCGTTCAGCCCGACCGCTGCGCCTTATCCGGTAACTATCGTCTTGAGTCC
AACCCGGTAAGACACGACTTATCGCCACTGGCAGCAGCCACTGGTAACAGGA
TTAGCAGAGCGAGGTATGTAGGCGGTGCTACAGAGTTCTTGAAGTGGTGGCC
TAACTACGGCTACACTAGAAGGACAGTATTTGGTATCTGCGCTCTGCTGAAG
CCAGTTACCTTCGGAAAAAGAGTTGGTAGCTCTTGATCCGGCAAACAAACCA
CCGCTGGTAGCGGTGGTTTTTTTGTTTGCAAGCAGCAGATTACGCGCAGAAA
AAAAGGATCTCAAGAAGATCCTTTGATCTTTTCTACGGGGTCTGACGCTCAGT
GGAACGAAAACTCACGTTAAGGGATTTTGGTCATGAGATTATCAAAAAGGAT
CTTCACCTAGATCCTTTTAAATTAAAAATGAAGTTTTAAATCAATCTAAAGTA
TATATGAGTAAACTTGGTCTGACAGTTACCAATGCTTAATCAGTGAGGCACCT
ATCTCAGCGATCTGTCTATTTCGTTCATCCATAGTTGCCTGACTCCCCGTCGTG
TAGATAACTACGATACGGGAGGGCTTACCATCTGGCCCCAGTGCTGCAATGA
TACCGCGAGACCCACGCTCACCGGCTCCAGATTTATCAGCAATAAACCAGCC
AGCCGGAAGGGCCGAGCGCAGAAGTGGTCCTGCAACTTTATCCGCCTCCATC
CAGTCTATTAATTGTTGCCGGGAAGCTAGAGTAAGTAGTTCGCCAGTTAATA
GTTTGCGCAACGTTGTTGCCATTGCTACAGGCATCGTGGTGTCACGCTCGTCG
TTTGGTATGGCTTCATTCAGCTCCGGTTCCCAACGATCAAGGCGAGTTACATG
ATCCCCCATGTTGTGCAAAAAG
```

Figure 3C

CGGTTAGCTCCTTCGGTCCTCCGATCGTTGTCAGAAGTAAGTTGGCCGCAGTG
TTATCACTCATGGTTATGGCAGCACTGCATAATTCTCTTACTGTCATGCCATC
CGTAAGATGCTTTTCTGTGACTGGTGAGTACTCAACCAAGTCATTCTGAGAAT
AGTGTATGCGGCGACCGAGTTGCTCTTGCCCGGCGTCAATACGGGATAATAC
CGCGCCACATAGCAGAACTTTAAAAGTGCTCATCATTGGAAAACGTTCTTCG
GGGCGAAAACTCTCAAGGATCTTACCGCTGTTGAGATCCAGTTCGATGTAAC
CCACTCGTGCACCCAACTGATCTTCAGCATCTTTTACTTTCACCAGCGTTTCTG
GGTGAGCAAAAACAGGAAGGCAAAATGCCGCAAAAAAGGGAATAAGGGCG
ACACGGAAATGTTGAATACTCATACTCTTCCTTTTTCAATATTATTGAAGCAT
TTATCAGGGTTATTGTCTCATGAGCGGATACATATTTGAATGTATTTAGAAAA
ATAAACAAATAGGGGTTCCGCGCACATTTCCCCGAAAAGTGCCACCTGACGT
CGACGGATCGGGAGATCTCCCGATCCCCTATGGTCGACTCTCAGTACAATCT
GCTCTGATGCCGCATAGTTAAGCCAGTATCTGCTCCTGCTTGTGTGTTGGAG
GTCGCTGAGTAGTGCGCGAGCAAAATTTAAGCTACAACAAGGCAAGGCTTGA
CCGACAATTGCATGAAGAATCTGCTTAGGGTTAGGCGTTTTGCGCTGCTTCGC
GATGTACGGGCCAGATATACGCGTTGACATTGATTATTGACTAGTTATTAATA
GTAATCAATTACGGGGTCATTAGTTCATAGCCCATATATGGAGTTCCGCGTTA
CATAACTTACGGTAAATGGCCCGCCTGGCTGACCGCCCAACGACCCCCGCCC
ATTGACGTCAATAATGACGTATGTTCCCATAGTAACGCCAATAGGGACTTTCC
ATTGACGTCAATGGGTGGACTATTTACGGTAAACTGCCCACTTGGCAGTACAT
CAAGTGTATCATATGCCAAGTACGCCCCCTATTGACGTCAATGACGGTAAAT
GGCCCGCCTGGCATTATGCCCAGTACATGACCTTATGGGACTTTCCTACTTGG
CAGTACATCTACGTATTAGTCATCGCTATTACCATGGTGATGCGGTTTTGGCA
GTACATCAATGGGCGTGGATAGCGGTTTGACTCACGGGGATTTCCAAGTCTC
CACCCCATTGACGTCAATGGGAGTTTGTTTTGGCACCAAAATCAACGGGACTT
TCCAAAATGTCGTAACAACTCCGCCCCATTGACGCAAATGGGCGGTAGGCGT
GTACGGTGGGAGGTCTATATAAGCAGAGCTCTCTGGCTAACTAGAGAACCCA
CTGCTTACTGGCTTATCGAAATTAATACGACTCACTATAGGGAGACCCAAGC
ATGGCTAGCGTTTAAACTTAAGCTTGGTACCGAGCTCGGATCCATGCCCATGG
GGTCTCTGCAACCGCTGGCCACCTTGTACCTGCTGGGGATGCTGGTCGCTTCC
GTGCTAGCCACCGAGAAGCTGTGGGTGACCGTGTACTACGGCGTGCCCGTGT
GGAAGGAGGCCACCACCACCCTGTTCTGCGCCAGCGACGCCAAGGCGTACGA
CACCGAGGTGCACAACGTGTGGGCCACCCAGGCGTGCGTGCCCACCGACCCC
AACCCCCAGGAGGTGGAGCTCGTGAACGTGACCGAGAACTTCAACATGTGGA
AGAACAACATGGTGGAGCAGATGCATGAGGACATCATCAGCCTGTGGGACC
AGAGCCTGAAGCCCTGCGTGAAGCTGACCCCCTGTGCGTGACCCTGAACTG
CACCGACCTGAGGAACACCACCAACACCAACAACAGCACCGCCAACAACAA
CAGCAACAGCGAGGGCACCATCAAGGGCGGCGAGATGAAGAACTGCAGCTT
CAACATCACCACCAGCATCCGCGACAAGATGCAGAAGGAGTACGCCCTGCTG
TACAAGCTTGGATATCGTGAGCATCGACAACGAGAGCACCAGCTACCGCTGA

Figure 3D

```
TCTCTTGAACACCAGCGTGATACCCAGGCCTGCCCAAGATCAGNTTCGAGCC
CATCCCAATCACTACTGGCCCCCGCCGGTTTNCNNNNNNNNNNNNNNNNNNN
NNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNN
NNNNNNNNNNNNNNNNNNNNNNNNNNNGCGGCCGCTAAGTAAGTAACTTAAGT
TCCGGTTATTTTCCACCATATTGCCGTCTTTTGGCAATGTGAGGGCCCGGAAA
CCTGGCCCTGTCTTCTTGACGAGCATTCCTAGGGGTCTTTCCCCTCTCGCCAA
AGGAATGCAAGGTCTGTTGAATGTCGTGAAGGAAGCAGTTCCTCTGGAAGCT
TCTTGAAGACAAACAACGTCTGTAGCGACCCTTTGCAGGCAGCGGAACCCCC
CACCTGGCGACAGGTGCCTCTGCGGCCAAAAGCCACGTGTATAAGATACACC
TGCAAAGGCGGCACAACCCCAGTGCCACGTTGTGAGTTGGATAGTTGTGGAA
AGAGTCAAATGGCTCTCCTCAAGCGTATTCAACAAGGGGCTGAAGGATGCCC
AGAAGGTACCCCATTGTATGGGATCTGATCTGGGGCCTCGGTGCACATGCTTT
ACATGTGTTTAGTCGAGGTTAAAAAACGTCTAGGCCCCCCGAACCACGGGGA
CGTGGTTTTCCTTTGAAAAACACGATGATAATATGG
```

METHOD FOR INTRODUCING AND EXPRESSING GENES IN ANIMAL CELLS, AND BACTERIAL BLEBS FOR USE IN SAME

CROSS-REFERENCE TO RELATED APPLICATION

This application is filed under the provisions of 35 U.S.C. §371 and claims the priority of International Patent Application No. PCT/US01/16904 filed on May 24, 2001, published as WO 01/89535, which in turn claims priority of U.S. Provisional Application No. 60/206,994 filed on May 24, 2000.

DESCRIPTION

1. Field of the Invention

The present invention relates to a method for introducing endogenous or foreign genes into animal cells using bacterial blebs as vectors. The method allows for the delivery of eukaryotic expression cassettes encoding the endogenous or foreign genes into animal cells or animal tissue, and is useful for expressing, e.g., vaccine antigens, gene therapeutic agents, immunoregulatory agents, antisense RNAs, and catalytic RNAs, in animal cells or animal tissue.

2. Background of the Invention

I. Live Bacterial Vector Vaccines

The advent of recombinant DNA technology has greatly accelerated the development of vaccines to control epidemic, endemic, and pandemic infectious diseases (Woodrow et al, New Generation Vaccines. The Molecular Approach, Eds., Marcel Dekker, Inc., New York, N.Y. (1989); Cryz, Vaccines and Immunotherapy, Ed., Pergamon Press, New York, N.Y. (1991); and Levine et al, Ped. Ann., 22:719–725 (1993)). In particular, this technology has enabled the growth of a new class of vaccines called bacterial vector vaccines (Curtiss, In: New Generation Vaccines: The Molecular Approach, Ed., Marcel Dekker, Inc., New York, N.Y., pages 161–188 and 269–288 (1989); and Mims et al, In: Medical Microbiology, Eds., Mosby-Year Book Europe Ltd., London (1993)). These vaccines can enter the host orally, intranasally or parenterally. Upon gaining access to the host, the bacterial vector vaccines express an engineered prokaryotic expression cassette contained therein that encodes a foreign antigen(s). Foreign antigens can be any protein (or part of a protein) or combination thereof from a bacterial, viral, or parasitic pathogen that has vaccine properties (New Generation Vaccines: The Molecular Approach, supra; Vaccines and Immunotherapy, supra; Hilleman, Dev. Biol. Stand., 82:3–20 (1994); Formal et al, Infect. Immun., 34:746–751 (1981); Gonzalez et al, J. Infect. Dis., 169:927–931 (1994); Stevenson et al, FEMS Lett., 28:317–320 (1985); Aggarwal et al, J. Exp. Med., 172:1083–1090 (1990); Hone et al, Microbial. Path., 5:407–418 (1988); Flynn et al, Mol. Microbiol., 4:2111–2118 (1990); Walker et al, Infect. Immun., 60:4260–4268 (1992); Cardenas et al, Vacc., 11:126–135 (1993); Curtiss et al, Dev. Biol. Stand., 82:23–33 (1994); Simonet et al, Infect. Immun., 62:863–867 (1994); Charbit et al, Vacc., 1-1:1221–1228 (1993); Turner et al, Infect. Immun., 61:5374–5380 (1993); Schodel et al, Infect. Immun., 62:1669–1676 (1994); Schodel et al, J. Immunol., 145;4317–4321 (1990); Stabel et al, Infect. Immun., 59:2941–2947 (1991); Brown, J. Infect. Dis., 155:86–92 (1987); Doggett et al, Infect. Immun., 61:1859–1866 (1993); Brett et al, Immunol., 80:306–312 (1993); Yang et al, J. Immunol., 145:2281–2285 (1990); Gao et al, Infect. Immun., 60:3780–3789 (1992); and Chatfield et al, Bio/Technology, 10:888–892 (1992)). Delivery of the foreign antigen to the host tissue using bacterial vector vaccines results in host immune responses against the foreign antigen, which provide protection against the pathogen from which the foreign antigen originates (Mims, The Pathogenesis of Infectious Disease, Academic Press, London (1987); and New Generation Vaccines: The Molecular Approach, supra).

Of the bacterial vector vaccines, live oral *Salmonella* vector vaccines have been studied most extensively. There are numerous examples showing that *Salmonella* vectors are capable of eliciting humoral and cellular immunity against bacterial, viral and parasitic antigens (Formal et al, Infect. Immun., 34:746–751 (1981); Gonzalez et al, supra; Stevenson et al, supra; Aggarwal et al, supra; Hone et al, supra; Flynn et al, supra; Walker et al, supra; Cardenas et al, supra; Curtiss et al, supra; Simonet et al, supra; Charbit et al, supra; Turner et al, supra; Schodel et al, supra, Schodel et al (1990), supra; Stabel et al, supra; Brown, supra; Doggett et al, supra; Brett et al, supra; Yang et al, supra; Gao et al, supra; and Chatfield et al, supra). These humoral responses occur in the mucosal (Stevenson et al, supra; Cardenas et al, supra; Walker et al, supra; and Simonet et al, supra), and systemic compartments (Gonzalez et al, supra; Stevenson et al, supra; Aggarwal et al, supra; Hone et al, supra; Flynn et al, supra; Walker et al, supra; Cardenas et al, supra; Curtiss et al, supra; Simonet et al, supra; Charbit et al, supra; Turner et al, supra; Schodel et al, supra; Schodel et al (1990), supra; Stabel et al, supra; Brown, supra; Doggett et al, supra; Brett et al, supra; Yang et al, supra; Gao et al, supra; and Chatfield et al, supra). Live oral *Salmonella* vector vaccines also elicit T cell responses against foreign antigens (Wick et al, Infect. Immun., 62:4542–4548 (1994)). These include antigen-specific cytotoxic $CD8^+$ T cell responses (Gonzalez et al, supra; Aggarwal et al, supra; Flynn et al, supra; Turner et al, supra; and Gao et al, supra).

Ideally, bacterial vector vaccines are genetically defined, attenuated and well-tolerated by the recipient animal or human, and retain immunogenicity (Hone et al, Vacc., 9:810–816 (1991); Tacket et al, Infect. Immun., 60:536–541 (1992); Hone et al, J. Clin. Invest., 90:412–420 (1992); Chatfield et al, Vacc., 10:B-11 (1992); Tacket et al, Vacc., 10:443–446 (1992); and Mims, supra). Recently, the number of potential bacterial vector vaccines for the delivery of prokaryotic expression cassettes has grown. They now include, but are not restricted to, *Yersinia enterocolitica* (van Damme et al, Gastroenterol., 103:520–531 (1992)), *Shigella* spp. (Noriega et al, Infect. Immun., 62:5168–5172 (1994)), *Vibrio cholerae* (Levine et al, In: *Vibrio cholerae*, Molecular to Global Perspectives, Wachsmuth et al, Eds, ASM Press, Washington, D.C., pages 395–414 (1994)), *Mycobacterium* strain BCG (Lagranderie et al, Vacc., 11:1283–1290 (1993); Flynn, Cell. Molec. Biol., 40(Suppl. 1):31–36 (1994)), and *Listeria monocytogenes* (Schafer et al, J. Immunol., 149: 53–59 (1992)) vector vaccines.

II. Bacterial Blebs

During the growth of bacteria small membrane vesicles are produced, which are colloquially called blebs (Dorward et al., J. Bacteriol., 171:2499 (1989)). Bacteria that make blebs include but are not limited to *Agrobacterium* spp., *Bacillus* spp., *Borrelia* spp., *Bordetella* spp., *Calymmatobacterium* spp., *Escherichia* spp., *Haemophilus* spp., *Neisseria* spp., *Pseudomonas* spp., *Porphyromonas* spp., *Fusobacterium* spp., *Rhodococcus* spp., *Salmonella* spp., *Serratia* spp., *Shigella* spp., and *Yersinia* spp. (Dorward and Garon, Appl, Environ. Microbiol., 56:1960 (1990); Karow et al, J. Bact., 173:741–750 (1991); Karow and Georgopoulos, J. Bact., 174:702–710 (1992); Begg and Donachie, J. Bact., 163:615–622 (1985); Radolf et al, J. Bact., 176.21–31 (1994); Whitmire and Garon, Infect. Immun., 61:1460–1467 (1993); Garcia et al, Canad. J. Vet. Res., 56:318–325 (1992);, and Chandra and Jain, Ind. J. Med. Res., 93:225–231 (1991). The envelope of bacterial blebs can be composed of outer membrane, inner membrane or a combination of both (Dorward et al, supra). The latter are more correctly called mini-cells (Adler et al., Proc. Natl. Acad. Sci., USA, 5–7:321–326 (1967); and de Boer et al, Cell, 56:641–649 (1989)). Each of these fractions can be isolated by differential centrifugation followed by sucrose or cesium chloride density gradient centrifugation (Dorward et al., supra). Some bacterial strains are naturally high producers of blebs (Dorward and Garon, supra). However, certain mutations that result in defective cell wall synthesis increase the frequency of bleb formation in strains that are low producers of blebs (Adler et al., supra; de Boer et al, supra; Karow et al, supra; Karow and Georgopoulos, supra; and Begg and Donachie, supra). Blebs can also be produced artificially by physical disruption methods such as sonication of bacterial cells or passing bacteria through a French pressure cell (Morein et al, Anal. Biochem., 216:47–51 (1994)); or by treatment of bacterial cells with bacteriocidal or bacteriostatic chemicals (Kadurugamuwa et al, J. Bact., 175:5798–5805 (1993); and Dargis et al, Infect. Immun., 60:4024–4031 (1992)).

Blebs can contain bacterial chromosomal and/or plasmid DNA (Dorward and Garon, supra). It is not clear how the DNA becomes associated with the blebs. Interestingly, blebs have been shown to transfer plasmid DNA within a bacterial species (Dorward et al., supra). This phenomenon has been proposed as a alternative method of genetic exchange between bacteria (Dorward et al., supra); Holloway, Ann. Rev. Microbiol., 47:659 (1993); Dreiseikehnann, Microbiol. Rev., 58:293 (1994)).

III. Eukaryotic and Prokaryotic

Expression Cassettes

Normally, an expression cassette is composed of a promoter region, a transcriptional initiation site, a ribosome binding site (RBS), an open reading frame (orf) encoding a protein (or fragment thereof), with or without sites for RNA splicing (only in eukaryotes), a translational stop codon, a transcriptional terminator and post-transcriptional poly-adenosine processing sites (Wormington, Curr. Opin. Cell Biol., 5:950–954 (1993); Reznikoff et al, Maximizing Gene Expression, Eds., Butterworths, Stoneham, Mass. (1986). The promoter region, the RBS, the splicing sites, the transcriptional terminator and post-transcriptional poly-adenosine processing sites are markedly different in eukaryotic expression cassettes than those found in prokaryotic expression cassettes (Wasylyk, In: Maximizing Gene Expression, supra, pages 79–99; Reznikoff et al, In: Maximizing Gene Expression, supra, pages 1–34; and Lewin, Genes V, Oxford University Press, Oxford (1994)). These differences prevent expression of prokaryotic expression cassettes in eukaryotic cells and visa versa (Miller et al, Mol. Micro., 4:881–893 (1990); and Williamson et al, Appl. Env. Micro., 60:771–776 (1994)).

Prokaryotic promoters are not active in eukaryotic cells and eukaryotic promoters are not active in prokaryotic cells (Eick et al, Trends in Genetics, 10:292–296 (1994)). The basis for the functional diversity of eukaryotic versus prokaryotic promoters is mediated by RNA-polymerase, transcription regulatory factors and the DNA structure of the promoter (Eick et al, supra).

RNA polymerases are DNA-binding proteins that recognize specific sequences in the DNA of promoter regions. RNA polymerases catalyze the synthesis of RNA molecules by polymerizing nucleoside triphosphates in the specific order that is dictated by the DNA coding sequence (Libby et al, Mol. Micro., 5:999–1004 (1991) Kerppola et al, FASEB J., 5:2833–2842 (1991); Alberts et al, Molecular Biology of the Cell, Eds., Garland Publishing Inc., New York, N.Y. (1994); Watson et al, Molecular Biology of the Gene, Vol. 1, Eds., The Benjamin/Cummings Publishing Comp. Inc., Menlo Park Calif. (1987); and Lewin, supra). RNA polymerases of prokaryotes typically are composed of two identical a subunits and two similar, but non-identical, $\beta$ and $\beta'$, subunits (Ishihama, Mol. Micro., 6:3283–3288 (1992); Watson et al, supra; Alberts et al, supra; and Lewin, supra). The specificity of prokaryotic RNA polymerases for a given promoter region is mediated by specific s factors that recognize core sequences encoded by the DNA in the promoter regions (Libby et al, supra; and Lewin, supra).

In eukaryotic cells, there are three RNA polymerases. Each of the different RNA polymerases contain 10 to 15 different subunits and each performs a different function (Kerppola et al, supra; Larson et al, Biochem. Cell. Biol., 69:5–22 (1991); Archambault et al, Microbiol. Rev., 57:703–724 (1993); Watson et al, supra; Alberts et al, supra; and Lewin, supra). In addition, specific DNA-binding factors may be required for the association of eukaryotic RNA polymerases to the DNA in a promoter region (Darnell et al, Molecular Cell Biology, Scientific American Books, Inc., W.H. Freeman and Co., New York, N.Y. (1990); Hori et al, Curr. Opin. Gen. Devel., 4:236–244 (1994); Lewin, supra; Watson et al, supra; and Alberts et al, supra). These binding factors recognize specific sequences in the DNA, and also interact with the eukaryotic RNA polymerases.

There is little similarity between the primary DNA sequence of prokaryotic promoters and the primary DNA sequence of eukaryotic promoters. The DNA structure of prokaryotic promoters is relatively simple, consisting of –10 and –35 regions and proximal regulatory sequences (Darnell et al, supra; Lewin, supra; Watson et al, supra; and Alberts et al, supra). Prokaryotic promoters are located upstream of the transcription start site. Eukaryotic promoters, in contrast, are composed of a core unit, which is usually located from 50 bp upstream to 20 bp downstream of the transcriptional start site (Darnell et al, supra; Lewin, supra; Watson et al, supra; and Alberts et al, supra), and enhancer sequences that are located from about 100 to 200 bp upstream of the transcriptional start, but also can be located in distal locations (Sonenberg, Curr. Opin. Gen. Devel., 4:310–315 (1994); Geballe et al, Trends Bio. Sci., 1:159–164 (1994); and Lewin, supra).

The RBS is the site recognized by the ribosome for binding to the 5' end of messenger RNA (mRNA) molecules. This binding is essential for the translation of mRNA into a protein by the ribosome. In prokaryotes, the RBS in the 5' end of the mRNA molecule is a sequence that is complementary to the 3' end of the small ribosomal RNA molecule (5S rRNA) (Chatterji et al, Ind. J. Biochem. Biophys., 29:128–134 (1992); and Darnell et al, supra; Lewin, supra; Watson et al, supra; and Watson et al, supra). The presence of the RBS promotes binding of the ribosome to the 5' end of the nascent mRNA molecule. Translation is then initiated at the first AUG codon encountered by the scanning ribosome (Darnell et al, supra; Lewin, supra; Watson et al, supra;

and Alberts et al, supra). At present, no such recognition pattern has been observed in eukaryotic mRNA-ribosome interactions (Eick et al, supra). In addition, prior to initiation of translation of eukaryotic mRNA, the 5' end of the mRNA molecule is "capped" by addition of methylated guanylate to the first mRNA nucleotide residue Darnell et al, supra; Lewin, supra; Watson et al, supra; and Alberts et al, supra). It has been proposed that recognition of the translational start site in mRNA by the eukaryotic ribosomes involves recognition of the cap, followed by binding to specific sequences surrounding the initiation codon on the mRNA. It is possible for cap independent translation initiation to occur and/or to place multiple eukaryotic coding sequences within a eukaryotic expression cassette if a cap-independent translation enhancer (CITE) sequence, such as derived from encephalomyocarditis virus (Duke et al., J. Virol., 66:1602–1609 (1992)), is included prior to cr between the coding regions (Morgan et al., Nuc. Acids Res., 20:1293–1299 (1992)). However, the initiating AUG codon is not necessarily the first AUG codon encountered by the ribosome (Louis et al, Molec. Biol. Rep., 13:103–115 (1988); and Voorma et al, Molec. Biol. Rep., 19:139–145 (1994); Lewin, supra; Watson et al, supra; and Alberts et al, supra). Thus, RBS binding sequences in eukaryotes are sufficiently divergent from that of prokaryotic RBS such that the two are not interchangeable.

Termination of transcription in prokaryotes is mediated by rho-independent and rho-dependent stem loops (Richardson, Crit. Rev. Biochem. Mol. Biol., 28:1–30 (1993); Platt, Molec. Microbiol., 11:983–990 (1994); and Lewin, supra). In contrast, terminator loops are not commonly found downstream of eukaryotic expression cassettes, and transcription often extends beyond the end of the open reading frame (Tuite et al, Mol. Biol. Reps., 19:171–181 (1994). However, usually the over-extended mRNA is specifically cleaved by endonucleases, and the 3' end of the mRNA is poly-adenylated by poly-A polymerase (Proudfoot, Cell, 64:671–674 (1991); Wahle, Bioassays, 14:113–118 (1992); Lewin, supra; and Watson et al, supra). Sequences that are recognized by the endonucleases and poly-A polymerase must be included in the 3' end of the mRNA molecule for these post-translation modifications to occur. Polyadenylation of the 3' end of mRNA molecules is thought to be a necessary step prior to transport of mRNA to the cytoplasm of eukaryotic cells and translation into proteins (Sachs et al, J. Biol. Chem., 268:22955–22958 (1993); and Sachs, Cell, 74-413–421 (1993)). A eukaryotic expression cassette does not need to code for a functional gene product, i.e., it may also code for a partial gene product which acts as an inhibitor of a eukaryotic enzyme (Warne et al, Nat., 364: 352–355 (1993); and Wang, J. Cell Biochem., 45:49–53 (1991)), an antisense RNA (Magrath; Ann. Oncol., 5(Suppl 1):67–70 (1994); Milligan et al, Ann. NY Acad. Sci., 716: 228–241 (1994); and, Schreier, Pharma. Acta Helv., 68:145–159 (1994)), a catalytic RNA (Cech, Biochem. Soc. Trans., 21:229–234 (1993); Cech, Gene, 135:33–36 (1993); Long et al, FASEB J., 7:25–30; and Rosi et al, Pharm. Therap., 50:245–254 (1991)), or any other sequence which can be transcribed into RNA.

Due to a need for eukaryotic expression cassettes to study the biology of eukaryotic cells, a number of eukaryotic expression plasmids are now readily available. These include, but are not limited to, commercial products from companies such as Invitrogen Corporation (San Diego, Calif.), Stratagene (La Jolla, Calif.), ClonTech (Palo Alto, Calif.) and Promega Corporation Madison, Wis.). All of these plasmids contain the elements of a eukaryotic expression cassette listed above, and many also contain a prokaryotic promoter sequence such that the gene placed downstream from the promoter sequences will be expressed in a prokaryotic as well as in a eukaryotic cell, e.g., plasmid pSVβ-gal contains the eukaryotic SV40 promoter and the prokaryotic gpt promoter which allows for the expression of the β-galactosidase gene in either prokaryotic cells or eukaryotic cells (Promega Corp.).

III. Commercial Applications for the Delivery of Eukaryote Expression Cassettes to Animal Cells The commercial applications of DNA delivery technology to animal cells are extremely broad and includes delivery of vaccine antigens (Fynan et al, Proc. Natl. Acad. Sci., USA, 90:11478–11482 (1993); Katsumi et al, Hum Gene Ther, 5(11);1335–1339 (1994); and Spooner et al, Int J. Oncol, 6(6):1203–1208 (1995)), immunotherapeutic agents (Shillitoe et al, Eur J Cancer 30B(3):143–154 (1994); Hengge et al, Nature Genetics, 10(2):161–166 (1995); Vile and Hart, Ann Oncol, 5(Suppl 4):59–65 (1994); Miller et al, Ann Surg Oncol, 1(5):436–450 (1994); and Foa, Baillieres Clin Haematol, 7(2):421–434 (1994)), and gene therapeutic agents (Darris et al, Canc., 74(3 Suppl.):1021–1025 (1994); Magrath, Ann. Oncol., 5(Suppl 1):67–70 (1994); Milligan et al, Ann. NY Acad. Sci., 716:228–241 (1994); Schreier, Pharma Acta Helv., 68:145–159 (1994); Cech, Biochem. Soc. Trans., 21:229–234 (1993); Cech, Gene, 135:33–36 (1993); Long et al, FASEB J., 7:25–30 (1993); Dropulic and Jeang, Hum. Gene. Ther., 5:927–939 (1994); Sorscher et al, Hum. Gene. Ther., 5:1259–1277 (1994); Long et al, FASEB J., 7:25–30 (1993); Nabel et al, Hum. Gene. Ther. 5:89–109 (1994); Manthorpe et al, Hum. Gene. Ther., 4:419–431 (1993); Mittal et al, Virus Res., 28:67–90 (1993); Setoguchi et al, Am. J. Resp. Cell Mol. Biol., 10:369–377 (1994); and Rosi et al, Pharm. Therap., 50:245–254 (1991)).

Significant efforts have been directed to delivery of eukaryotic expression cassettes to animal tissue for gene therapy (Nabel, Circulation, 91:541–548 (1995); Coovert et al, Curr. Opin. Neuro., 7:463–470 (1994); Foa, Biol. Clin. Haemat., 7:421–434 (1994) Bowers et al, J. Am. Diet. Assoc., 95:53–59 (1995); Perales et al, Eur. J. Biochem., 226:255–266 (1994); Danko et al, Vacc., 12:1499–1502 (1994); Conry et al, Canc. Res., 54:1164–1168(1994); Ledley, Clin. Invest. Med., 16:78–88 (1993); and Smith, J. Hemat., 1:155–166 (1992)). Gene therapy strategies include genetic complementation of genetic disorders (Caplen et al., Nat. Med., 1:39–46 (1995)), expression of antisense mRNA that specifically blocks the expression of viral genes (Dropulic and Jeang, Hum. Gene Thera., 5:927–939 (1994); Tung and Daniel, Arch. Virol., 133:407–421 (1993)), ocogenes (Fujiwara et al, Curr. Opin. Oncol., 6:96–105 (1994); and Milligan et al, Annal. New York Acad. Sci., 716: 228–241 (1994) autoimmune antigens (Steinhoff et al, Proc. Natl. Acad. Sci., USA, 91:5085–5088 (1994) and expression of enzymatically active RNA species to modulate the expression of genes (Altman, Proc. Natl. Acad. Sci., USA, 90:10898–10900 (1993); and Sullivan, J. Invest. Dermatol., 103 (5 Suppl.):85–89 (1994)).

Significant efforts also have been directed to delivery of eukaryotic expression cassettes to animal tissue for immunotherapy (Pappo et al. J. Surg. Res., 58:218–226 (1995)). Applications in this field include expression of immunoregulatory molecules such as growth factors or cytokines for tumor therapy (Pardoll, Curr. Opin. Oncol., 4:1124–1129 (1992a); Pardoll, Curr. Opin. Immunol., 4:619–623 (1992b)), expression of tumor-specific antigens for the induction of anti-tumor immunity (Koeppen et al, Anal. N.Y.

Acad. Sci., 690:244–255 (1993); and Conry et al., Gene Ther., 2:59–65 (1995)), and delivery of genetic elements that specifically down-regulate host rejection response prior to and following tissue transplantation (Qin et al., Annal. Surg., 220:518–519 (1994)).

"Naked" or polynucleotide DNA vaccines encoding eukaryotic expression cassettes have been used to successfully immunize against influenza both in chickens (Robinson et al, supra) and ferrets (Webster et al, Vacc., 12:1495–1498 (1994)); against *Plasmodium yoelii* in mice (Hoffman et al, supra); against rabies in mice (Xiang et al, supra); against human carcinoembryonic antigen in mice (Conry et al, supra) and against hepatitis B in mice (Davis et al, supra).

IV. Delivery of Eukaryotic Expression Cassettes to Plant Cells

The use of *Agrobacterium tumerfacium* Ti plasmid to stably deliver DNA to plant cells has been a fundamental advance in plant biotechnology. This system is unique in that it uses a pilus-like structure which binds to the plant cell via specific receptors, and then through a process that resembles bacterial conjugation, delivers the Ti plasmid-linked DNA to the plant cell (Zambryski, Ann. Rev. Genet., 22:1–30 (1988); Lessl et al, Call, 77:321–324 (1994); and Walden et al, Eur. J. Biochem., 192:563–576 (1990)). The specificity of this delivery system for plants, however, renders it ineffective for delivery of DNA to animal cells (Chilton, Proc. Natl. Acad. Sci., USA, 90:3119–3120 (1993); and Walden et al, supra).

V. Delivery of Eukaryotic Expression Casettes to Animal Cells in Vitro

There are several techniques for introducing DNA into animal cells cultured in vitro. These include the use of cationic liposomes (Hawley-Nelson et al, Focus, 15:73–79 (1993); Ciccarone et al, Focus, 15:80–83 (1993); Pinnaduwage et al, Biochim. Biophys. Acta, 985:33–37 (1989); Felgner et al, Proc. Natl. Acad. Sci., USA, 84:7413–7417 (1987); Hug and Sleight, Biochim. Biophys. Acta, 1097:1–17 (1991)), chemical methods (Felgner et al, supra; Bothwell et al, Methods for Cloning and Analysis of Eukaryotic Genes, Eds, Jones and Bartlett Publishers Inc., Boston, Mass. (1990), Ausubel et al, Short Protocols in Molecular Biology, John Wiley and Sons, New York, N.Y. (1992); and Farhood, Annal. N.Y. Acad. Sci., 716:23–34 (1994)), use of protoplasts (Bothwell, supra) electrical pulses (Vatteroni et al, Mutn. Res., 291:163–169 (1993); Sabelnikov, Prog. Biophys. Mol. Biol., 62:119–152 (1994); Brothwell et al, supra; and Ausubel et al, supra), use of attenuated viruses (Morgan et al., supra); Moss, Dev. Biol. Stan., 82:55–63 (1994); and Brothwell et al, supra), and physical methods (Fynan et al, supra; Johnston et al, Meth. Cell Biol, 43 (Pt A):353–365 (1994); Brothwell et al, supra; and Ausubel et al, supra).

VII. Techniques for the Introduction of Eukaryotic Expression Cassettes into Animal Cells in Vivo Successful delivery of eukaryotic expression cassettes to animal tissue has been achieved by cationic liposomes (Hazinski et al., Am. J. Resp. Cell Molec. Biol., 4:206–209 (1991); Yoshimura et al., Nuc. Acid Res., 20:3233–3240 (1992); San et al, Hum. Gene Ther., 4:781–788 (1993); Stewart et al, Hum. Gene Ther., 3:267–275 (1992); Nabel et al, Proc. Natl. Acad. Sci., USA, 90:11307–11311 (1993); Watanabe et al, Mol. Reprod. Dev., 38:268–274 (1994)), avirulant viral delivery vectors such as the retroviral (Belmont et al, Nat., 322:385–387 (1986); Plautz et al., New Biologist, 3:709–715 (1991); Woolf et al., Kidn. Int., 39:S116–119 (1993); Melani et al., Nat. Immun., 13:76–84 (1994); and Kolodka et al., Proc. Natl. Acad. Sci., USA, 92:3293–3297 (1995)) and adenoviral (Engelhardt et al., Nat. Genet., 4:27–34 (1993); Mastrangeli et al., J. Clin. Invest., 91:225–234 (1993); Bajocchi et al., Nat. Genet., 3:229–234 (1993); Curiel, Nat. Immun., 13:141–164 (1994); Morris et al., J. Urol., 152:506–509 (1994); and Zabner et al., Nat. Genet., 6:75–83 (1994)) delivery systems, direct injection of "naked" DNA into animal muscle tissue or subcutaneously (Robinson et al, Vacc., 11:957–960 (1993); Hoffman et al, Vacc., 12:1529–1533; (1994); xiang et al, Virol., 199:132–140 (1994); Webster et al, Vacc., 12:1495–1498 (1994); Davis et al, Vacc., 12:1503–1509 (1994); and Davis et al, Hum. Molec. Gen., 2:1847–1851 (1993)), and embryos (Naito et al, Mol. Reprod. Dev., 39:153–161 (1994); and Burdon et al, Mol. Reprod. Dev., 33:436–442 (1992)), and intradermal injection of DNA using "gene gun" technology (Johnston et al, supra).

VIII. Summary

There is a need in the art for an efficient means for delivering eukaryotic expression cassettes including endogenous and/or foreign genes, encoding vaccine, gene therapeutic, or immunotherapeutic agents, to animal cells or tissue.

The present invention describes a novel and unexpected finding that bacterial blebs are capable of delivering eukaryotic expression cassettes to animal cells. An important aspect of using bacterial blebs to deliver eukaryotic expression cassettes is that they are capable of delivering DNA to mucosal sites.

Heretofore, there has been no documented demonstration of bacterial blebs for introducing eukaryotic expression cassettes, which then are expressed by the treated cells and progeny thereof. That is, the present invention provides the first documentation of genetic exchange between bacterial blebs and animal cells. Heretofore, foreign antigen delivery by live bacterial vector vaccines merely involved delivery of prokaryotic expression cassettes to and expression of the foreign antigen by the bacterial vaccine vector, in animal cells or tissues. In contrast, the present invention involves the delivery of eukaryotic expression cassettes by bacterial blebs to animal cells in vitro or to cells in animal tissue, and expression of the eukaryotic expression cassettes by the animal cell or cells in animal tissue.

SUMMARY OF THE INVENTION

One object of the present invention is to use bacterial blebs to deliver one or more eukaryotic expression cassettes to animal cells or animal tissue.

Another object of the present invention is to use bacterial blebs to deliver one or more eukaryotic expression cassettes encoding vaccine antigen(s) to animal cells or animal tissue.

Another object of the present invention is to use bacterial blebs to deliver one or more eukaryotic expression cassettes encoding gene therapeutic agents to animal cells or animal tissue.

Another object of the present invention is to use bacterial blebs to deliver one or more eukaryotic expression cassettes encoding immunoregulatory agents to animal cells or animal tissue.

Yet another object of the present invention is to use bacterial blebs to deliver one or more eukaryotic expression cassettes encoding biologically active RNA species to animal cells or animal tissue.

In one aspect, the invention relates to a method for introducing and expressing a gene in animal cells, comprising infecting said animal cells with bacterial blebs, wherein the bacterial blebs contain a eukaryotic expression cassette including such gene.

In another aspect, the present invention relates to bacterial blebs, which contain one or more eukaryotic expression cassettes including an endogenous or foreign gene.

Other aspects, features, objects and embodiments of the present invention will be more fully apparent from the ensuing detailed description of the invention.

BRIEF DESCRIPTION OF THE FIGURES

FIGS. 3A, B, C and D show the nucleotide sequence (SEQ ID NO: 1) for plasmid pOGL1-A1 expresses the 120 kDA glycoprotein (i.e. gp120) of human immunodeficiency virus type 1 (HIV-1) and the A1 subunit of cholera toxin (i.e. CtxA1).

DETAILED DESCRIPTION OF THE INVENTION

Figure 1:
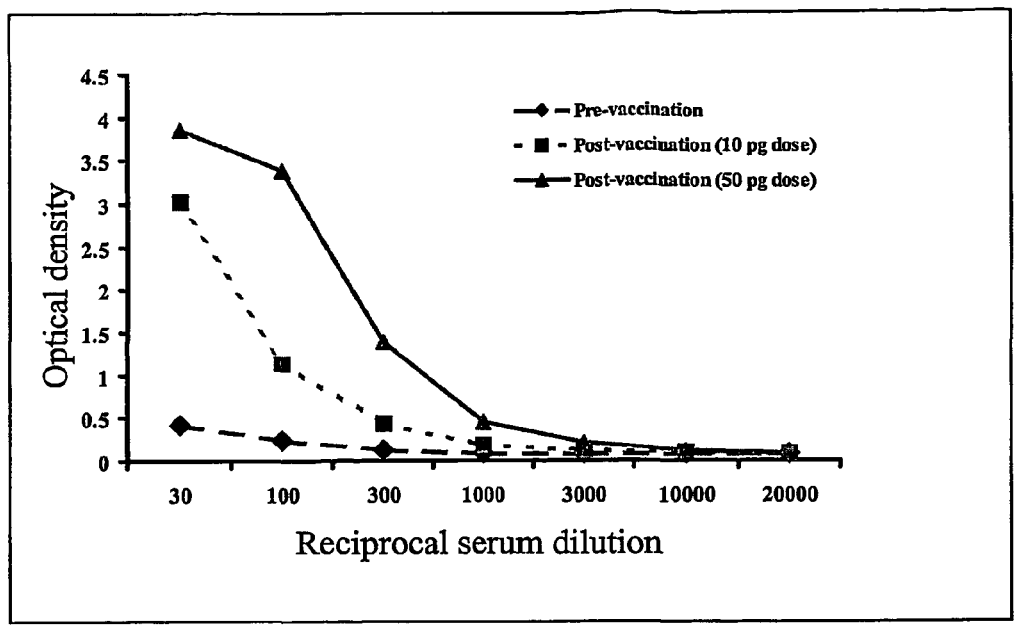
FIG. 1 shows the results of the ELISA showing that vaccination of mice with a single dose of the non-pyrogenic Salmonella Blebs induced a strong serum IgG response against Salmonella.

The disclosure of U.S. Provisional Patent Application No. 60/206,994 filed May 24, 2000 in the names of Robert J. Powell and David M. Hone for "Method for Inducing Nucleic Acids into Cells Using Bacterial Blebs as Vectors," is hereby incorporated herein by reference in its entirety.

The present invention in one aspect relates to a method for introducing and expressing a gene in animal cells comprising treating said animal cells with bacterial blebs, wherein the bacterial blebs contain a eukaryotic expression cassette encoding the gene.

Animal cells are defined as nucleated, non-chloroplast containing cells derived from or present in multicellular organisms whose taxonomic position lies within the kingdom animalia. The cells may be present in the intact animal, a primary cell culture, explant culture or a transformed cell line. The particular tissue source of the cells is not critical to the present invention.

The recipient animal cells employed in the present invention are not critical thereto and include cells present in or derived from all organisms within the kingdom animalia, such as those of the families mammalia, pisces, avian, reptilia.

Preferred animal cells are mammalian cells, such as humans, bovine, ovine, porcine, feline, buffalo, canine, goat, equine, donkey, deer, and primate cells. The most preferred animal cells are human cells.

Examples of transformed human cell lines include but are not limited to ATCC Nos. CCL 62, CCL 159, HTB 151, HTB 22, CCL 2, CRL 1634, CRL 8155, HTE 61, and HTBIO4.

Examples of transformed bovine cell lines include ATCC Nos. CRL 6021, CRL 1733, CRL 6033, CRL 6023, CCL 44 and CRL 1390.

Examples of transformed ovine cells lines include ATCC Nos. CRL 6540, CRL 6538, CRL6548 and CRL6546.

Examples of transformed porcine cell lines include ATCC Nos. CL 184, CRL 6492, and CRL 1746.

Examples of transformed feline cell lines include CRL 6077, CRL 6113, CRL 6140, CRL 6164, CCL 94, CCL 150, CRL 6075 and CRL 6123.

Examples of transformed buffalo cell lines include CCL 40 and CRL 6072.

Examples of transformed canine cells include ATCC Nos. CRL 6213, CCL 34, CRL 6202, CRL 6225, CRL 6215, CRL 6203 and CRL 6575.

Examples of transformed goat derived cell lines include ATCC No. CCL 73 and ATCC No. CRL 6270.

Examples of transformed horse derived cell lines include ATCC Nos. CCL 57 and CRL 6583.

Examples of transformed deer cell lines include ATCC Nos. CRL 6193-6196.

Examples of transformed primate derived cell lines include those from chimpanzees such as ATCC Nos. CRL 6312, CRL 6304, and CRL 1868; monkey cell lines such as ATCC Nos. CRL 1576, CCL 26, and CCL 161; orangutan cell line ATCC No. CRL 1850; and gorilla cell line ATCC No. CRL 1854.

As used herein, "bacterial blebs" are bacterial membrane-bound vesicles that are capable of delivering eukaryotic expression cassettes to animal cells or animal tissue. "Bacterial blebs" are produced by a number of different bacterial generi including bacteria that are naturally capable of entering the animal cells, as well as bacteria that are not capable of entering animal cells or cells in animal tissue (Dorward and Garon, supra).

The particular naturally occurring bleb-producing bacteria employed in the practice of the present invention is not critical thereto. Examples of such naturally occurring bleb-producing bacteria include, but are not limited to, Shigella spp., Salmonella spp., Nisseria spp., Haemophilus spp. and Escherichia spp.

Concerning the use of Shigella spp. as a bleb-producing bacterium, the particular Shigella strain employed is not critical to the practice of the present invention. Examples of Shigella strains that can be employed in the present invention include Shigella flexneri 2a (ATCC No. 29903), Shigella sonnei (ATCC No. 29930), and Shigella disenteriae (ATCC No. 13313). An attenuated Shigella strain, such as Shigella flexneri 2a 2457T ΔaroAΔvirG mutant CVD 1203 (Noriega et al, supra), Shigella flexneri M90T ΔicsA mutant (Goldberg et al, Infect. Immun., 62:5664–5668 (1994)), Shigella flexneri Y SFL114 aroD mutant (Karnell et al, Vacc., 10:167–174 (1992) and Shigella flexneri ΔaroAΔaroD mutant (Verma et, al, Vacc., 9:6–9 (1991)), is preferably employed. Alternatively, new attenuated Shigella spp. strains can be constructed by introducing an attenuating mutation either singularly or in conjunction with one or more additional attenuating mutations.

Attenuating mutations can be introduced into bacterial pathogens using non-specific mutagenesis either chemically, using agents such as N-methyl-N'-nitro-N-nitrosoguanidine, or using recombinant DNA techniques; classic genetic techniques, such as Tn10 mutagenesis, P22-mediated transduction, λ phage mediated crossover, and conjugational transfer; or site-directed mutagenesis using recombinant DNA techniques. Recombinant DNA techniques are preferable since strains constructed by recombinant DNA techniques are far more defined. Examples of such attenuating mutations include, but are not limited to:

(i) auxotrophic mutations, such as aro (Hioiseth et al, Nat., 291:238–239 (1981)), gua (McFarland et al, Microbiol. Path., 3:129–141 (1987)), nad (Park et al, J.

Bact., 170:3725–3730 (1988), thy (Nnalue et al, Infect. Immun., 55:955–962 (1987)), and asd (Curtiss, supra) mutations;

(ii) mutations that inactivate global regulatory functions, such as cya (Curtiss et al, Infect. Immun., 55:3035–3043 (1987)), crp (Curtiss et al (1987), supra), phoP/phoQ (Groisman et al, Proc. Natl. Acad. Sci., USA, 86:7077–7081 (1989); and Miller et al, Proc. Natl. Acad. Sci., USA, 86:5054–5058 (1989)), phoP$^c$ (Miller et al, J. Bact., 172:2485–2490 (1990)) or ompR (Dorman et al, Infect. Inmun., 57:2136–2140 (1989)) mutations;

(iii) mutations that modify the stress response, such as recA (Buchmeier et al, Mol. Micro., 7:933–936 (1993)), htrA (Johnson et al, Mol. Micro. 5;401–407 (1991)), htpR (Neidhardt et al, Biochem. Biophys. Res. Com., 100:894–900 (1981)), hsp (Neidhardt et al, Ann. Rev. Genet., 18:295–329 (1984)) and groEL (Buchmeier et al, Sci., 248:730–732 (1990)) mutations;

(iv) mutations in specific virulence factors, such as lsyA (Libby et al, Proc. Natl. Acad. Sci., USA, 91:489–493 (1994)), pag or prg (Miller et al (1990), supra; and Miller et al (1989), supra), iscA or virG (d'Hauteville et al, Mol. Micro., 6:833–841 (1992)), picA (Mengaud et al, Mol. Microbiol., 5:367–72 (1991); Camilli et al, J. Exp. Med., 173:751–754 (1991)), and act (Brundage et al, Proc. Natl. Acad. Sci., USA, 90:11890–11894 (1993)) mutations;

(v) mutations that affect DNA topology, such as topA (Galan et al, Infect. Immun., 58:1879–1885 (1990)) mutation;

(vi) mutations that modify or block biogenesis of surface polysaccharides, such as htrB (Karow et al, J. Bact., 173:741–750 (1991)), rfb or, galE (Hone et al, J. Infect. Dis., 156:164–167 (1987) or via (Popoff et al, J. Gen. Microbiol., 138:297–304 (1992)) mutations;

(vii) mutations that modify suicide systems, such as sacB (Recorbet et al, App. Environ. Micro., 59:1361–1366 (1993); Quandt et al, Gene, 127:15–21 (1993)), nuc (Ahrenholtz et al, App. Environ. Micro., 60:3746–3751 (1994)), hok, gef, kil, or phlA (Molin et al, Ann. Rev. Microbiol., 47:139–166 (1993)) mutations;

(viii) mutations that introduce suicide systems, such as lysogens encoded by P22 (Rennell et al, Virol., 143: 280–289 (1985)), λ murein transglycosylase (Bienkowska-Szewczyk et al, Mol. Gen. Genet:., 184:111–114 (1981)) or S— gene (Reader et al, Vi rol., 43:623–628 (1971)); and (ix) mutations that disrupt or modify the correct cell cycle, such as minb (de Boer et al, supra) mutation.

The attenuating mutations can be either constitutively expressed or under the control of inducible promoters, such as the temperature sensitive heat shock family of promoters (Neidhardt et al, supra), or the anaerobically induced nirB promoter (Harbome et al, Mol. Micro., 6:2805–2813 (1992)) or repressible promoters, such as uapA (Gorfinkiel et al, J. Biol. Chem., 268:23376–23381 (1993)) or gcv (Stauffer et al, J. Bact., 176:6159–6164 (1994)).

With respect to use of *Salmonella* spp. as the bleb-producing bacterium, the particular *Salmonella* strain employed is not critical to the practice of the present invention. Examples of *Salmonella* strains that can be employed in the present invention include *Salmonella typhi* (ATCC No. 7251) and *S. typhimurium* (ATCC No. 13311). Attenuated *Salmonella* strains are preferably used in the practice of the present invention and include *S. typhi* ΔaroAΔaroD (Hone et al, Vacc., 9:810–916 (1991)) and *S. typhimurium* aroA mutant (Mastroeni et al, Micro. Pathol., 13:477–491 (1992)). Alteratively, new attenuated *Salmonella* strains can be constructed by introducing one or more attenuating mutations as described for *Shigella* spp. above.

Concerning the use of *Neisseria* spp. as the bleb-producing bacterium, the particular *Neisseria* strain employed is not critical in the broad practice of the present invention. Examples of *Neisseria* strains that can be employed in the present invention include *N. meningitides* (ATCC No. 13077) and *N. gonorrhoeae* (ATCC No. 19424). Attenuated *Neisseria* strains, such as *N. gonorrhoeae* MS11 aro mutant (Chamberlain et al, Micro. Path., 15:51–63 (1993)) are preferably used in the practice of the present invention. Alternatively, new attenuated *Neisseria* strains can be constructed by introducing one or more attenuating mutations as described for *Shigella* spp. above.

In respect of the use of *Haemophilus* spp. as the bleb-producing bacterium, the particular *Hemophilus* strain employed is not critical in the broad practice of the present invention. Examples of *Hemophilus* strains that can be employed in the practice of the present invention include *H. sornnus* (ATCC No. 43625). Attenuated *Hemophilus* strains are preferably used in the practice of the present invention, and can be constructed by introducing one or more attenuating mutations as described for *Shigella* spp. above.

Concerning use of *Escherichia* spp. as the bleb-producing bacterium, the particular *Escherichia* strain employed is not critical in the broad practice of the present invention. Examples of *Escherichia* strains that can be employed in the practice of the present invention include *Escherichia coli* strains 4608-58, 1184-68, 53638-C-17, 13–80, and 6–81 (Sansonetti et al, Ann. Microbiol. (Inst. Pasteur), 132A: 351–355 (1982)), *E. coli* H10407 (Elinghorst et al, Infect. Immun., 60:2409–2417 (1992)), and *E. coli* EFC4, CFT325 and CPZ005 (Dornenberg et al, J. Infect. Dis., 169:831–838 (1994)). Attenuated *Escherichia* strains, such as the attenuated turkey pathogen *E. coli* 02 carAB mutant (Kwaga et al, Infect. Immun., 62:3766–3772 (1994)) are preferably used in the practice of the present invention. Alternatively, new attenuated *Escherichia* strains can be constructed by introducing one or more attenuating mutations as described for *Shigella* spp. above.

Additionally, a naturally occurring bleb-forming bacteria or a non bleb-forming bacterial species can be genetically altered to increase or initiate production of blebs. Genetic alterations for altering the bieb-forming ability of a bacterial species include, but are not limited to, deletions in or alterations to genes involved in cell wall formation, septation and the processes of bacterial division. Examples of such genes include, but are not limited to, the outer membrane lipoprotein genes such as *Escherichia coli* mlpD gene (Lange and Hengge-Aronis, Molec. Microbiol., 13:733–743 (1994)), *Bacillus subtilus* LplA gene (Gomez et al, Microbiol., 140:1839–1845 (1994)), *Haemophilus somnus* lppB gene (Theisen et al, Infect. Immun., 61:1793–1798 (1993)), the mini-cell producing genes such as *E. coli* minABDC (Adler et al., supra; and de Boer et al, supra), the *E. coli* htrB (Karow et al, supra), msbB (Karow and Georgopolous, supra), pbpA and pbpB genes (B egg and Donachie, supra); and the *E. coli* cytoplasmic membrane protein FtsL (Guzman et al, J. Bact., 174:7716–7728 (1992)). Such alterations to the genetic makeup of a bacterial strain can be made singularly or in conjunction with other alterations, by any of the methods described above for *Shigella* spp., to any of the bacterial strains listed above or to any other gram negative bacterial species. Bacterial species that are not known to produce blebs, or do not produce blebs at high rates, but can be altered to either produce blebs or increase their bleb production include, but are not limited to, *Yersinia* spp., *Klebsiella* spp., *Bordetella* spp., *Aeromonas* spp., *Franciesella* spp., *Corynebacterium* spp., *Citrobacter* spp., *Chlamydia* spp., *Brucella* spp., *Mycobacterium* spp., *Legionella* spp., *Rhodococcus* spp., *Pseudomonas* spp., *Helicobacter* spp., and *Vibrio* spp.

Concerning use of *Yersinia* spp., the particular *Yersinia* strain employed is not critical in the broad practice of the present invention. Examples of *Yersinia* strains that can be employed in the present invention include *Y. enterocolitica* (ATCC No. 9610) or *Y. pestis* (ATCC No. 19428). Attenuated *Yersinia* strains, such as *Y. enterocolitica* YeO3-R2 (al-Hendy et al, Infect. Immun., 60:870–875 (1992)) or *Y. enterocolitica* aroA (O'Gaora et al, Micro. Path., 9:105–116 (1990)) are preferably used in the practice of the present invention. Alternatively, new attenuated *Yersinia* strains can be constructed by introducing one or more attenuating mutations as described for *Shigella* spp. above.

In respect of use of *Klebsella* spp., the particular *Klebsiella* strain employed is not critical in the broad practice of the present invention. Examples of *Klebsiella* strains that can be employed in the present invention include *K. pneuoniae* (ATCC No. 13884). Attenuated *Klebsiella* strains are preferably used in the practice of the present invention, and can be constructed by introducing one or more attenuating mutations as described for *Shigella* spp. above.

Concerning the use of *Bordetella* spp., the particular *Bordetella* strain employed is not critical in the broad practice of the present invention. Examples of *Bordetella* strains that can be employed in the present invention include *B. bronchiseptica* (ATCC No. 19395). Attenuated *Bordetella* strains are preferably used in the practice of the present invention, and can be constructed by introducing one or more attenuating mutations as described for *Shigella* spp. above.

Regarding use of *Aeromonas* spp., the particular *Aeromonas* strain employed is not critical in the broad practice of the present invention. Examples of *Aeromonas* strains that can be employed in the broad practice of the present invention include *A. eucrenophila* (ATCC No. 23309). Alternatively, new attenuated *Aeromonas* strains can be constructed by introducing one or more attenuating mutations as described for *Shigella* spp. above.

In respect of *Franciesella* spp., the particular *Franciesella* strain employed is not critical in the broad practice of the present invention. Examples of *Franciesella* strains that can be employed in the practice of the present invention include *F. tularensis*(ATCC No. 15482). Attenuated *Franciesella* strains are preferably used in the practice of the present invention, and can be constructed by introducing one or more attenuating mutations as described f or *Shigella* spp. above.

Concerning *Corynebacterium* spp., the particular *Corynebacterium* strain employed is not critical in the broad practice of the present invention. Examples of *Corynebacterium* strains that can be employed in the present invention include *C. pseudotuberculosis* (ATCC No. 19410). Attenuated *Corynebacterium* strains are preferably used in the practice of the present invention, and can be constructed by introducing one or more attenuating mutations as described for *Shigella* spp. above.

Concerning use of *Citrobacter* spp., the particular *Citrobacter* strain employed is not critical in the broad practice of the present, invention. Examples of *Citrobacter* strains which can be employed in the present invention include *C. freundii* (ATCC No. 8090). Attenuated *Citrobacter* strains are preferably used in the practice of the present invention, and can be constructed by introducing one or more attenuating mutations as described for *Shigella* spp. above.

Regarding *Chlamydia* spp., the particular *Chlamydia* strain employed is not critical in the broad practice of the present invention. Examples of *Chlamydia* strains that can be employed in the present invention include *C. pneumoniae* (ATCC No. VR1310). Attenuated *Chlamydia* strains are preferably used in the practice of the present invention, and can be constructed by introducing one or more attenuating mutations as described for *Shigella* spp. above.

In respect of *Brucella* spp., the particular *Brucella* strain employed is not critical in the broad practice of the present invention. Examples of *Brucella* strains that can be employed in the present invention include *B. abortus* (ATCC No. 23448). Attenuated *Brucella* strains are preferably used in the practice of the present invention, and can be constructed by introducing one or more attenuating mutations as described for *Shigella* spp. above.

With respect to *Mycobacterium* spp., the particular *Mycobacterium* strain employed is not critical in the broad practice of the present invention. Examples of *Mycobacterium* strains that can be employed in the present invention include *M. intracellulare* (ATCC No. 13950) and *M. tuberculosis* (ATCC No. 27294). Attenuated *Mycobacterium* strains are preferably used in the practice of the present invention, and can be constructed by introducing one or more attenuating mutations as described for *Shigella* spp. above.

Concerning *Legionella* spp., the particular *Legionella* strain employed is not critical to the present invention. Examples of *Legionella* strains that can be employed in the present invention include *L. pneumophila* (ATCC No. 33156). Attenuated *Legionella* strains, such as a *L. pneumophila* mip mutant (Ott, FEMS Micro. Rev., 14:161–176 (1994)) are preferably used in the practice of the present invention. Alternatively, new attenuated *Legionella* strains can be constructed by introducing one or more attenuating mutations as described for *Shigella* spp. above.

Concerning *Rhodococcus* spp., the particular *Rhodococcus* strain employed is not critical in the broad practice of the present invention. Examples of *Rhodococcus* strains that can be employed in the present invention include *R. equi* (ATCC No. 6939). Attenuated *Rhodococcus* strains are preferably used in the practice of the present invention, and can be constructed by introducing one or more attenuating mutations as described for *Shigella* spp. above.

The particular *Pseudomonas* strain employed in use of *Pseudomonas* spp. is not critical in the broad practice of the present invention. Examples of *Pseudomonas* strains that can be employed in the present invention include *P. aeruginosa* (ATCC No. 23267). Attenuated *Pseudomonas* strains are preferably used in the present invention, and can be constructed by introducing one or more attenuating mutations as described for *Shigella* spp. above.

In respect of *Helicobacter* spp., the particular *Helicobacter* strain employed is not critical to the present invention. Examples of *Helicobacter* strains that can be employed in the present invention include *H. mustelae* (ATCC No. 43772). Attenuated *Helicobacter* strains are preferably used in the practice of the present invention, and can be constructed by introducing one or more attenuating mutations as described for *Shigella* spp. above.

When *Vibrio* spp. is employed, the particular *Vibrio* strain utilized is not critical. Examples of *Vibrio* strains that can be employed in the present invention include *Vibrio cholerae* (ATCC No. 14035) and *Vibrio* cincinnatiensis (ATCC No.

35912). Attenuated *Vibrio* strains are preferably used in the practice of the present invention and include *V. cholerae* RSI virulence mutant (Taylor et al, J. Infect. Dis., 170:1518–1523 (1994)) and *V. cholerae* ctxA, ace, zot, cep mutant (Waldor et al, J. Infect. Dis., 170:278–283 (1994)). Alternatively, new attenuated *Vibrio* strains can be constructed by introducing one or more attenuating mutations as described for *Shigella* spp. above.

Alternatively bacterial blebs can be encouraged to form through the treatment of bacterial cells with bacteriocidal and bacteriostatic agents. Examples of chemical induced bleb formation include gentamicin treatment of *Pseudomonas aeurginosa* (Kadurugamuwa et al., supra) and *penicillin* treatment of *Haemophilus* influenzae (Dargis et al, supra).

As discussed above, the recipient animal cells to which bacterial blebs deliver a eukaryotic expression cassette may be animal cells derived from fish, birds or reptiles.

Examples of bacteria that bind to and naturally interact with fish cells include, but are not limited to *Aeromonas salminocida* (ATCC No. 33658) and *Aeromonas schuberii* (ATCC No. 43700). Attenuated bacteria are preferably used in the practice of the invention, and include *A. salmonicidia* vapA (Gustafson et al, J. Mol. Biol., 237:452–463 (1994) or *A. salmonicidia* aromatic-dependent mutant (Vaughan et al, Infect. Immun., 61:2172–2181 (1993)).

Examples of bacteria that naturally interact with avian cells include, but are not restricted to, *Salmonella galinarum* (ATCC No. 9184), *Salmonella enteriditis* (ATCC No. 4931) and *Salmonella typhimurium* (ATCC No. 6994). Attenuated bacteria are preferred in the practice of the invention and include attenuated *Salmonella* strains such as *S. galinarum* cya crp mutant (Curtiss et al, (1987) supra) or *S. enteritidis* aroA aromatic-dependent mutant CVL30 (Cooper et al, Infect. Immun., 62:4739–4746 (1994)).

Examples of bacteria that naturally interact with reptilian cells include, but are not restricted to, *Salmonella typhimurium* (ATCC No. 6994). Attenuated bacteria are preferable in the broad practice of the invention and include attenuated strains such as *S. typhimuirum* aromatic-dependent mutant (Hormaeche et al, supra).

The specific animal cells transfected with the bacterial blebs are not critical in the broad practice of the present invention, but will usually be chosen depending on the natural range of cells with which the bacteria, from which the blebs are derived, normally interact.

For example, *Shigella flexneri* naturally interacts with human and primate cells, but rarely dogs and other animals (Kreig et al, Bergey's Manual of Systematic Bacteriology, Eds., Wilkins and Williams, Baltimore, Md. (1984)), while *Aeromonas salminocida* interacts with salmonid cells (Austin et al, Bacterial Fish Pathogens: Diseases in Farmed and Wild Fishes, Eds., Ellis Harwood Ltd., London (1987)).

The mucosal and systemic immune systems are compartmentalized(Mesteky, J. Clin. Immunol., 7:265–270 (1987); Newby, In: Local Immune Response of the Gut, Boca Raton, CRC Press, Newby and Stocks Eds., pages 143–160 (1984); and Pascual et al., Immuno. Methods., 5:56–72 (1994)). Thus, antigens delivered to mucosal surfaces elicit mucosal and systemic responses, whereas parentally delivered antigens elicit mainly systemic responses but only stimulate poor mucosal responses (Mesteky, supra). Moreover, mucosal stimulation at one mucosal site (for example the intestine) can result in development of immunity at other mucosal surfaces (for example genital/urinary tract) (Mesteky, supra). This phenomenon is referred to as the common mucosal system and is well documented (Mesteky, supra; and Pascual et al, supra).

The development of mucosal vaccines has been hindered by the poor immunogenicity of antigens when delivered by these routes. In this context, antigens can be divided into two classes: those that bind to intestinal surfaces and those that do not bind, where the former are significantly more immunogenic than the latter (De Aizpurua et al, J. Exp. Med., 176:440451 (1988). Similarly, delivery of DNA molecules to mucosal surfaces is inefficient due to the many natural host defenses found at these surfaces, such as the gastric barrier and nucleases in the gastrointestinal tract, and the thick mucous layer in the respiratory tract.

Bacterial vectors circumvent these natural barrier functions of the host and enable access to the mucosal compartment (Curtiss, in: New Generation Vaccines: The Molecular Approach, Ed., Marcel Dekker, Inc., New York, N.Y., pages 161–188 and 269–288 (1989); and Mims et al, in: Medical Microbiology, Eds., Mosby-Year Book Europe, Ltd., London (1993)). Certain enteric and respiratory pathogens, for example, *E. coli, Shigella, Listeria, Bordetella* and *Salmonella*, are naturally adapted for this application, as these organisms possess the ability to attach to and invade host mucosal surfaces (Kreig et al, supra). The present invention enables such mucosal compartment access to be exploited, e.g., by oral, intranasal, intravaginal, intrarectal, etc. delivery of bacterial blebs that are engineered to carry eukaryotic expression cassettes to the host mucosal compartment.

Alternatively, any bacteria could be genetically engineered to mimic mucosal tissue tropism properties, as discussed above, that thereby allow bacterial blebs made from such bacterial strain to interact with mucosal tissue, and deliver genes at those sites.

It is also possible to change the tissue specificity of the bacterial blebs by expression of a gene product, in their native form as genetic fusions or truncated versions, singularly or in combination, e.g., the *Plasmodium vivax* reticulocyte binding proteins-1 and -2 bind specifically to erythrocytes in humans and primates (Galinski et al, Cell, 69:1213–1226 (1992)); *Yersinia* invasin recognizes β1-integrin receptors (Isberg et al, Trends Microbiol., 2:10–14 (1994)); asialoorosomucoid is a ligand for the asilogycoprotein receptor on hepatocytes (Wu et al. J. Biol. Chem., 263:14621–14624 (1998)); presence of insulin-poly-L-lysine has been shown to target plasmid uptake to cells with an insulin receptor (Rosenkranz et al, Expt. Cell Res., 199:323–329 (1992)); p6O of *Listeria monocytogenes* allows for tropism for hepatocytes (Hess et al, Infect. Immun., 63:2047–2053 (1995)) and *Trypanosoma cruzi* expresses a 60 kDa surface protein which causes specific binding to the mammalian extra-cellular matrix by binding to heparin, heparin sulfate and collagen (Ortega-Barria et al, Cell, 67:411–421 (1991)). These or other molecules that influence the tissue or cell specificity of the bacterial blebs can also be attached to the surface of purified bacterial blebs by any of various suitable chemical or photo methodologies, as will be appreciated by those skilled in the art in the field of the present invention.

The particular eukaryotic cassette employed in the present invention is not critical in the broad practice of the invention, and can for example be selected from any of the numerous commercially available cassettes, such as pCEP4 or pRc/RSV obtained from Invitrogen Corporation (San Diego, Calif.), pXT1, pSG5, pPbac or pMbac obtained from Stratagene (La Jolla, Calif.), pPUR or pMAM obtained from ClonTech (Palo Alto, Calif.), and pSVβ-gal obtained from Promega Corporation (Madison, Wis.), or synthesized either de novo or by adaptation of a publicly or commercially available eukaryotic expression system.

The individual elements within the eukaryotic expression cassette can be derived from multiple sources and may be selected to confer specificity in sites of action or longevity of the cassettes in the recipient cell. Such manipulation of the eukaryotic expression cassette can be done by any standard or otherwise known molecular biology approach.

These cassettes usually are in the form of plasmids, and contain various promoters well-known to be useful for driving expression of genes in animal cells, such as the viral derived SV40, CMV and, RSV promoters or eukaryotic derived b-casein, uteroglobin, β-actin or tyrosinase promoters. The particular promoter is not critical in the broad practice of the present invention, except in the case where the object is to obtain expression in only selective cell types. In such case, the promoter is selected to be one that is only active in the selected cell type. Examples of tissue specific promoters include, but are not limited to, S1- and β-casein promoters, which are specific for mammary tissue (Platenburg et al, Trans. Res., 3:99–108 (1994); and Maga et al, Trans. Res., 3:36–42 (1994)); the phosphoenolpyruvate carboxylinase promoter, which is active in liver, kidney, adipose, jejunum and mammary tissue (McGrane et al, J. Reprod. Fert., 41:17–23 (1990)); the tyrosinase promoter, which is active in melanocytes, lung and spleen cells, but not testes, brain, heart, liver or kidney (Vile and Hart, Canc. Res., 53:962–967 (1993) and Vile et al, Canc. Res., 54:6228–6234 (1994)); the involucerin promoter, which is only active in differentiating keratinocytes of the squamous epithelia (Carroll et al., J. Cell Sci., 103:925–930 (1992)); neuron specific enolase promoter, which is active only in neurons (Anderson et al., Cell. Molec. Neurobiol., 13:503–515 (1993)), human skeletal alpha-actin and troponin 1 promoters, which are developmentally regulated in a muscle-specific manner (Dahler et al., Gene, 145:305–310 (1994)) and the uteroglobin promoter, which is active in lung and endometrium (Helftenbein et al, Annal. N.Y. Acad. Sci., 622:69–79 (1991)).

Alternatively, cell specific enhancer sequences can be used to control expression; for example, human neurotropic papovirus JCV enhancer regulates viral transcription in glial cells alone (Remenick et al, J. Virol., 65:5641–5646 (1991)). Yet another way to control tissue specific expression is to use a hormone responsive element (IRE) to specify the cell lineages in which a promoter will be active; for example, the MMTV promoter requires the binding of a hormone receptor, such as progesterone receptor, to an upstream HRE before it is activated (Beato, FASEB J., 5:2044–2051 (1991); and Truss et al, J. Steroid Biochem. Mol. Biol., 41:241–248 (1992)).

Additional genetic elements may be included on the plasmid in order to modify its behavior inside the recipient animal cell (Hodgson, Bio/Technology, 13:222–225 (1995). Such elements include, but are not limited to, mammalian artificial chromosome elements or elements from the autonomous replicating circular minichromosomes, such as found in DiFi colorectal cancer cells, to allow stable non-integrated retention of the expression cassette (Huxley et al, Bio/Technology, 12:586–590 (1994); and Untawale et al, Canc. Res., 53:1630–1636 (1993)), intergrase to direct integration of the expression cassette into the recipient cells chromosome Bushman, Proc. Natl. Acad. Sci., USA, 91:9233–9237 (1994), the inverted repeats from adeno-associated virus to promote non-homologous integration into the recipient cells chromosome (Goodman et al Blood, 84:1492–1500 (1994), recA or a restriction enzyme to promote homologous recombination (PCT Patent Publication No. WO9322443 (1993); and PCT Patent Publication No. WO9323534-A (1993)) or elements that direct nuclear targeting of the eukaryotic expression cassette (Hodgson, supra; and Lewin, supra). It may be advantageous to encode some of these elements, such as intergrase, recA, and restriction enzymes, in prokaryotic expression cassettes, either on the same genetic element as the eukaryotic expression cassette or alternatively on separate genetic elements. The placing of such toxic or deleterious elements under the control of a prokaryotic promoter ensures that these elements will only be transcribed or translated prior to formation of the bacterial bleb and its separation from the parental bacterial cell, while the prokaryotic translational and transcriptional machinery is present in completion and functioning; thus, a finite dose of the element encoded will be delivered to the eukaryotic recipient.

In accordance with the present invention, the bacterial bleb is employed to deliver eukaryotic expression cassettes encoding a gene into an animal cell or animal tissue. The gene may be either a foreign gene or an endogenous gene. As used herein, "foreign gene" means a gene encoding a protein or fragment thereof or anti-sense RNA or catalytic RNA, which is foreign to the recipient animal cell or tissue, such as a vaccine antigen, immunoregulatory agent, or gene therapeutic agent. An "endogenous gene" means a gene encoding a protein or part thereof or anti-sense RNA or catalytic RNA which is naturally present, or could reasonably be expected to be naturally present in the recipient animal cell or tissue under normal developmental conditions.

The gene, or coding sequence, or sequence that encodes the particular protein, is a nucleic acid molecule that is transcribed (in the case of DNA) and translated (in the case of mRNA) into a polypeptide in vitro or in vivo when placed under the control of appropriate regulatory sequences. The coding sequence boundaries include the start codon at the 5' (amino) terminus and the translation stop codon at the 3' (carboxy) terminus. The coding sequence can include, but is not limited to, cDNA from mRNA, genomic DNA sequences, and synthetic DNA sequences. A transcription termination sequence will usually be located 3' to the gene sequence.

The vaccine antigen may be a protein or antigenic fragment thereof from viral pathogens, bacterial pathogens, parasitic pathogens, or an autoantigen. Alternatively, the vaccine antigen may be a synthetic gene, constructed using recombinant DNA methods, which encode antigens or parts thereof from viral, bacterial, parasitic, etc., pathogens. These pathogens can be infectious in humans, domestic animals or wild animal hosts.

The antigen can be any molecule that is expressed by any viral, bacterial, parasitic, etc., pathogen prior t0 or during entry into, colonization of, or replication in the animal host. The vaccine antigen can also be an autoantigen, i.e., an antigen that is present at some time spatially or developmentally in the recipient animal cell or tissue.

Multiple eukaryotic expression cassettes can be delivered that express any combination of viral, bacterial, parasitic, etc., antigens, or synthetic genes encoding all or parts or any combination of viral, bacterial, parasitic, etc., antigens. Eukaryotic expression cassettes encoding vaccine antigens can also be delivered in conjunction with additional expression cassettes encoding known adjuvants. Examples of adjuvants include, but are not limited to, IL-12 (Hall, Sci., 268:1432–1434 (1995)) and bacterial lipopolysaccharide or lipid A (Alving, Immunobiol., 187:430–446 (1993)), outer membrane proteins such as ompA. The viral pathogens, from which the viral antigens are derived, include, but are not limited to, Orthomyxoviruses, such as influenza virus; Retroviruses, such as RSV and SIV, Herpesviruses, such as EBV; CMV or herpes simplex virus; *Lentiviruses*, such as human immunodeficiency virus; Rhabdoviruses, such as rabies; Picornoviruses, such as poliovirus; Poxviruses, such as *vaccinia; Rotavirus*; and Parvoviruses.

Examples of protective antigens of viral pathogens include the human immunodeficiency virus antigens nef, p24, gp120, gp41, tat, rev, and pol (Nat., 313:277–280 (1985)) and T cell and B cell epitopes of gp120 (Palker et al, J. Immunol., 142:3612–3619 (1989)); the hepatitis B surface antigen (Wu et al, Proc. Natl. Acad. Sci., USA, 86:4726–4730 (1989)); *rotavirus* antigens, such as VP4 (Mackow et al, Proc. Natl. Acad. Sci., USA, 87:518–522 (1990)) and VP7 (Green et al, J. Virol., 62:1819–1823 (1988)), influenza virus antigens such as hemagglutinin or nucleoprotein (Robinson et al., supra; Webster et al, supra) and herpes simplex virus thymidine kinase (Whitley et al, In: New Generation Vaccines, pages 825–854).

The bacterial pathogens, from which the bacterial antigens are derived, include, but are not limited to, *Mycobacterium* spp., *Helicobacter pylori, Salmonella* spp., *Shigella* spp., *E. coli, Rickettsia* spp., *Listeria* spp., *Legionella pneumoniae, Pseudomonas* spp., *Vibrio* spp., and *Borellia burgdorferi*.

Examples of protective antigens of bacterial pathogens include the *Shigella sonnei* form 1 antigen (Formal et al, Infect. Immun., 34:746–750 (1981)); the O-antigen of *V. cholerae* Inaba strain 569 B (Forrest et al, J., Infect. Dis. 159:145–146 (1989); protective antigens of enterotoxigenic *E. coli* such as the CFA/I fimbrial antigen (Yamamoto et al, Infect. Immun., 50:925–928 (1985)) and the nontoxic B-subunit of the heat-labile toxin (Klipstein et al, Infect. Immun., 40:888–893 (1983)); pertactin of *Bordetella pertussis* (Roberts et al, Vacc., 10:43–48 (1992)), adenylate cyclase-hemolysin of *B. pertussis* (Guiso et al, Micro. Path., 11:423431 (1991)), and fragment C of tetanus toxin of *Clostridium tetani* (Fairweather et al, Infect. Immun., 58:1323–1326 (1990)).

The parasitic pathogens, from which the parasitic antigens are derived, include, but are not limited to, *Plasmodium* spp., *Trypanosome* spp., *Giardia* spp., *Boophilus* spp., *Babesia* spp., *Entamoeba* spp., *Eimeria* spp., *Laishmania* spp., *Schistosome* spp., *Brugia* spp., *Fascida* spp., *Dirofilaria* spp., *Wuchereria* spp., and *Onchocerea* spp.

Examples of protective antigens of parasitic pathogens include the circumsporozoite antigens of *Plasmodium* spp. (Sadoff et al, Sci., 240:336–337 (1988)), such as the circumsporozoite antigen of *P. bergerii* or the circumsporozoite antigen of *P. falciparum*; the merozoite surface antigen of *Plasmodium* spp. (Spetzler et al, Int. J. Pept. Prot. Res., 43:351–358 (1994)); the transmission blocking *P. falciparum* gamete surface proteins Pfs230 (Read et al, Para. Immunol., 16:511–519 (1994)), Pfs48/45 (Kochen at al, Mol. Biocham Parasit., 61:59–68 (1993)) and Pfs2400 (Feng et al, J. Expt. Med., 177:273–281 (1993)); the galactose specific lectin of *Entamoeba histolytica* (Mann et al, Proc. Natl. Acad. Sci., USA, 88:3248–3252 (1991)), gp63 of *Leishmania* spp. (Russell et al, J. Immunol., 140:1274–1278 (1988)), paramyosin of *Brugia malayi* (Li et al, Mol. Biochem. Parasitol., 49:315–323 (1991)), the triose-phosphate isomerase of *Schistosoma mansoni* (Shoemaker et al, Proc. Natl. Acad. Sci., USA, 89:1842–1846 (1992)); the secreted globin-like protein of *Trichostrongylus colubriformis* (Frenkel et al, Mol. Biochem. Parasitol., 50:27–36 (1992)); the glutathione-S-transferase's of *Frasciola hepatica* (Hillyer et al, Exp. Parasitol., 75:176–186 (1992)), *Schistosoma bovis* and *S. japonicum* (Bashir et al, Trop. Geog. Med., 46:255–258 (1994)); and KLH of *Schistosoma bovis* and *S. japonicum* (Bashir et al, supra).

Examples of autoantigens include, but are not limited to, fertility antigens such as those which are present on the sperm, oocyte or zona pelucida. Development of an immune response to such antigens is known to block the full-term development of gametes and such antigens can therefore be used in fertility control applications. Illustrative fertility blocking antigens include the 51 kDa sperm-specific glycoprotein FA-1 (Naz and Ahamd, Mol. Reprod. Develop., 39:397–408 (1994)); human sperm 34 kDa protein P34H and hamster 26 kDa epididymal sperm protein (Boue et al, Biol. Reprod., 51:577–587 (1994)); rabbit sperm cap plasma membrane 40 kDa surface antigen (Shaha, Mol. Reprod. Develop., 38:393–403 (1994)); human and mouse antigens recognized by anti-human monoclonal antibodies DAN-2, MOU-8 and VAC-4 (Garcia Framis et al, Immunol. Invest. 23:15–24 (1994)); and the sperm/placenta cross reacting antigen STX-10 (Lee et al, J. Reprod. Immunol., 25:249–264 (1993)).

In accordance with one aspect of the present invention, bacterial blebs can be utilized to deliver eukaryotic expression cassettes encoding a therapeutic agent to animal cells or animal tissue. For example, the eukaryotic expression cassettes can encode tumor-specific, transplant, or autoimmune antigens or parts thereof. Alternatively, the eukaryotic expression cassettes can encode synthetic genes, which encode tumor-specific, transplant, or autoimmune antigens or parts thereof.

Examples of tumor specific antigens include prostate specific antigen (Gattuso et al, Human Pathol., 26:123–126 (1995)), TAG-72 and CEA (Guadagni et al, Int. J. Biol. Markers, 9:53–60 (1994)), MAGE-1 and tyrosinase (Coulie et al, J. Immunothera., 14:104–109 (1993)). It has been demonstrated in mice that immunization with non-malignant cells expressing a tumor antigen provides a vaccine effect, and also helps the animal thereby treated to mount an immune response to clear malignant tumor cells displaying the same antigen (Koeppen et al, supra); additionally, vaccination with a human carcinoembryonic antigen vaccine has been demonstrated to protect mice against a challenge by colon carcinoma cells (Conry et al., supra).

Examples of transplant antigens include the CD3 receptor on T cells (Alegre et al, Digest. Dis. Sci., 40:58–64 (1995)). Treatment with an antibody to CD3 receptor has been shown to rapidly clear circulating T cells and reverse most rejection episodes (Alegre et al, supra). It has also been shown that delivery of a gene encoding transforming growth factor β-1 to tissue grafts can prolong allograft survival (Qin et al, supra).

Examples of autoimmune antigens include IAS β-chain (Topham et al, Proc. Natl. Acad. Sci., USA, 91:8005–8009 (1994)). Vaccination with an 18 amino acid peptide from IAS β chain has been demonstrated to provide protection and treatment to mice with experimental autoimmune encephalomyelitis (Topham et al, supra).

In addition, the bacterial blebs described herein can be used to deliver gene therapeutic agents or genes to recipient animal cells or animal tissue. Strategies for gene therapy include the genetic complementation of inherited or spontaneous genetic disorders, mutations, or deficits (Lisziewicz, Leuk., 8:S152–155 (1994)), and the supplementation of genes in order to enhance or alter the dose of a particular encoded factor or enzyme. Genetic elements delivered in eukaryotic expression cassettes by bacterial blebs to complement a mutated or non-functional gene in the animal cell can encode an entire replacement gene, or set of related genes, a complimentary DNA sequence encoding a primary RNA transcript, partially or completely processed RNA transcript, trans- or cis-acting regulatory element, enhancer or other modulatory factor. In order to complement some genetic defects it may be necessary to deliver one or more eukaryotic expression cassettes each encoding one or more components of a biochemical pathway, multi-enzyme process, or gene therapeutic elements can be delivered individually or in combination with other genes, or other eukaryotic expression cassettes. Eukaryotic expression cassettes delivered to animal cells by bleb-mediated transfection could be under the control of tissue specific, consitutive and/or inducible promoters, enhancers, or other transcriptional modification systems, as described above.

The advent of increasingly more powerful molecular techniques has recently resulted in an exponential growth of information on genetic lessions and the disease states resulting from such lessions. A large number of genetic lessions and resulting disease states has therefore been identified. Diseases for which a specific genetic lession has been defined and appertaining in vitro or in vivo treatments reported. The gene or genes in which the genetic lessions occur include, but are not limited to, cystic fibrosis-cystic fibrosis transmembrane conductance regulator (Yoshimura et al., Nuc. Acids Res., 20:3233–3240 (1992); Zabner et al., Cell. 75:207–216 (1993); Zabner et al, supra (1994); Caplen et al, supra); emphysema-α1 antitrypsin (Setoguchi et al., Am. J. Resp. Cell. Molec. Biol., 10:369–377 (1994)); familial hypercholesterolaemia-LDL receptor (Grossman et al, Nat. Genet., 6:335–341 (1994)); fanconi anemia-fanconi anemia C complementing gene (Walsh et al., Blood, 84.453–459 (1994)); hypertension-kallikrein gene (Wang et al., J. Clin. Invest., 95:1710–1716 (1995) mucopolysaccharidosis type II (Hunter syndrome)-iduronate-2-sulfatase (Braun et al., Proc. Natl. Acad. Sci., USA, 90:11830–11834 (1993)); propionyl coA carboxylase defficeny-PCCA (Stankovics and Ledley, Am. J. Hum. Genet., 52:144–151 (1993)); Sly syndrome-beta-glucuronidase (Moullier et al, Nat. Genet., 4:154–159 (1993)); and X-linked ichthyosis-steroid sulphatase (Jensen et al., Exp. Cell Res., 209:392–397 (1993)). Addition of a correctly functioning copy of the mutated or non-functional gene, via blebs transfection in accordance with the invention, embodies a useful approach to the treatment of such genetic deficiencies.

As another aspect of the present invention, bacterial blebs can deliver eukaryotic expression cassettes encoding immunoregulatory molecules. These immunoregulatory molecules include, but are not limited to, growth factors, such as M-CSF, GM-CSF; and cytokines, such as IL-2, IL-4, IL-5, IL-6, IL-10, IL-12, IL-13 or IFN-γ. In application to tumor tissue, cytokine expression cassettes can be employed to stimulate potent systemic immunity and enhanced tumor antigen presentation without producing a systemic cytokine toxicity (Golumbek et al, Canc. Res., 53:5841–5844 (1993); Golumbek et al, Immun. Res., 12:183–192 (1993); Pardoll, (1992a) supra; Pardoll, (1992b) supra; Melani et al, Nat. Immun., 13:76–84 (1994); and Harris et al., Cancer., 74S: 1021–1025 (1994)), and cause a reduction in the size of the tumor (Cignetti et al, J. Natl. Canc. Inst., 86:785–791 (1994); Pappo et al, supra; and Cordier et al., Gene Ther., 2:16–21 (1995)).

In antisense RNA and catalytic RNA applications, the antisense RNA and catalytic RNA species delivered to animal cells can be targeted against any molecule present within the recipient cell or likely to be present within the recipient cell. These include but are not limited to RNA species encoding cell regulatory molecules, such as interleukin-6 (Mahieu et al, Blood, 84:3758–3765 (1994)), oncogenes such as ras (Kashani-Sabet et al, Antisen Res. Devel., 2:3–15 (1992)), causative agents of cancer such as human papillomavirus (Steele et al, Canc. Res., 52:4706–4711, (1992)), enzymes, viral RNA's and pathogen derived RNAs such as HIV-1, (Chuah et al, Hum. Gene. Thera, 15:1467–1475 (1994); Meyer et al, Gene, 129:263–268 (1993); Chatterjee et al, Sci., 258:1485–1488 (1992); Tung and Daniel, supra; and Yamada et al, Virol., 205:121–126 (1994)). RNAs can also be targeted at non-transcribed DNA sequences, such as promoter or enhancer regions, or to any other molecule present in the recipient cells, such as but not limited to, enzymes involved in DNA synthesis or TRNA molecules (Scanlon et al, Proc. Natl. Acad. Sci. USA, 88:10591–10595 (1991); and Baier et al, Mol. Immunol., 31:923–932 (1994)).

In the broad practice of the present invention, bacterial blebs can also be used to deliver eukaryotic expression cassettes encoding proteins to animal tissue from which the expressed proteins can later be harvested or purified. An example is the delivery of a eukaryotic expression cassette under the control of a mammary specific viral promoter, such as derived from mouse mammary tumor virus (ATCC No. VR731), encoding α1-antitrypsin to mammary tissue of a goat or sheep.

As a further alternative, single or multiple eukaryotic expression cassettes encoding tumor-specific, transplant, and/or autoimmune antigens, can be delivered in any single or multiple combination with eukaryotic expression cassettes encoding immunoregulatory molecules or other proteins.

The invention also encompasses delivery of prokaryotic expression cassettes in combination with eukaryotic expression cassettes.

The bacterial blebs containing the eukaryotic expression cassette can be used to treat animal cells that are cultured in vitro. The animal cells can be further cultured in vitro, and the cells carrying a desired genetic trait can be enriched by selection for or against any selectable marker introduced to the recipient cell at the time of bactofection. Such markers may include antibiotic resistance genes, e.g., hygromycin, or neomycin, selectable cell surface markers, or any other phenotypic or genotypic element introduced or altered by bactofection. These in vitro-infected cells or the in vitro-enriched cells can then be introduced into animals intravenously, intramuscularly, intradermally, or intraperitoneally, or by any inoculation route that allows the cells to enter the host tissue.

Alternatively, the bacterial blebs containing the eukaryotic expression cassettes can be introduced to infect the animal by intravenous, intramuscular, intradermal, intraperitoneal, peroral, intranasal, intraocular, intrarectal, intravaginal, oral, immersion, intraurethral, or any other suitable administration or inoculation routes.

The amount of the bacterial blebs of the present invention to be administered will vary depending on the species of the subject, as well as the disease or condition that is being treated. Generally, the dosage employed will be in a range of from about $10^2$ to about $10^{21}$ blebs, preferably from about $10^6$ about $10^{12}$ blebs. Alternatively, when transfecting individual cells in vitro, the dosage of blebs to be administered will vary depending on the cells, but generally the ratio of blebs:cells will be in a range of from about 0.1:1 to about $10^9$:1, and preferably from about 1:1 to about $10^5$:1.

The bacterial blebs of the present invention are generally administered along with a pharmaceutically acceptable carrier or diluent.

The particular pharmaceutically acceptable carrier or diluent employed is not critical in the general practice of the present invention. Examples of diluents include physiological media used for in vitro tissue culture such as RPMI, DMEM or MEM, a phosphate buffered saline, buffer for buffering against gastric acid in the stomach, such as citrate buffer (pH 7.0) containing sucrose, bicarbonate buffer (pH 7.0) alone (Levine et al, J. Clin. Invest., 79:888–902 (1987); and Black et al J. Infect. Dis., 155:1260–1265 (1987)), or bicarbonate buffer (pH 7.0) containing ascorbic acid, lactose, and optionally aspartame (Levine et al, Lancet, II: 467–470 (1988)). Examples of carriers include proteins, e.g., as found in skim milk or serum, sugars (e.g., sucrose), glycerol, ammonium sulfate or polyvinylpyrrolidone. Typically these carriers are used at a concentration in a range of about 0.1 to about 90% (w/v), and preferably in a range of from about 1 to about 20% (w/v).

The features and advantages of the present invention are more fully shown by the following non-limiting examples, which are provided for illustrative purposes only, and are in no way intended to limit the scope of the present invention.

EXAMPLE I

Bleb-Mediated Transfection Using a Eukaryotic Expression Cassette

The following experiment was carried out to demonstrate that bacterial blebs are able to introduce a foreign gene into animal cells, which is then expressed by the animal cells (hereinafter "bleb-mediated transfection").

A. The Eukaryotic Expression Cassette

An attenuated *Shigella flexneri* strain containing both ΔaroΔ and ΔvirG attenuating lesions (Noriega et al, supra) was transformed with the dual prokaryotic/eukaryotic expression cassette containing plasmid pSVβ-gal (Promega Corporation, Madison, Wis.), which contains the reporter gene β-galactosidase (β-gal) (hereinafter "pβ-gal+SV"), under the control of both a prokaryotic (gpt) as well as a viral derived, eukaryotic (SV40) promoter. A second population of the same *Shigella flexneri* strain containing both ΔaroΔ and ΔvirG attenuating lesions (Noriega et al, supra) was transformed with an expression cassette containing containing plasmid pβ-gal-SV, a derivative of pβ-gal+SV from which the eukaryotic SV40 promoter had been removed by standard molecular biology techniques leaving only a prokaryotic expression cassette. Thus plasmid pβ-gal+SV was capable of directing synthesis of β-gal enzyme inside bacteria as well as animal cells, while plasmid pβ-gal-SV was capable of directing synthesis of β-gal enzyme only inside bacteria.

The resulting transformed bacteria were seeded from 30% (w/v) glycerol stocks, maintained at −70° C., onto solid medium (Tryptic Soy Agar, DIFCO, Madison, Wis.) containing 100 mg/ml of ampicillin, to select for bacteria containing the plasmids, and grown overnight at 37° C.

B. Isolation of Bacterial Blebs

Bacterial blebs were prepared from cells grown on solid media (Tryptic soy agar) overnight at 37° C. Cells were either harvested directly from solid media by scraping, or seeded into liquid media (RPMI) to an optical density of 0.2 $OD_{600}$ and grown for three hours before harvesting. Bacterial cells harvested from solid media were suspended in RPMI at a density of approximately 0.1 g cells per mL and mixed vigorously by vortex action for 5 minutes. Whole bacterial cells were pelleted from liquid cultures or bacterial suspensions by centrifugation at 10,000×g for 10 mins. The supernatant was removed and centrifuged again at 10,000×g for 20 mins. The resulting cell-free, bleb-containing supernatant was filtered through a 0.2 μm filter then concentrated 10–20 fold with an Amicon (Lexington, Mass.) stirred cell ultrafiltration cell using a 100k Da cutoff membrane before storage at 4° C. Protein concentration was determined by BCA assay (Pierce, Rockford Ill.). Concentrated bleb preparations were confirmed bacterial free by plating 50 μL on Tryptic Soy Agar, and seeding 2×50 μL into 5 mL RPMI each. If no growth was detected after 24 hours at 37° C., the resultant bleb-fractions were used for transfection assays.

C. The Eukaryotic Cells

HeLa cells (ATCC No. CCL-2) were grown on plastic tissue culture plates at 37° C. in 5% (v/v) $CO_2$ in RPMI medium supplemented with 10% (v/v) fetal bovine serum, 2.0 mM L-glutamine, 1.0 mM L-pyruvate, 50 U/ml penicillin and 50 mg/ml streptomycin (hereinafter "RPMI/FBS"). 24 to 48 hours prior to bactofection, the HeLa cells were trypsinized with 0.25% (w/v) trypsin containing 1.0 mM EDTA, and split by limiting dilution such that they were 40–60% confluent at the time of the experiment.

Prior to bleb-mediated transfection, the number of HeLa cells present was ascertained by counting in a hemocytometer (Celis, Cell Biology: A Laboratory Manual, Ed,. Academic Press, San Diego, Calif. (1994)).

D. Bleb-Mediated Transfection of the Eukaryotic Cells $5 \times 10^4$ HeLa cells were washed once with RPMI media lacking fetal bovine serum and penicillin/streptomycin (hereinafter "SFM"), then overlaid with a bleb-containing suspension, and incubated at 37° C. in 5% $CO_2$. The bleb suspension was either off the overnight agar plates or from a fresh broth culture, and was prepared to give an infection ratio of approximately 5 to 100 ug protein to 1 HeLa cell.

After 3 hours, the bleb-containing media was removed, the HeLa cells were rinsed once with RPMI/FBS, and then fresh RPMI/FBS was added and the cells were returned to 37° C. in 5% $CO_2$.

At 6 hours, 24 hours, 48 hours, and 92 hours post-bleb-mediated transfection, the HeLa cells were washed twice with phosphate buffered saline (hereinafter "PBS"), stained for β-gal activity as described by Hawley-Nelson et al, Focus, 15:73–79 (1993), and then photographed. When the incubation time prior to analysis was greater than 48 hours, then the RPMI/FBS was changed at 48 hours.

Cells in which the cytoplasm had stained evenly blue were only observed for HeLa cells transfected with bleb-containing supernatants derived from *Shigella* cells in which the pβ-gal+SV plasmid had been present, i.e., those blebs which contained a plasmid containing a eukaryotic expression cassette. HeLa cells transfected with blebs derived from *Shigella* cells in which the pβ-gal-SV plasmid had been present did not result in a transfected, evenly staining, β-gal positive phenotype. Thus, transfection of HeLa cells with blebs that contained only a prokaryatic expression cassette did not result in a transformed phenotype. Blebs prepared from both *Shigella* cell types (i.e., those containing pβ-gal+SV, as well as those containing pβ-gal-SV) resulted in HeLa cells that showed discrete blue stained 'dots' resulting from the delivery of bacterially synthesized β-gal enzyme, i.e., enzyme synthesized prior to the formation of the bleb and its separation from the bacterial parent cell. None of the HeLa cells transfected with blebs isolated from the *Shigella* cells containing pβ-gal-SV resulted in a transformed phenotype. The average extent of confluent staining was greater the longer the period between bleb-mediated transfection and staining, which indicates that expression was not due solely to β-gal synthesized by the *Shigella* prior to bleb formation, and packaged in the bleb at the time of formation, but rather was a result of β-gal newly synthesized within the HeLa cell.

The foregoing empirically demonstrates that bacterial blebs can be used to deliver a eukaryotic expression cassette to animal cells for expression therein of the contained genetic information.

EXAMPLE 2

Blebs Delivery of Pre-Synthesized Molecules to Animal Cells

The results in Example 1 also demonstrated that bacterial blebs are able to deliver pre-synthesized molecules to animal cells, as shown by the ability of blebs derived from *Shigella* in which the pβ-gal-SV plasmid had been present. Thus, bacterial blebs can be used to deliver previously synthesized molecules, produced from prokaryotic expression cassettes by the bacteria from which the bleb was derived, prior to bleb formation, to recipient animal cells.

EXAMPLE 3

Production of Non-Pyrogenic Blebs from *Salmonella*

In this example we show that Blebs can be produced, and purified, from a non-pyrogenic *Salmonella* strain. To produce the Blebs, a non-pyrogenic *Salmonella* strain herein designated "T109", which is a *Salmonella* carrying deletion mutations in the aroA and msbB genes, was cultured in 100 ml luria-bertani broth (LB; Difco, Detroit Mich.) at 37° C. with agitation (i.e. 200 oscillations per min; OPM) to an optical density at 600 nm ($OD_{600}$) of from 0.4 to 0.8 relative to a sterile LB control. At this point, gentamicin (Lifetechnologies; Gaithersburg, Md.) is added to a final concentration of 5 μg/ml and the culture is incubated as above for a further 30 min. To harvest the blebs, the bacteria were removed by centrifugation at 7,000×g for 20 min. Following centrifugation the supernatant, which contains the Blebs, was decanted into a sterile centrifuge tube. The Blebs were harvested from the supernatant by centrifugation at 20,000×g for 30 min. Following this second centrifugation step, the supernatant was discarded and the pellet, which contained the Blebs, was resuspended in 1 ml endotoxin-free phosphate buffered saline (PBS; Lifetechnologies, Gaithersburg, Md.). To remove trace bacteria that remained in the enriched Bleb preparation, this latter 1 ml suspension was passed through a 1.2 μM filter (Nalgene, Rochester N.Y.), then a 0.45 μM filter (Millipore, Bedford Mass.). To validate sterility 10 μl aliquots of the filtrate were plated onto a series of 5 luria-bertani agar (LA) plates and incubated at 37° C. for 16 hr. No colonies appeared following incubation, indicating that the filtrates, which contained the non-pyrogenic *Salmonella* blebs, contained <10 colony forming units (cfu) per ml. To verify that the filtrates contained Blebs, 10 μl of the filtrate was placed onto a microscope slide and examined 400× magnification using a Nikon Eclipse TE300 microscope (Tokyo, Japan). The concentration of Blebs in the filtrates was estimated to be about $10^9$ per ml.

To gain better measure of the concentration of Blebs in the suspensions described above, the total protein concentration was determined by BCA quantitative protein assay (Pierce, Rockford, Ill.). A standard curve was produced using bovine serum albumin (Pierce, Rockford Ill.) according to the manufacturer's direction. The total protein concentration was found to be 80 ng per ml. In addition, the total lipopolysaccharide concentration was measured using the liminus amebocyte lysate (LAL) assay (Cape Cod Associates, Cape Cod Me.). The LAL assay indicated that the LPS concentration in the Bleb preparation was around 100 ng per ml. These values provided a measure to standardize the dose of Blebs for the in vivo studies described in the following example.

EXAMPLE 4

Vaccination of Mice with Non-Pyrogenic *Salmonella* Blebs

Individual groups of three specific pathogen-free, 18–20 gram female BALB/cAnNCrlBR mice (Charles River Laboratories, Wilmington, Mass.) were vaccinated with a single dose of about 10 pg or 50 pg protein concentration equivalent of T109 Blebs suspended in 100 μl PBS, by intragastric intubation. Prior to vaccination, the mice were given 100 μl of 50% (w/v) bicarbonate, also by intragastric intubation.

Prior to and one week after vaccination, about 100 μl of blood was collected from the tail vein of each mouse and allowed to clot. The sera from these samples was collected by first removing the clots by centrifugation in a microfage for 5 min at 13,000 rpm and decanting the sera into fresh tubes.

The *Salmonella*-specific serum IgG responses were measured in these sera using a conventional ELISA and whole inactivated *Salmonella* as antigen. Briefly, the wells of a 96 well microtiter plate were treated with 100 μl of acetone-inactivated *Salmonellae* suspended in PBS at a concentration of $10^7$ *bacilli* per ml for 16 hr at room temperature. These plates were subsequently washed with PBS and 200 μl of 5% (w/v) non-fat dried milk (suspended in PBS) was added to each well. After a further 1 hr the wells were wased once with 200 μl PBS and 100 μl of samples of diluted pre- and post-vaccination sera were added, starting at a dilution of 1:30 and in 3-fold serial dilutions to 1:27,000. The plates were incubated for a further 1 hr and the wells were washed 4 times with 200 μl of PBS. *Salmonella*-specific IgG was detected using colorimetrically using a 1:1000 dilution of rat anti-mouse IgG-horse-radish peroxidase conjugate (Sigma, St Louis Mo.) and standard substrates, according to the directions of the manufacturer. The results of the ELISA show that vaccination of mice with a single dose of the non-pyrogenic *Salmonella* Blebs induced a strong serum IgG response against *Salmonella* (FIG. 1).

The results show conclusively that vaccination of mice with both the 10 pg and 50 pg doses of non-pyrogenic *Salmonella* Blebs resulted in the development of strong serum IgG responses against *Salmonella*. Since serum IgG responses against *Salmonella* have been shown previously to correlate with protection against *Salmonella*, these data show that non-pyrogenic Blebs are useful and inexpensive method for producing vaccines against bacterial pathogens.

EXAMPLE 5

Production of Non-Pyrogenic Blebs Containing a DNA Vaccine

In this example we show that Blebs can be produced by, and purified from, a non-pyrogenic *Salmonella* strain that carries DNA vaccine pOGL1-A1 (SEQ ID NO: 1; FIG. 3). Plasmid pOGL1-A1 expresses the 120 kDA glycoprotein (i.e. gp120) of human immunodeficiency virus type 1 (HIV-1) and the A1 subunit of cholera toxin (i.e. CtxA1). We have shown previous that intramuscular vaccination with the dicistronic DNA vaccine pOGL1-A1 induces strong immune responses against HIV-1 (Hone et al, co-pending U.S. patent application Ser. No. 09/950,335). Production of the Blebs from strain H1071, which is a non-pyrogenic *Salmonella* strain SL7207 carrying deletion mutations in the aroA and msbB genes and harboring DNA vaccine pOGL1-A1, was accomplished by growing H1071 in 100 ml luria-bertani broth (LB; Difco, Detroit Mich.) at 37° C. with agitation (i.e. 200 oscillations per min; OPM) to an optical density at 600 nm ($OD_{600}$) of from 0.4 to 0.8 relative to a sterile LB control. At this point, gentamicin (Lifetechnologies; Gaithersburg, Md.) was added to a final concentration of 5 μg/ml and the culture was incubated as above for a further 30 min. To harvest the blebs, the live whole bacteria were removed by centrifugation at 7,000×g for 20 min. Following centrifugation the supernatant containing the Blebs, was decanted into a sterile centrifuge tube. The H1071 Blebs were then harvested from the supernatant by centrifugation at 20,000×g for 30 min. Following this second centrifugation step, the supernatant was discarded and the pellet containing the H1071 Blebs was resuspended in 1 ml endotoxin-free phosphate buffered saline (PBS; Lifetechnologies, Gaithersburg, Md.). As shown in example 1 above, trace bacteria that remained in the enriched Bleb preparation were removed by passing this suspension through a 1.2 μM filter (Nalgene, Rochester N.Y.), then a 0.45 μM filter (Millipore, Bedford Mass.).

To validate sterility 10 μl aliquots of the filtrate were plated onto a series of 5 luria-bertani agar (LA) plates and incubated at 37° C. for 16 hr. No colonies appeared following incubation, indicating that the filtrates, which contained the non-pyrogenic *Salmonella* blebs, contained <10 colony forming units (cfu) per ml. To verify that the filtrates contained Blebs, 10 μl of the filtrate was placed onto a microscope slide and examined 400× magnification using a Nikon Eclipse TE300 microscope (Tokyo, Japan). The concentration of Blebs in the filtrates was estimated to be about $10^{8-109}$ Blebs per ml.

To gain better measure of the concentration of Blebs in the suspensions described above, the total protein concentration was determined by BCA quantitative protein assay (Pierce, Rockford, Ill.). A standard curve was produced using bovine serum albumin (Pierce, Rockford Ill.) according to the manufacturer's direction. The total protein concentration was found to be 80 ng per ml. In addition, the total lipopolysaccharide concentration was measured using the liminus amebocyte lysate (LAL) assay (Cape Cod Associates, Cape Cod Me.). The LAL assay indicated that the LPS concentration in the Bleb preparation was around 100 ng per ml. These values provided a measure to standardize the dose of Blebs for the in vivo studies described in the following example. Presence of pOGL1-A1 in the Bleb preparaion was confirmed by polymerase chain reaction amplification of sequences in pOGL1-A1 using conventional procedures well know in the art and primers specific for sequences encoding gp120. The PCR was strongly positive indicating that the Blebs harbored substantial lelves of pOGL1-A1 DNA.

EXAMPLE 6

Vaccination of Mice with Non-Pyrogenic Blebs Harboring a DNA Vaccine

Individual groups of three specific pathogen-free, 18–20 gram female BALB/cAnNCrIBR mice (Charles River Laboratories, Wilmington, Mass.) were vaccinated with a single dose of about 10 pg or 50 pg protein concentration equivalent of H1071 Blebs suspended in 100 μl PBS, by intragastric intubation. Prior to vaccination, the mice were given 100 μl of 50% (w/v) bicarbonate, also by intragastric intubation. Prior to and one week after vaccination, about 100 μl of blood was collected from the tail vein of each mouse and allowed to clot. The sera from these samples was collected by first removing the clots by centrifugation in a microfuge for 5 min at 13,000 rpm and decanting the sera into fresh tubes.

Figure 2:
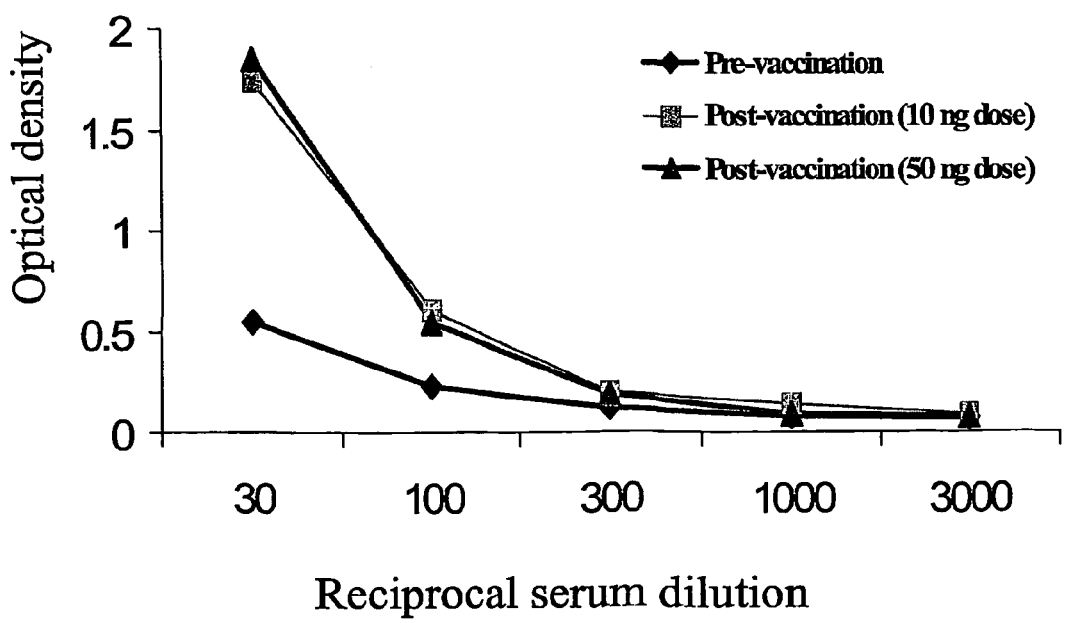
FIG. 2 shows the results of the ELISA showing that vaccination of mice with a single dose of the non-pyrogenic Salmonella Blebs harboring POGL1-A1 induced a strong serum IgG response against gp 120.

The gp120-specific serum IgG responses were measured in these sera using a conventional ELISA and purified recombinant gp120 as antigen. Briefly, the wells of a 96 well microtiter plate were treated with 100 μl of gp120 suspended in PBS at a concentration of 10 μg per ml for 16 hr at room temperature. These plates were subsequently washed with PBS and 200 μl of 5% (w/v) non-fat dried milk (suspended in PBS) was added to each well. After a further 1 hr the wells were wased once with 200 μl PBS and 100 μl of samples of diluted pre- and post-vaccination sera were added, starting at a dilution of 1:30 and in 3-fold serial dilutions to 1:27,000. The plates were incubated for a further 1 hr and the wells were washed 4 times with 200 μl of PBS. Gp120-specific IgG was detected using calorimetrically using a 1:1000 dilution of rat anti-mouse IgG-horse-radish peroxidase conjugate (Sigma, St Louis Mo.) and standard substrates, according to the directions of the manufacturer. The results of the ELISA show that vaccination of mice with a single dose of the non-pyrogenic *Salmonella* Blebs harboring POGL1-A1 induced a strong serum IgG response against gp120 (FIG. 2).

The results (FIG. 2) show conclusively that vaccination of mice with both the 10 pg and 50 pg doses of non-pyrogenic *Salmonella* Blebs harboring POGL1-A1 induced a strong serum IgG response against gp120 resulted in the development of strong serum IgG responses against gp120. These data show that non-pyrogenic Blebs are a useful and inexpensive tool for delivering DNA vaccines to the lymphoid compartment in vivo and inducing immune responses against DNA vaccine-encoded DNA vaccines.

While the invention has been described herein with reference to various illustrative features, aspects, and embodiments, it will be appreciated that the utility of the invention is not thus limited, but rather extends to and encompasses other variations, modifications and other embodiments, as will readily suggest themselves to those of ordinary skill in the art. Accordingly, the invention is to be broadly interpreted and construed as including such other variations, modifications and other embodiments, within the spirirt and scope of the invention as hereinafter claimed.

That which is claimed is:

1. A method for introducing and expressing a gene in animal cells comprising infecting said animal cells with bacterial blebs isolated from gram negative bacteria, wherein said bacterial blebs contain a eukaryotic expression cassette encoding said gene to be expressed by said animal cells.

2. The method of claim 1, wherein said animal cell is a mammalian cell.

3. The method of claim 2, wherein said mammalian cell is selected from the group consisting of human, cattle, sheep, goat, home, donkey, primate, and buffalo cells.

4. The method of claim 3, wherein said mammalian cell is a human cell.

5. The method of claim 1, wherein said bacterial blebs are derived from bacteria selected from the group consisting of *Shigella* spp., *Salmonella* spp., *Neisseria* spp., *Haemophilus* spp., *Vibrio* spp., and *Escherichia* spp.

6. The method of claim 5, wherein said bacteria are attenuated.

7. The method of claim 1, wherein said bacterial blebs are derived from gram negative bacteria selected from the group consisting of *Yersinia* spp., *Escherichia* spp., *Klebsiella* spp., *Bordetella* spp., *Neisseria* spp., *Aeromonas* spp., *Franciesella* spp., *Citrobacter* spp., *Chlamydia* spp., *Hemophilus* spp., *Brucella* spp., *Legionella* spp., *Pseudomonas* spp., and *Helicobacter* spp.

8. The method of claim 7, wherein said bacteria are attenuated.

9. The method of claim 1, wherein said animal cells are infected at about $10^{10}$ to $10^{12}$ bacterial blebs per cell.

10. The method of claim 1, wherein said animals cells are cultured in vitro.

11. An isolated bacterial bleb from a gram-negative bacteria, wherein the bacterial bleb comprises a eukaryotic expression cassette.

12. The isolated bacterial bleb of claim 11, from a bacterium selected from bacteria of the group consisting of *Shigella* spp., *Salmonella* spp., *Neisseria* spp., *Haemophilus* spp., *Vibrio* spp., and *Escherichia* spp.

13. The isolated bacterial bleb of claim 12, wherein said bacteria are attenuated.

14. The isolated bacterial bleb of claim 11, from a bacterium selected from bacteria of the group consisting of *Yersinia* spp., *Escherichia* spp., *Klebsiella* spp., *Bordetella* spp., *Neisseria* spp., *Aeromonas* spp., *Franciesella* spp., *Citrobacter* spp., *Chlamydia* spp., *Hemophilus* spp., *Brucella* spp., *Legionella* spp., *Pseudomonas* spp., and *Helicobacter* spp.

15. The isolated bacterial bleb of claim 14, wherein said bacteria are attenuated.

16. The isolated bacterial bleb of claim 11, further comprising a prakaryotic expression cassette.

* * * * *

UNITED STATES PATENT AND TRADEMARK OFFICE
CERTIFICATE OF CORRECTION

| | | |
|---|---|---|
| PATENT NO. | : 7,125,718 B2 | Page 1 of 1 |
| APPLICATION NO. | : 10/432149 | |
| DATED | : October 24, 2006 | |
| INVENTOR(S) | : Robert J. Powell et al. | |

It is certified that error appears in the above-identified patent and that said Letters Patent is hereby corrected as shown below:

In the References Cited, Item [63] page 2, "Other Publications," second column, Ishihana, Akira entry, first line, "polymerase a subunit" should be -- polymerase $\alpha$ subunit --.

In the References Cited, page 6, "Other Publications," second column, Begg et al. entry, second line, "Shpae" should be -- Shape --.

In column 4, line 16, "identical a subunits" should be -- identical $\alpha$ subunits --.

In column 5, line 6, "residue Darnell" should be -- residue (Darnell --.

In column 8, line 11, "xiang et al" should be -- Xiang et al --.

In column 15, line 54, "mentalized(Mesteky," should be -- mentalized (Mesteky, --.

In column 18, line 51, "prior t0" should be -- prior to --.

In column 26, line 24, "BALB/cAnNcrIBR" should be -- BALB/cAnNcrlBR --.

In column 26, line 34, "microfage" should be -- microfuge --.

In column 27, line 50, "$10^{8-109}$" should be -- $10^8$-$10^9$ --.

In column 28, line 12, "BALB/cAnNcrIBR" should be -- BALB/cAnNcrlBR --.

In column 28, line 39, "calorimetrically" should be -- colorimetrically --.

Signed and Sealed this

Seventeenth Day of April, 2007

JON W. DUDAS
*Director of the United States Patent and Trademark Office*

SEQUENCE LISTING

<160> NUMBER OF SEQ ID NOS: 1

<210> SEQ ID NO 1
<211> LENGTH: 7586
<212> TYPE: DNA
<213> ORGANISM: Vibrio cholerae
<220> FEATURE:
<221> NAME/KEY: misc_feature
<222> LOCATION: (6184)..(6184)
<223> OTHER INFORMATION: n can be any one of a, c, g, and t
<220> FEATURE:
<221> NAME/KEY: misc_feature
<222> LOCATION: (6224)..(6224)
<223> OTHER INFORMATION: n can be any one of a, c, g, and t
<220> FEATURE:
<221> NAME/KEY: misc_feature
<222> LOCATION: (6226)..(7053)
<223> OTHER INFORMATION: n can be any one of a, c, g, and t

<400> SEQUENCE: 1

| | | | | | |
|---|---|---|---|---|---|
| ccatggatga | taagttatat | cgggcagatt | ctagacctcc | tgatgaaata | aagcagtcag | 60 |
| gtggtcttat | gccaagagga | cagagtgagt | actttgaccg | aggtactcaa | atgaatatca | 120 |
| acctttatga | tcatgcaaga | ggaactcaga | cgggatttgt | taggcacgat | gatggatatg | 180 |
| tttccacctc | aattagtttg | agaagtgccc | acttagtggg | tcaaactata | ttgtctggtc | 240 |
| attctactta | ttatatatat | gttatagcca | ctgcacccaa | catgtttaac | gttaatgatg | 300 |
| tattaggggc | atacagtcct | catccagatg | aacaagaagt | ttctgcttta | ggtgggattc | 360 |
| catactccca | aatatatgga | tggtatcgag | ttcattttgg | ggtgcttgat | gaacaattac | 420 |
| atcgtaatag | gggctacaga | gatagatatt | acagtaactt | agatattgct | ccagcagcag | 480 |
| atggttatgg | attggcaggt | ttccctccgg | agcatagagc | ttggagggaa | gagccgtgga | 540 |
| ttcatcatgc | accgccgggt | tgtgggaatg | ctccaagatc | atcgtaagcg | gccgctcgag | 600 |
| tctagagggc | ccgtttaaac | ccgctgatca | gcctcgactg | tgccttctag | ttgccagcca | 660 |
| tctgttgttt | gcccctcccc | cgtgccttcc | ttgaccctgg | aaggtgccac | tcccactgtc | 720 |
| ctttcctaat | aaaatgagga | aattgcatcg | cattgtctga | gtaggtgtca | ttctattctg | 780 |
| gggggtgggg | tggggcagga | cagcaagggg | gaggattggg | aagacaatag | caggcatgct | 840 |
| ggggatgcgg | tgggctctat | ggcttctgag | gcggaaagaa | ccagctgggg | ctctaggggg | 900 |
| tatccccacg | cgccctgtag | cggcgcatta | agcgcggcgg | gtgtggtggt | tacgcgcagc | 960 |
| gtgaccgcta | cacttgccag | cgccctagcg | cccgctcctt | tcgctttctt | cccttccttt | 1020 |
| ctcgccacgt | tcgccggctt | tccccgtcaa | gctctaaatc | gggcatccc | tttagggttc | 1080 |
| cgatttagtg | ctttacggca | cctcgacccc | aaaaaacttg | attagggtga | tggttcacgt | 1140 |
| agtgggccat | cgccctgata | gacggttttt | cgccctttga | cgttggagtc | cacgttcttt | 1200 |
| aatagtggac | tcttgttcca | aactggaaca | acactcaacc | ctatctcggt | ctattctttt | 1260 |
| gatttataag | ggattttggg | gatttcggcc | tattggttaa | aaaatgagct | gatttaacaa | 1320 |
| aaatttaacg | cgaattaatt | ctgtggaatg | tgtgtcagtt | agggtgtgga | aagtccccag | 1380 |
| gctccccagg | caggcagaag | tatgcaaagc | atgcatctca | attagtcagc | aaccaggtgt | 1440 |
| ggaaagtccc | caggctcccc | agcaggcaga | agtatgcaaa | gcatgcatct | caattagtca | 1500 |
| gcaaccatag | tcccgcccct | aactccgccc | atcccgcccc | taactccgcc | cagttccgcc | 1560 |
| cattctccgc | cccatggctg | actaattttt | tttatttatg | cagaggccga | ggccgcctct | 1620 |
| gcctctgagc | tattccagaa | gtagtgagga | ggcttttttg | gaggcctagg | cttttgcaaa | 1680 |

```
aagctcccgg gagcttgtat atccattttc ggatctgatc agcacgtgtt gacaattaat    1740
catcggcata gtatatcggc atagtataat acgacaaggt gaggaactaa accatggcca    1800
agttgaccag tgccgttccg gtgctcaccg cgcgcgacgt cgccggagcg gtcgagttct    1860
ggaccgaccg gctcgggttc tcccgggact cgtggagga cgacttcgcc ggtgtggtcc    1920
gggacgacgt gaccctgttc atcagcgcgg tccaggacca ggtggtgccg gacaacaccc    1980
tggcctgggt gtgggtgcgc ggcctggacg agctgtacgc cgagtggtcg gaggtcgtgt    2040
ccacgaactt ccgggacgcc tccgggccgg ccatgaccga gatcggcgag cagccgtggg    2100
ggcgggagtt cgccctgcgc gacccggccg gcaactgcgt gcacttcgtg gccgaggagc    2160
aggactgaca cgtgctacga gatttcgatt ccaccgccgc cttctatgaa aggttgggct    2220
tcggaatcgt tttccgggac gccggctgga tgatcctcca gcgcgggat ctcatgctgg     2280 agttcttcgc ccaccccaac ttgtttattg cagcttataa tggttacaaa taaagcaata    2340
gcatcacaaa tttcacaaat aaagcatttt tttcactgca ttctagttgt ggtttgtcca    2400
aactcatcaa tgtatcttat catgtctgta taccgtcgac ctctagctag agcttggcgt    2460
aatcatggtc atagctgttt cctgtgtgaa attgttatcc gctcacaatt ccacacaaca    2520
tacgagccgg aagcataaag tgtaaagcct ggggtgccta atgagtgagc taactcacat    2580
taattgcgtt gcgctcactg cccgctttcc agtcgggaaa cctgtcgtgc cagctgcatt    2640
aatgaatcgg ccaacgcgcg gggagaggcg gtttgcgtat gggcgctct tccgcttcct     2700 cgctcactga ctcgctgcgc tcggtcgttc ggctgcggcg agcggtatca gctcactcaa    2760
aggcggtaat acggttatcc acagaatcag gggataacgc aggaaagaac atgtgagcaa    2820
aaggccagca aaaggccagg aaccgtaaaa aggccgcgtt gctggcgttt ttccataggc    2880 tccgccccc tgacgagcat cacaaaaatc gacgctcaag tcagaggtgg cgaaacccga     2940
caggactata aagataccag gcgtttcccc ctggaagctc cctcgtgcgc tctcctgttc    3000
cgaccctgcc gcttaccgga tacctgtccg cctttctccc ttcgggaagc gtggcgcttt    3060
ctcaatgctc acgctgtagg tatctcagtt cggtgtaggt cgttcgctcc aagctgggct    3120
gtgtgcacga accccccgtt cagcccgacc gctgcgcctt atccggtaac tatcgtcttg    3180
agtccaaccc ggtaagacac gacttatcgc cactggcagc agccactggt aacaggatta    3240
gcagagcgag gtatgtaggc ggtgctacag agttcttgaa gtggtggcct aactacggct    3300
acactagaag gacagtattt ggtatctgcg ctctgctgaa gccagttacc ttcggaaaaa    3360
gagttggtag ctcttgatcc ggcaaacaaa ccaccgctgg tagcggtggt ttttttgttt    3420
gcaagcagca gattacgcgc agaaaaaaag gatctcaaga agatcctttg atcttttcta    3480
cggggtctga cgctcagtgg aacgaaaact cacgttaagg gattttggtc atgagattat    3540
caaaaaggat cttcacctag atccttttaa attaaaaatg aagttttaaa tcaatctaaa    3600
gtatatatga gtaaacttgg tctgacagtt accaatgctt aatcagtgag gcacctatct    3660
cagcgatctg tctatttcgt tcatccatag ttgcctgact ccccgtcgtg tagataacta    3720
cgatacggga gggcttacca tctggcccca gtgctgcaat gataccgcga ccccacgct    3780 caccggctcc agatttatca gcaataaacc agccagccgg aagggccgag cgcagaagtg    3840
gtcctgcaac tttatccgcc tccatccagt ctattaattg ttgccgggaa gctagagtaa    3900
gtagttcgcc agttaatagt ttgcgcaacg ttgttgccat tgctacaggc atcgtggtgt    3960
cacgctcgtc gtttggtatg gcttcattca gctccggttc ccaacgatca aggcgagtta    4020
```

-continued

```
catgatcccc catgttgtgc aaaaaagcgg ttagctcctt cggtcctccg atcgttgtca   4080
gaagtaagtt ggccgcagtg ttatcactca tggttatggc agcactgcat aattctctta   4140
ctgtcatgcc atccgtaaga tgcttttctg tgactggtga gtactcaacc aagtcattct   4200
gagaatagtg tatgcggcga ccgagttgct cttgcccggc gtcaatacgg gataataccg   4260
cgccacatag cagaacttta aaagtgctca tcattggaaa acgttcttcg ggcgaaaac    4320 tctcaaggat cttaccgctg ttgagatcca gttcgatgta acccactcgt gcacccaact   4380
gatcttcagc atcttttact ttcaccagcg tttctgggtg agcaaaaaca ggaaggcaaa   4440
atgccgcaaa aaagggaata agggcgacac ggaaatgttg aatactcata ctcttccttt   4500
ttcaatatta ttgaagcatt tatcagggtt attgtctcat gagcggatac atatttgaat   4560
gtatttagaa aaataaacaa ataggggttc cgcgcacatt tccccgaaaa gtgccacctg   4620
acgtcgacgg atcgggagat ctcccgatcc cctatggtcg actctcagta caatctgctc   4680
tgatgccgca tagttaagcc agtatctgct ccctgcttgt gtgttggagg tcgctgagta   4740
gtgcgcgagc aaaatttaag ctacaacaag caaggcttg accgacaatt gcatgaagaa    4800
tctgcttagg gttaggcgtt ttgcgctgct tcgcgatgta cgggccagat atacgcgttg   4860
acattgatta ttgactagtt attaatagta atcaattacg gggtcattag ttcatagccc   4920
atatatggag ttccgcgtta cataacttac ggtaaatggc ccgcctggct gaccgcccaa   4980
cgacccccgc ccattgacgt caataatgac gtatgttccc atagtaacgc caatagggac   5040
tttccattga cgtcaatggg tggactattt acggtaaact gcccacttgg cagtacatca   5100
agtgtatcat atgccaagta cgccccctat tgacgtcaat gacggtaaat ggcccgcctg   5160
gcattatgcc cagtacatga ccttatggga ctttcctact tggcagtaca tctacgtatt   5220
agtcatcgct attaccatgg tgatgcggtt ttggcagtac atcaatgggc gtggatagcg   5280
gtttgactca cggggatttc caagtctcca ccccattgac gtcaatggga gtttgttttg   5340
gcaccaaaat caacgggact ttccaaaatg tcgtaacaac tccgccccat tgacgcaaat   5400
gggcggtagg cgtgtacggt gggaggtcta tataagcaga gctctctggc taactagaga   5460
acccactgct tactggctta tcgaaattaa tacgactcac tatagggaga cccaagcatg   5520
gctagcgttt aaacttaagc ttggtaccga gctcggatcc atgccatggg gtctctgca    5580 accgctggcc accttgtacc tgctggggat gctggtcgct tccgtgctag ccaccgagaa   5640
gctgtgggtg accgtgtact acggcgtgcc cgtgtggaag gaggccacca ccaccctgtt   5700
ctgcgccagc gacgccaagg cgtacgacac cgaggtgcac aacgtgtggg ccacccaggc   5760
gtgcgtgccc accgacccca accccccagga ggtggagctc gtgaacgtga ccgagaactt   5820
caacatgtgg aagaacaaca tggtggagca gatgcatgag gacatcatca gcctgtggga   5880
ccagagcctg aagccctgcg tgaagctgac cccctgtgc gtgaccctga actgcaccga   5940
cctgaggaac accaccaaca ccaacaacag caccgccaac aacaacagca acagcgaggg   6000
caccatcaag ggcggcgaga tgaagaactg cagcttcaac atcaccacca gcatccgcga   6060
caagatgcag aaggagtacg ccctgctgta caagcttgga tatcgtgagc atcgacaacg   6120
agagcaccag ctaccgctga tctcttgaac accagcgtga tacccaggcc tgcccaagat   6180
cagnttcgag cccatcccaa tcactactgg ccccgccgg ttncnnnnn nnnnnnnnnn     6240 nnnnnnnnnn nnnnnnnnnn nnnnnnnnnn nnnnnnnnnn nnnnnnnnnn nnnnnnnnnn   6300
nnnnnnnnnn nnnnnnnnnn nnnnnnnnnn nnnnnnnnnn nnnnnnnnnn nnnnnnnnnn   6360
nnnnnnnnnn nnnnnnnnnn nnnnnnnnnn nnnnnnnnnn nnnnnnnnnn nnnnnnnnnn   6420
```

```
nnnnnnnnnn nnnnnnnnnn nnnnnnnnnn nnnnnnnnnn nnnnnnnnnn nnnnnnnnnn      6480
nnnnnnnnnn nnnnnnnnnn nnnnnnnnnn nnnnnnnnnn nnnnnnnnnn nnnnnnnnnn      6540
nnnnnnnnnn nnnnnnnnnn nnnnnnnnnn nnnnnnnnnn nnnnnnnnnn nnnnnnnnnn      6600
nnnnnnnnnn nnnnnnnnnn nnnnnnnnnn nnnnnnnnnn nnnnnnnnnn nnnnnnnnnn      6660
nnnnnnnnnn nnnnnnnnnn nnnnnnnnnn nnnnnnnnnn nnnnnnnnnn nnnnnnnnnn      6720
nnnnnnnnnn nnnnnnnnnn nnnnnnnnnn nnnnnnnnnn nnnnnnnnnn nnnnnnnnnn      6780
nnnnnnnnnn nnnnnnnnnn nnnnnnnnnn nnnnnnnnnn nnnnnnnnnn nnnnnnnnnn      6840
nnnnnnnnnn nnnnnnnnnn nnnnnnnnnn nnnnnnnnnn nnnnnnnnnn nnnnnnnnnn      6900
nnnnnnnnnn nnnnnnnnnn nnnnnnnnnn nnnnnnnnnn nnnnnnnnnn nnnnnnnnnn      6960
nnnnnnnnnn nnnnnnnnnn nnnnnnnnnn nnnnnnnnnn nnnnnnnnnn nnnnnnnnnn      7020
nnnnnnnnnn nnnnnnnnnn nnnnnnnnnn nnngcggccg ctaagtaagt aacttaagtt      7080
ccggttattt tccaccatat tgccgtcttt tggcaatgtg agggcccgga aacctggccc      7140
tgtcttcttg acgagcattc ctagggtct ttccctctc gccaaaggaa tgcaaggtct        7200
gttgaatgtc gtgaaggaag cagttcctct ggaagcttct tgaagacaaa caacgtctgt      7260
agcgaccctt tgcaggcagc ggaaccccc acctggcgac aggtgcctct gcggccaaaa       7320
gccacgtgta taagatacac ctgcaaaggc ggcacaaccc cagtgccacg ttgtgagttg      7380
gatagttgtg gaaagagtca aatggctctc ctcaagcgta ttcaacaagg ggctgaagga     7440
tgcccagaag gtaccccatt gtatgggatc tgatctgggg cctcggtgca catgctttac     7500
atgtgtttag tcgaggttaa aaaacgtcta ggccccccga accacgggga cgtggttttc    7560
ctttgaaaaa cacgatgata atatgg                                          7586
```